United States Patent
Hecker et al.

(10) Patent No.: US 10,654,802 B2
(45) Date of Patent: May 19, 2020

(54) INDOLINE DERIVATIVES AND METHOD FOR USING AND PRODUCING THE SAME

(71) Applicant: ARIZONA BOARD OF REGENTS ON BEHALF OF THE UNIVERSITY OF ARIZONA, Tucson, AZ (US)

(72) Inventors: Louise Hecker, Tucson, AZ (US); Vijay Gokhale, Tucson, AZ (US); Reena Chawla, Tucson, AZ (US)

(73) Assignee: Arizona Board of Regents on Behalf of the Unversit, Tuscon, AZ (US)

( * ) Notice: Subject to any disclaimer, the term of this patent is extended or adjusted under 35 U.S.C. 154(b) by 0 days.

(21) Appl. No.: 16/315,710

(22) PCT Filed: Jul. 7, 2017

(86) PCT No.: PCT/US2017/041179
§ 371 (c)(1),
(2) Date: Jan. 7, 2019

(87) PCT Pub. No.: WO2018/009854
PCT Pub. Date: Jan. 11, 2018

(65) Prior Publication Data
US 2019/0135746 A1    May 9, 2019

Related U.S. Application Data

(60) Provisional application No. 62/360,293, filed on Jul. 8, 2016.

(51) Int. Cl.
| | | |
|---|---|---|
| C07D 209/08 | (2006.01) |
| C07D 403/12 | (2006.01) |
| C07D 401/12 | (2006.01) |
| C07D 405/12 | (2006.01) |
| C07D 417/12 | (2006.01) |
| C07D 417/14 | (2006.01) |
| A61P 29/00 | (2006.01) |
| A61P 11/00 | (2006.01) |

(52) U.S. Cl.
CPC ............ C07D 209/08 (2013.01); A61P 11/00 (2018.01); A61P 29/00 (2018.01); C07D 401/12 (2013.01); C07D 403/12 (2013.01); C07D 405/12 (2013.01); C07D 417/12 (2013.01); C07D 417/14 (2013.01)

(58) Field of Classification Search
CPC ............................. A61P 11/00; C07D 209/08
See application file for complete search history.

(56) References Cited

U.S. PATENT DOCUMENTS

| | | |
|---|---|---|
| 2,528,940 A | 11/1950 | Wright |
| 2,909,523 A | 10/1959 | Bach, Jr. et al. |
| 2004/0209865 A1 | 10/2004 | Stenkamp et al. |
| 2006/0142373 A1 | 6/2006 | Park et al. |
| 2006/0178366 A1 | 8/2006 | Siddiqui et al. |
| 2015/0368195 A1 | 12/2015 | Liou et al. |

FOREIGN PATENT DOCUMENTS

| | | |
|---|---|---|
| WO | 70/12475 A1 | 3/2000 |
| WO | 2012/160392 A1 | 11/2012 |
| WO | 2012/173952 A1 | 12/2012 |
| WO | 2014/210159 A1 | 12/2014 |

OTHER PUBLICATIONS

Szarek et al (2000), STN International (Columbus, Ohio) HCAPLUS database, Accession No. 2000: 841961.*
The International Search Report (ISR) with Written Opinion for PCT/US2017/041179 dated Nov. 30, 2017, pp. 1-14.
Rami et al., "Discovery of SB-705498: A potent, selective and orally bioavailable TRPV1 antagonist suitable for clinical development." Bioorganic & Medicinal Chemistry Letters, 16(12): 3287-3291 (2006).

* cited by examiner

*Primary Examiner* — Golam M Shameem
(74) *Attorney, Agent, or Firm* — McDonnell Boehnen Hulbert & Berghoff LLP

(57) ABSTRACT

The present invention relates to a compound of the formula: where n, $R^1$ and $R^2$ are those defined herein. The present invention also relates to use of a compound of Formula 1 in treating a clinical condition associated with fibrotic disorder.

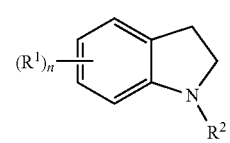

20 Claims, 5 Drawing Sheets

A

B

INDOLINE DERIVATIVES AND METHOD FOR USING AND PRODUCING THE SAME

CROSS-REFERENCE TO RELATED APPLICATION

This application is a U.S. national phase of International Application No. PCT/US2017/041179, filed Jul. 7, 2017, which claims priority to U.S. Provisional Application No. 62/360,293, filed Jul. 8, 2016, both of which are incorporated by reference herein in their entirety.

FIELD OF THE INVENTION

The present invention relates to a compound of the formula:

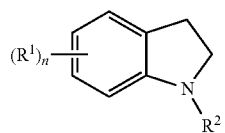

where n, R1 and R2 are those defined herein. The present invention also relates to use of a compound of Formula I in treating a clinical condition associated with fibrotic disorder.

BACKGROUND OF THE INVENTION

Fibrotic disorders affect many organ systems, including heart, blood vessels, kidney, liver and lung. An estimated 45% of deaths in the United States are attributed to disorders that are characterized by varying degrees of fibrosis. This alarming statistic is often underappreciated since the 'cause of death' is often end-stage organ failure, although in many cases organ failure is attributed to progressive fibrosis.

The most severe and deadly fibrotic lung disease is idiopathic pulmonary fibrosis (IPF), characterized by progressive scar tissue formation and irreversible destruction of the lung parenchyma, resulting in gas-exchange abnormalities and ultimately respiratory failure. IPF is widely regarded as a disease of aging, as it disproportionately affects the elderly population with a mean age of 66 years at the time of diagnosis. IPF is associated with high morbidity and mortality with a median survival rate of less than three years. Further, the survival rate for IPF patients markedly decreases with age.

Although two drugs have recently gained FDA-approval for IPF, no drug treatment has been shown to definitively improve quality of life or survival for IPF patients. The current drugs only moderately slow the progression of lung decline. There are no available therapies that can 'reverse' fibrosis.

Therefore, there is a clear need for more effective treatments for IPF and other fibrotic diseases in order to improve the patient experience and outcomes.

SUMMARY OF THE INVENTION

Some aspects of the invention are based on the discovery by the present inventors that the reactive oxygen species (ROS)-generating enzyme, NADPH oxidase (Nox4), is a critical mediator of myofibroblast functions and validation of its role in animal models of lung fibrosis. Nox4 expression is elevated in the lungs of patients with IPF and in IPF lung fibroblasts.

Since this discovery by the present inventors, Nox4 has been implicated in a variety of fibrotic diseases including the kidney, liver, skin, and heart. More recently, the present inventors have developed a novel aging animal model of persistent lung fibrosis. This model more accurately recapitulates the persistent nature of IPF and offers a more clinically relevant efficacy testing protocol, where reversal of established fibrosis can be evaluated. Using this model, the present inventors have demonstrated that, in the context of aging, lung injury leads to the acquisition of a senescent and apoptosis-resistant myofibroblast phenotype, which impairs fibrosis resolution. Without being bound by any theory, it is believed that this myofibroblast phenotype is mediated by a redox imbalance associated with sustained activation of Nox4. Further, genetic/pharmacologic targeting of Nox4 led to the reversal of age-associated persistent fibrosis and increased survival.

Currently, there are no selective Nox4 inhibitors clinically available. One particular aspect of the invention provides is highly selective Nox4 inhibitor compounds. Another aspect of the invention provides a method for using a compound of the invention for treating a subject suffering from a clinical condition associated with fibrotic disorder.

DETAILED DESCRIPTION OF THE INVENTION

Definitions

Figure 1:
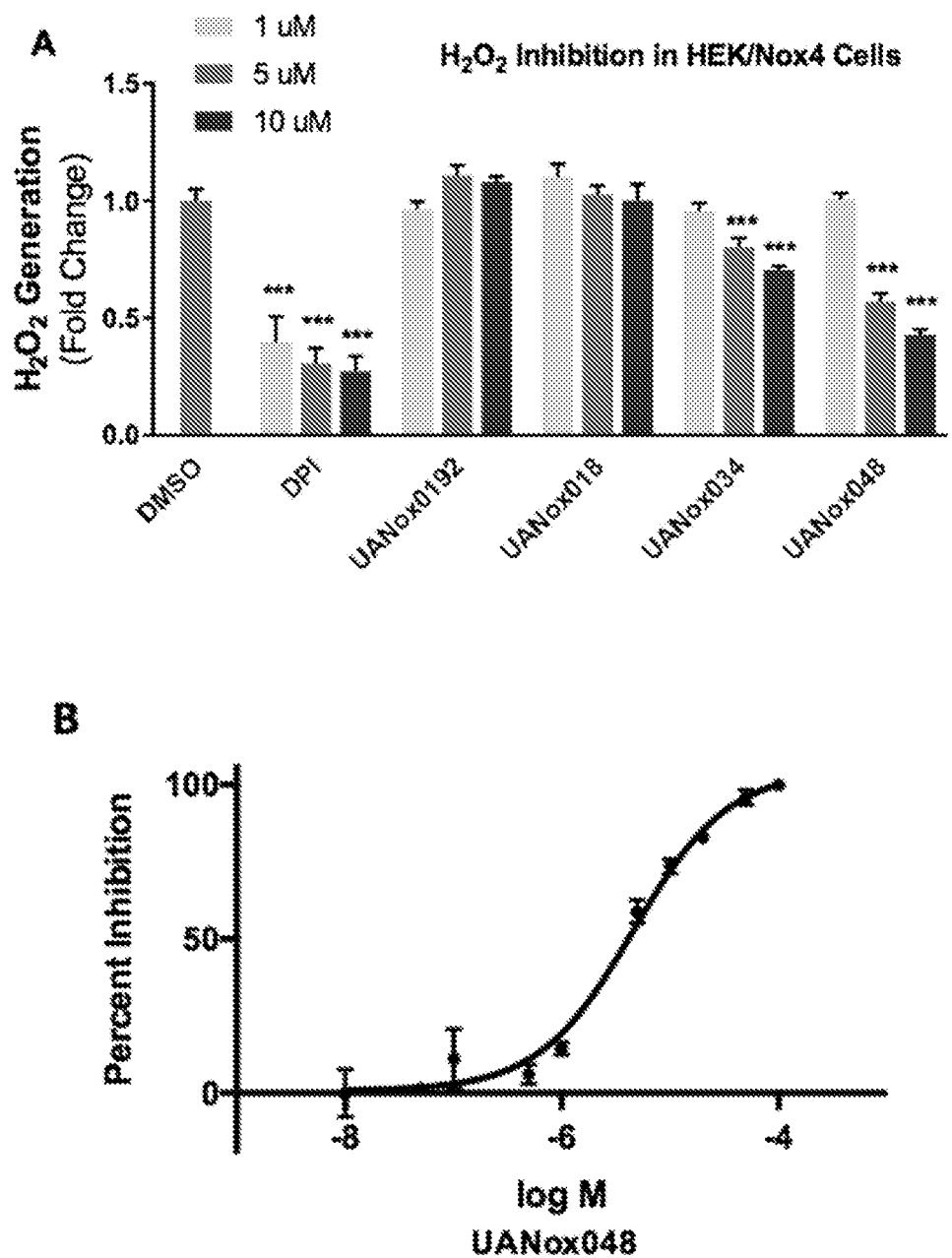
FIG. 1 is a graph showing (A) $H_2O_2$ inhibition by compounds in HEK cells stably transfected to overexpress Nox4 evaluated by Amplex Red assay; and (B) $IC_{50}$ evaluated for UANox048 in HEK cells stably transfected to overexpress Nox4.

As used herein the term "optionally substituted" means one or more substituents may or may not be present. In addition, as is well known to one skilled in the art, the term "substituent" refers to a group other than hydrogen. For example, the term "optionally substituted" means that the referenced chemical structure is unsubstituted or contains at least one substituent selected from the list consisting of halogen, cyano, $C_{1-6}$alkyl, $C_{1-6}$alkenyl, $C_{1-6}$alkynyl, $C_{1-6}$haloalkyl, —O—$C_{1-6}$alkyl, —O—$C_{1-6}$alkenyl, —O—$C_{1-6}$alkynyl, —O—$C_{1-6}$haloalkyl, phenyl, -phenyl-OMe, -phenyl-$CF_3$, $C_{1-6}$alkyl-fluorophenyl, pyridyl, —O— phenyl, —$C_{1-6}$alkyl-phenyl, —O—$C_{1-6}$alkyl-phenyl, —O-pyridyl-$CF_3$, haloalkyl-substituted —O— pyridyl, pyrimidinyl, —OH, —OMe, —NH$_2$, —N(H)Me, —NHC(O)Me, —C(O)NEt$_2$, —SH, —S(O)$_2$-piperidinyl, —S(O)$_2$-phenyl-CF$_3$, —S(O)$_2$-phenyl-OCF$_3$, —S(O)$_2$-fluorophenyl, —S(O)$_2$NMe$_2$, —S(O)$_2$NEt$_2$ and —SMe.

"Alkyl" refers to a saturated linear monovalent hydrocarbon moiety of one to twelve, typically one to six, carbon atoms or a saturated branched monovalent hydrocarbon moiety of three to twelve, typically three to six, carbon atoms. Exemplary alkyl group include, but are not limited to, methyl, ethyl, n-propyl, 2-propyl, tert-butyl, pentyl, and the like.

"Alkylene" refers to a saturated linear saturated divalent hydrocarbon moiety of one to twelve, typically one to six, carbon atoms or a branched saturated divalent hydrocarbon moiety of three to twelve, typically three to six, carbon atoms. Exemplary alkylene groups include, but are not limited to, methylene, ethylene, propylene, butylene, pentylene, and the like.

"Aryl" refers to a monovalent mono-, bi- or tricyclic aromatic hydrocarbon moiety of 6 to 15 ring atoms which is optionally substituted with one or more substituents. When substituted, the aryl group is typically substituted with one, two or three substituents within the ring structure. When two or more substituents are present in an aryl group, each substituent is independently selected. When substituted, typical substituents for the aryl group include, but are not limited to, alkyl, alkoxy, haloalkyl, haloalkoxy, heteroalkyl, halo, nitro, cyano, cycloalkyl, optionally substituted phenyl, optionally substituted heteroaryl, optionally substituted heterocycloalkyl, or optionally substituted aryl. More specifically the term aryl includes, but is not limited to, optionally substituted phenyl, optionally substituted 1-naphthyl, and optionally substituted 2-naphthyl, etc.

"Aralkyl" refers to a moiety of the formula —R$^{a1}$R$^{a2}$ where R$^{a1}$ is an alkylene group and R$^{a2}$ is an optionally substituted aryl group as defined herein. Exemplary aralkyl groups include, but are not limited to, benzyl, phenylethyl, 3-(3-chlorophenyl)-2-methylpentyl, and the like.

"Cycloalkyl" refers to a non-aromatic, monovalent mono- or bicyclic hydrocarbon moiety of three to ten ring carbons. The cycloalkyl can be optionally substituted with one or more substituents. When substituted, cycloalkyl typically has one, two, or three substituents within the ring structure, where each substituent is independently selected. Cycloalkyl can also include one or more non-aromatic unsaturated double bond within the ring structure. However, the term "saturated" is used as a prefix, then no multiple (e.g., double or triple) bond is present within the cycloalkyl ring structure. Suitable substituents for cycloalkyl include, but not limited to, exemplary substituents listed above for an aryl group.

"Cycloalkylalkyl" refers to a moiety of the formula —R$^{b1}$R$^{b2}$ where R$^{b1}$ is an alkylene group and R$^{b2}$ is an optionally substituted cycloalkyl group as defined herein. Exemplary cycloalkylalkyl groups include, but are not limited to, cyclopropylmethyl, cyclohexylpropyl, 3-cyclohexyl-2-methylpropyl, and the like.

The terms "halo," "halogen" and "halide" are used interchangeably herein and refer to fluoro, chloro, bromo, or iodo.

"Haloalkyl" refers to an alkyl group as defined herein in which one or more hydrogen atom is replaced by same or different halo atoms. The term "haloalkyl" also includes perhalogenated alkyl groups in which all alkyl hydrogen atoms are replaced by halogen atoms. Exemplary haloalkyl groups include, but are not limited to, —CH$_2$Cl, —CF$_3$, —CH$_2$CF$_3$, —CH$_2$CCl$_3$, and the like.

The term "heteroaryl" means a monovalent monocyclic or bicyclic aromatic moiety of 5 to 12 ring atoms containing one, two, three or four ring heteroatoms selected from N, O, or S, the remaining ring atoms being C. The heteroaryl ring can optionally be substituted with one or more substituents. When substituted, typically heteroaryl has one, two or three substituents, each of which is independently selected. Exemplary substituents for heteroaryl include those listed above for aryl group. Exemplary heteroaryl groups include, but are not limited to, pyridyl, furanyl, thiophenyl, thiazolyl, isothiazolyl, triazolyl, imidazolyl, isoxazolyl, pyrrolyl, pyrazolyl, pyrazinyl, pyrimidinyl, benzofuranyl, isobenzofuranyl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl, dibenzofuran, benzodiazepin-2-one-5-yl, and the like.

The terms "heterocyclyl" and "heterocycloalkyl" are used interchangeably herein and refer to a non-aromatic monocyclic moiety of three to eight ring atoms in which one or two ring atoms are heteroatoms selected from N, O, or S(O)$_n$ (where n is an integer from 0 to 2), the remaining ring atoms being C, where one or two C atoms can optionally be a carbonyl group. The heterocyclyl ring can be optionally substituted independently with one or more substituents. When substituted, heterocycloalkyl typically has one, two or three substituents, each of which is independently selected. Heterocycloalkyl can include one or more non-aromatic double bonds within the ring structure. However, the term "saturated" is used as a prefix, then no multiple (e.g., double or triple) bond is present within the heterocycloalkyl ring structure. Suitable substituents for heterocycloalkyl include, but not limited to, exemplary substituents listed above for an aryl group.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Pharmaceutically acceptable excipient" refers to an excipient that is useful in preparing a pharmaceutical composition that is generally safe, non-toxic and neither biologically nor otherwise undesirable, and includes excipient that is acceptable for veterinary use as well as human pharmaceutical use.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1 carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "pro-drug" and "prodrug" are used interchangeably herein and refer to any compound which releases an active parent drug according to Formula I in vivo when such prodrug is administered to a mammalian subject. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of Formula I, and the like.

"Protecting group" refers to a moiety, except alkyl groups, that when attached to a reactive group in a molecule masks, reduces or prevents that reactivity. Examples of protecting groups can be found in T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

"Corresponding protecting group" means an appropriate protecting group corresponding to the heteroatom (i.e., N, O, P or S) to which it is attached.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

As used herein, the term "treating", "contacting" or "reacting" when referring to a chemical reaction means adding or mixing two or more reagents under appropriate conditions to produce the indicated and/or desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

As used herein, the terms "those defined above" and "those defined herein" when referring to a variable incorporates by reference the broad definition of the variable as well as any and all of the more narrower definitions, if any.

Compounds of the Invention

One aspect of the invention provides a compound of the formula:

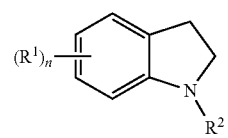

I wherein
n is an integer from 0 to 4;
each $R^1$ is independently selected from the group consisting of alkyl, haloalkyl, halogen, nitro, heterocycloalkyl, cycloalkyl, optionally substituted heteroaryl, optionally substituted aryl, and —$OR^a$, where each $R^a$ is independently selected from the group consisting of hydrogen, alkyl, heteroaryl, aryl and cycloalkyl; or
two adjacent $R^1$ together with carbon atoms to which they are attached to form heterocycloalkyl;
$R^2$ is selected from the group consisting of:
(a) a moiety of the formula:

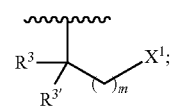

(b) a moiety of the formula:

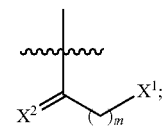

(c) an optionally substituted aryl; and
(d) an optionally substituted heterocycloalkyl,
wherein
m is 1 or 2,
$X^1$ is optionally substituted heterocycloalkyl, —$NR^4R^5$, —$NR^bSO_2R^6$, —$NR^bC(O)R^6$, —$NR^bSO_2NR^4R^5$, or —$NR^bCONR^4R^5$;
$X^2$ is O, NR or S;
$R^3$ and $R^{3'}$ are each independently hydrogen or alkyl;
each of $R^4$ and $R^5$ is independently hydrogen or alkyl, or $R^4$ and $R^5$ together with the nitrogen atom to which they are attached to form an optionally substituted heterocycloalkyl;
each of $R^b$ and $R^c$ is independently hydrogen or alkyl; and
$R^6$ is —$N(R^d)_2$, optionally substituted aryl, optionally substituted heteroaryl or optionally substituted heterocyclyl;

provided that the compound is not:
N—(N,N-diethylaminosulfonyl)-2-(indolin-1-yl)propane-1-amine);
1,1-diethyl-3-(2-(indolin-1-yl)ethyl)urea;
(N—N,N-dimethylaminosulfonyl)-2-(indolin-1-yl)ethane-1-amine);
4-(2-(indolin-1-yl)ethyl)morpholine;
1-(2-(piperidin-1-yl)ethyl)indoline;
N-(2-(indolin-1-yl)propyl)morpholine-4-sulfonamide;
N-(2-(indolin-1-yl)propyl)piperidine-1-sulfonamide;
4-fluoro-N-(2-(indolin-1-yl)propyl)benzenesulfonamide;
4-fluoro-N-(2-(indolin-1-yl)ethyl)benzenesulfonamide;
N-(2-(indolin-1-yl)ethyl)-4-methoxybenzenesulfonamide;
3,4-difluoro-N-(2-(indolin-1-yl)propyl)benzenesulfonamide;
N-(2-(indolin-1-yl)propyl)-2,3-dihydrobenzo[b][1,4]dioxine-6-sulfonamide;
N-(2-(indolin-1-yl)ethyl)benzo[d][1,3]dioxole-5-sulfonamide;
N-(2-(indolin-1-yl)ethyl)-2,3-dihydrobenzo[b][1,4]dioxine-6-sulfonamide;
N,N-diethyl-4-(2-(indolin-1-yl)-2-oxoethyl)piperazine-1-sulfonamide;
1-(indolin-1-yl)-2-(4-(morpholinosulfonyl)piperazin-1-yl)ethan-1-one;
1-(indolin-1-yl)-2-(4-(pyrimidin-2-yl)piperazin-1-yl)ethan-1-one;
4-(3-(indolin-1-yl)-3-oxopropyl)-N,N-dimethylpiperazine-1-sulfonamide;
N,N-diethyl-4-(3-(indolin-1-yl)-3-oxopropyl)piperazine-1-sulfonamide;
1-(indolin-1-yl)-3-(4-(morpholinosulfonyl)piperazin-1-yl)propan-1-one;
1-(indolin-1-yl)-3-(4-(pyrimidin-2-yl)piperazin-1-yl)propan-1-one;
2-(cycloheptylamino)-1-(indolin-1-yl)ethan-1-one; or
3-(cycloheptylamino)-1-(indolin-1-yl)propan-1-one.

One aspect of the invention provides a compound of the formula:

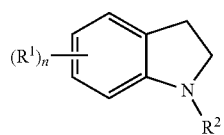

I wherein
n is an integer from 0 to 4;
each $R^1$ is independently selected from the group consisting of alkyl, halogen, nitro, heterocycloalkyl, cycloalkyl, optionally substituted heteroaryl, optionally substituted aryl, and —$OR^a$, where each $R^a$ is independently selected from the group consisting of hydrogen, alkyl, heteroaryl, aryl and cycloalkyl;
or two adjacent $R^1$ together with carbon atoms to which they are attached to form heterocycloalkyl;

$R^2$ is
(a) a moiety of the formula:

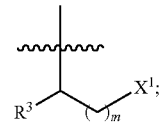

(b) a moiety of the formula,

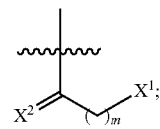

(c) an optionally substituted aryl; or
(d) an optionally substituted heterocycloalkyl,
wherein
m is 1 or 2,
$X^1$ is optionally substituted heterocycloalkyl, —$NR^4R^5$, —$NR^bSO_2R^6$, —$NR^bC(O)R^6$, —$NR^bSO_2NR^4R^5$, or —$NR^bCONR^4R^5$;
$X^2$ is O, NR or S;
$R^3$ is hydrogen or alkyl, typically $R^3$ is hydrogen or methyl;
each of $R^4$ and $R^5$ is independently hydrogen or alkyl,
alternatively, $R^4$ and $R^5$ together with the nitrogen atom to which they are attached to form an optionally substituted heterocycloalkyl,
each of $R^b$ and $R^c$ is independently hydrogen or alkyl; and
$R^6$ is optionally substituted aryl, optionally substituted heteroaryl.

Within the Compound of Formula I, when $R^2$ is a moiety of the formula:

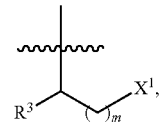

and m is 1, and $R^3$ is —$CH_3$, and $X^1$ is —$NHSO_2NR^4R^5$, then $R^4$ and $R^5$ both are not ethyl.

In one embodiment, m is 1. Yet in another embodiment, m is 2.

Still in another embodiment, $R^2$ is a moiety of the formula:

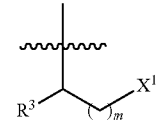

where m, $X^1$ and $R^3$ are those defined herein.

Yet in other embodiments $R^4$ and $R^5$ are independently selected from the group consisting of methyl and ethyl. Still in other embodiments, $R^4$ and $R^5$ together with the nitrogen atom to which they are attached to form a heterocycloalkyl of the formula:

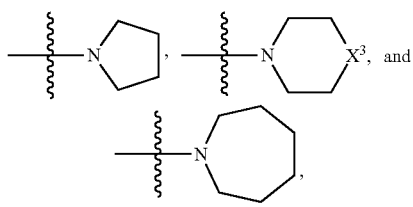

where
X³ is O or —NR⁷; and
R⁷ is alkyl, heteroaryl, or —SO₂NR⁸R⁹,
wherein
each of R⁸ and R⁹ is independently selected from alkyl, or R⁸ and R⁹ together with the nitrogen atom to which they are attached to form an optionally substituted heteroaryl or optionally substituted heterocycloalkyl.

Within these embodiments, in some instances X³ is —NR⁷, where R⁷ is as defined herein. In some particular cases, R⁷ is methyl, ethyl, optionally substituted pyrimidin-2-yl, optionally substituted morpholin-4-yl or optionally substituted piperidin-1-yl.

Yet in other embodiments, X² is O.

In other embodiments, R² is optionally substituted aryl. In some particular embodiments, R² is phenyl that is optionally substituted with alkyl, haloalkyl, optionally substituted cycloalkyl, optionally substituted aryl, optionally substituted heteroaryl, —NR⁴R⁵, —NR^b SO₂R⁶, —NR^b C(O)R⁶, —NR^b SO₂NR⁴R⁵, or —NR^b CONR⁴R⁵, where R^b, R⁴, R⁵ and R⁶ are those defined herein.

Still in other embodiments, R² is optionally substituted heterocycloalkyl. In some instances, R² is an optionally substituted piperidin-3-yl. Yet in other instances, piperidin-3-yl is optionally substituted with alkyl, optionally substituted cycloalkyl, optionally substituted aryl, optionally substituted aralkyl, optionally substituted heteroaryl, optionally substituted heteroarylalkyl, -

In some embodiments, n is 1.

Yet in other embodiments, R¹ is alkyl, haloalkyl, alkoxy, optionally substituted phenyl, optionally substituted pyrazolyl, optionally substituted pyridinyl, or optionally substituted pyrimidinyl, or two of R¹ groups adjacent to one another together with carbon atoms to which they are attached to form heterocycloalkyl. Some of the specific examples of R¹ include those selected from the group consisting of methyl, trifluoromethyl, methoxy, 4-fluorophenyl, 4-(trifluoromethyl)phenyl, 4-nitrophenyl, 4-(N,N-dimethylamino)phenyl, 4-methoxyphenyl, 3-methoxyphenyl, 1-methyl-1H-pyrazol-4-yl, pyridin-2-yl, pyridin-3-yl, pyridin-4-yl, pyrimidin-2-yl, and benzo[d][1,3]dioxol-5-yl. Still in other examples include where n is 2 and two R¹ groups are adjacent to one another together form a moiety of the formula —O[CH₂]ₖO—, where k is 1 or 2.

In some embodiments,
n is 0 or 1;
R¹ is optionally substituted aryl;
X¹ is —NR⁴R⁵, —NR^b C(O)R⁶, —NR^b SO₂NR⁴R⁵ or —NR^b SO₂R⁶;
R³ is hydrogen or alkyl;
each of R⁴ and R⁵ is independently hydrogen or alkyl, or R⁴ and R⁵ together with the nitrogen atom to which they are attached to form an optionally substituted heterocycloalkyl;
R^b is hydrogen or alkyl; and
R⁶ is optionally substituted aryl or optionally substituted heterocyclyl.

In some embodiments,
X¹ is —NR⁴R⁵, —NHC(O)R⁶, —NHSO₂NR⁴R⁵ or —NHSO₂R⁶;
R³ is hydrogen or methyl;
R⁴ and R⁵ are alkyl,
or R⁴ and R⁵ together with the nitrogen atom to which they are attached to form an optionally substituted piperazine ring; and
R⁶ is optionally substituted phenyl or optionally substituted pyrolidinyl.

In some embodiments,
X¹ is —NR⁴R⁵, —NHC(O)R⁶, —NHSO₂NR⁴R⁵ or —NHSO₂R⁶;
R³ is hydrogen or methyl;
R⁴ and R⁵ are ethyl,
or R⁴ and R⁵ together with the nitrogen atom to which they are attached to form an optionally substituted piperazine ring; and
R⁶ is optionally substituted phenyl or optionally substituted pyrolidinyl.

In some embodiments,
n is 1;
R¹ is 3-methoxyphenyl; and
R⁴ and R⁵ are ethyl.

In some embodiments,
n is 0;
R⁴ and R⁵ together with the nitrogen atom to which they are attached to form piperazine ring substituted with R⁷, wherein R⁷ is alkyl —SO₂R¹² or —SO₂NR⁸R⁹, wherein
R⁴ and R⁵ are alkyl,
R¹² is optionally substituted aryl; and
R⁶ is phenyl or pyrolidinyl, wherein the phenyl is substituted with one or more of halogen, haloalkyl, —O-haloalkyl, —O-(5-(trifluoromethyl)pyridin-2-yl), —O-phenyl, cyano, -4-methoxyphenyl.

In some embodiments, R³ is hydrogen.
In some embodiments, R³ is alkyl.
In some embodiments, R³ is methyl.

Some of the representative compounds of the invention are provided in Tables 1-4 below:

TABLE 1

Structures of NOX4 inhibitors

[Structure: indoline core with positions numbered 1-7, R³ at position 6, and N1 substituted with CH(R¹)(R²)]

| Compound | R¹ | R² | R³ |
|---|---|---|---|
| 1 (UANOX001) | H | −NH−S(O)₂−N(CH₂CH₃)₂ | H |
| 2 (UANOX002) | H | −NH−C(O)−N(CH₂CH₃)₂ | H |
| 3 (UANOX003) | H | −NH−S(O)₂−N(CH₃)₂ | H |
| 4 (UANOX004) | H | −NH−S(O)₂−(pyrrolidin-1-yl) | H |
| 5 (UANOX011) | H | −NH−C(O)−(4-methylpiperazin-1-yl) | H |
| 6 (UANOX012) | H | −NH−S(O)₂−(morpholin-4-yl) | H |
| 7 (UANOX021) | H | −NH−C(O)−(pyrrolidin-1-yl) | H |
| 8 (UANOX013) | H | −NH−S(O)₂−(piperidin-1-yl) | H |

TABLE 1-continued

Structures of NOX4 inhibitors

[Structure: indoline core with positions numbered 1-7, R³ at position 5, and N1 substituted with CH(R¹)(R²)]

| Compound | R¹ | R² | R³ |
|---|---|---|---|
| 9 (UANOX017) | H | morpholin-4-yl | H |
| 10 (UANOX018) | H | piperidin-1-yl | H |
| 11 (UANOX006) | CH₃ | -NH-C(=O)-N(CH₂CH₃)₂ | H |
| 12 (UANOX007) | CH₃ | -NH-S(=O)₂-N(CH₃)₂ | H |
| 13 (UANOX008) | CH₃ | -NH-S(=O)₂-pyrrolidin-1-yl | H |
| 14 (UANOX019) | CH₃ | -NH-C(=O)-(4-methylpiperazin-1-yl) | H |
| 15 (UANOX010) | CH₃ | -NH-S(=O)₂-morpholin-4-yl | H |
| 16 (UANOX020) | CH₃ | -NH-C(=O)-pyrrolidin-1-yl | H |

TABLE 1-continued
Structures of NOX4 inhibitors
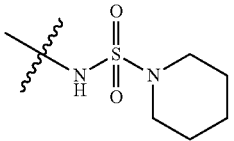 [SMILES: *NS(=O)(=O)N1CCCCC1]
| Compound | R¹ | R² | R³ |
|---|---|---|---|
| 17 (UANOX009) | CH₃ | 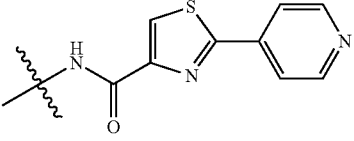 [SMILES: *NC(=O)c1csc(-c2ccncc2)n1] | H |
| 18 (UANOX033) | CH₃ | 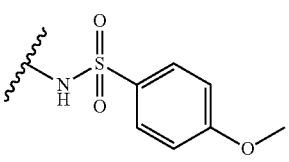 [SMILES: *NS(=O)(=O)c1ccc(OC)cc1] | H |
| 19 (UANOX034) | CH₃ | 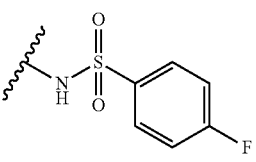 [SMILES: *NS(=O)(=O)c1ccc(F)cc1] | H |
| 20 (UANOX035) | CH₃ | 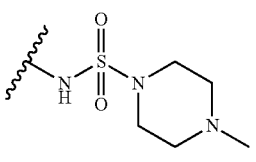 [SMILES: *NS(=O)(=O)N1CCN(C)CC1] | H |
| 21 (UANOX037) | CH₃ | 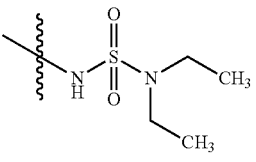 | H |
| 22 (UANOX036) | CH₃ | 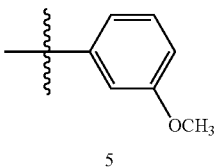 [SMILES: *c1cccc(OC)c1] | 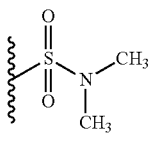 5 |
| 23 | CH₃ | 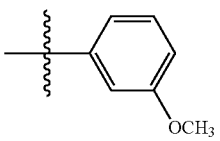 | 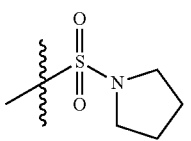 [SMILES: *S(=O)(=O)N1CCCC1] 5 |
| 24 | CH₃ | 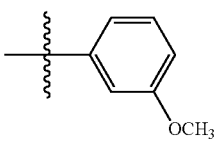 | 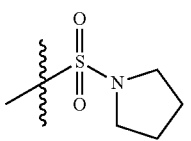 [SMILES: *S(=O)(=O)N1CCCC1] 5 |

TABLE 1-continued

Structures of NOX4 inhibitors

| Compound | R¹ | R² | R³ |
|---|---|---|---|
| 25 | CH₃ | sulfonyl-piperidine | 3-methoxyphenyl (position 5) |
| 26 | CH₃ | sulfonyl-morpholine | 3-methoxyphenyl (position 5) |
| 27 | CH₃ | carbonyl-(4-methyl)piperazine | 3-methoxyphenyl (position 5) |
| 28 (RC_02_54) | CH₃ | NH-sulfonyl-(4-methyl)piperazine | 3-methoxyphenyl (position 5) |
| 29 | CH₃ | sulfonyl-(4-fluorophenyl) | 3-methoxyphenyl (position 5) |
| 30 | CH₃ | sulfonyl-phenyl | 3-methoxyphenyl (position 5) |
| 31 | CH₃ | sulfonyl-(4-methoxyphenyl) | 3-methoxyphenyl (position 5) |

TABLE 1-continued

Structures of NOX4 inhibitors

| Compound | R¹ | R² | R³ |
|---|---|---|---|
| 32 (UANOX049) | CH₃ | -NH-SO₂-C₆H₄-OCF₃ (para) | H |
| 33 (UANOX051) | H | -NH-SO₂-C₆H₄-F (para) | H |
| 34 (UANOX050) | H | -NH-SO₂-C₆H₄-OMe (para) | H |
| 35 (UANOX048) | CH₃ | -NH-SO₂-C₆H₄-CF₃ (para) | H |
| 36 (UANOX055) | CH₃ | -NH-C(O)-(thiazole)-C₆H₅ | H |
| 37 (UANOX056) | CH₃ | -NH-C(O)-(thiazole)-C₆H₄-CF₃ (para) | H |
| 38 (UANOX054) | CH₃ | -NH-C(O)-(thiazole)-C₆H₄-OMe (para) | H |
| 39 | CH₃ | -SO₂-C₆H₄-CN (para) | H |

TABLE 1-continued
Structures of NOX4 inhibitors
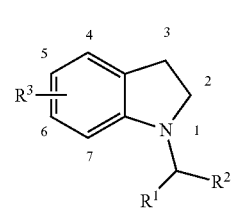
| Compound | R¹ | R² | R³ |
|---|---|---|---|
| 40 (UANOX072) | CH₃ | 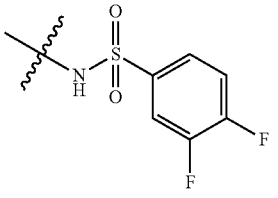 [SMILES: *NS(=O)(=O)c1ccc(F)c(F)c1] | H |
| 41 | CH₃ | 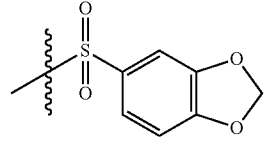 [SMILES: *S(=O)(=O)c1ccc2c(c1)OCO2] | H |
| 42 (UANOX069) | CH₃ | 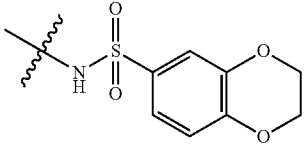 [SMILES: *NS(=O)(=O)c1ccc2c(c1)OCCO2] | H |
| 43 | CH₃ | 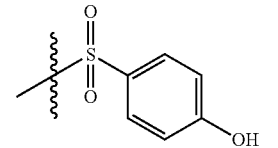 [SMILES: *S(=O)(=O)c1ccc(O)cc1] | H |
| 44 | CH₃ | 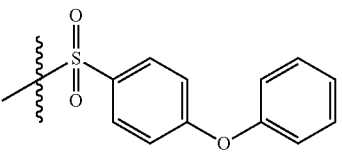 [SMILES: *S(=O)(=O)c1ccc(Oc2ccccc2)cc1] | H |
| 45 (UANOX070) | CH₃ | 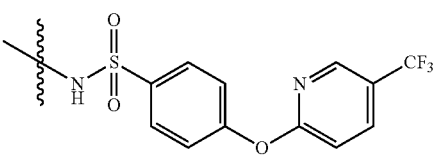 [SMILES: *NS(=O)(=O)c1ccc(Oc2ccc(C(F)(F)F)cn2)cc1] | H |
| UANOX075 | H | 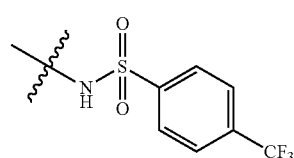 | |
| UANOX076 | H | 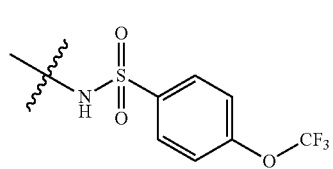 [SMILES: *NS(=O)(=O)c1ccc(OC(F)(F)F)cc1] | |

TABLE 1-continued

Structures of NOX4 inhibitors

| Compound | R¹ | R² | R³ |
|---|---|---|---|
| UANOX077 | H | -NH-SO₂-(benzo[1,3]dioxol-5-yl) | |
| UANOX078 | H | -NH-SO₂-(2,3-dihydro-1,4-benzodioxin-6-yl) | |
| UANOX079 | H | -NH-SO₂-(4-phenoxyphenyl) | |
| UANOX080 | H | -NH-SO₂-C₆H₄-O-(5-(trifluoromethyl)pyridin-2-yl) | |
| UANOX081 | H | -NH-SO₂-(3,4-difluorophenyl) | |

TABLE 2
Structures of NOX4 inhibitors
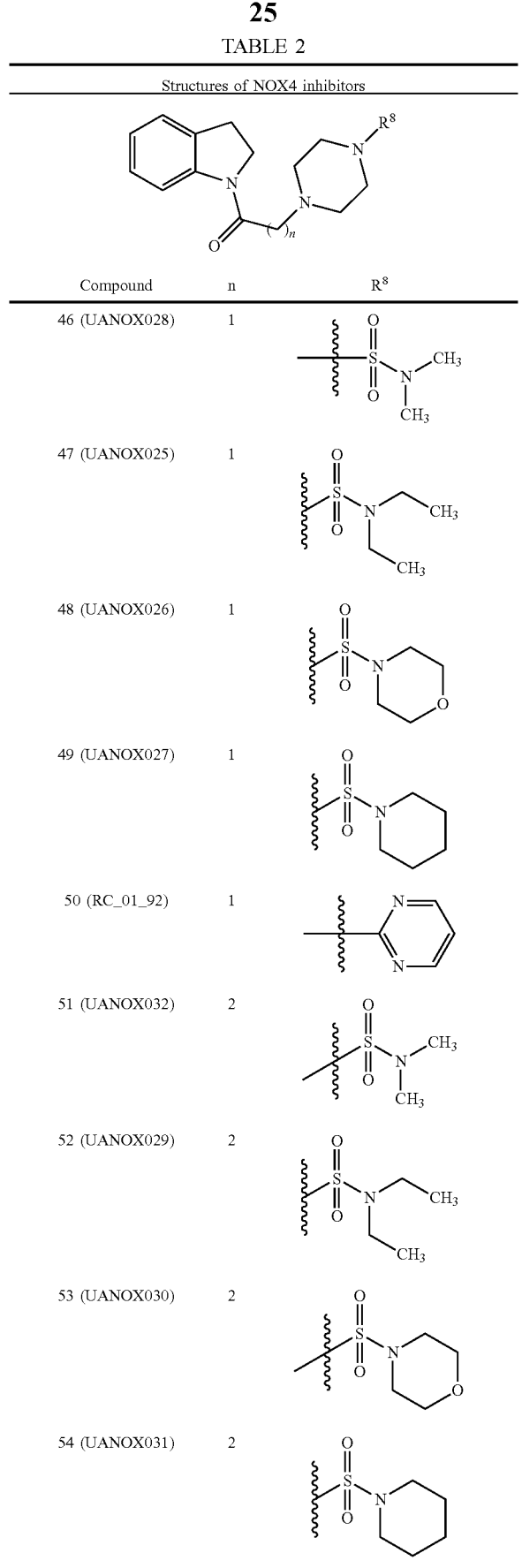
TABLE 2-continued
Structures of NOX4 inhibitors
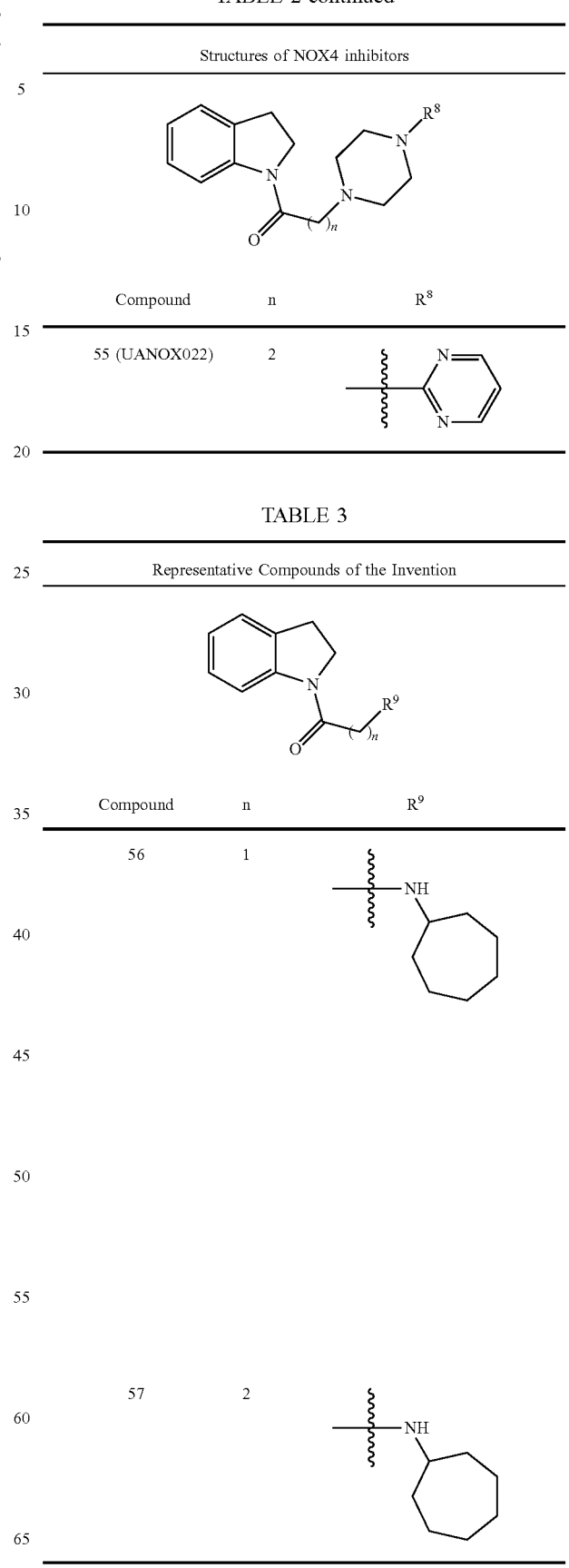

TABLE 4
Representative Compounds of the Invention
| Compound | R<sup>10</sup> |
|---|---|
| 58 (UANOX038) | 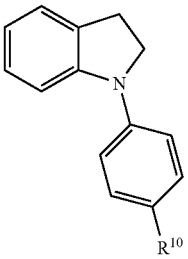 |
| 59 | 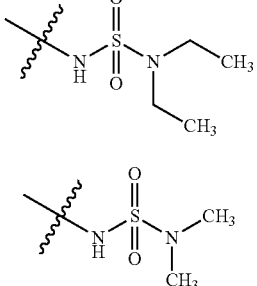 |
| 60 | 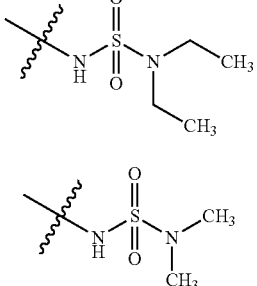 |
| 61 | 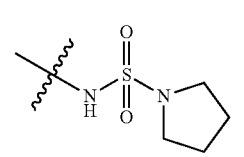 [SMILES: *NS(=O)(=O)N1CCCC1] |
| 62 | 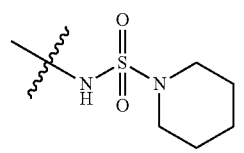 [SMILES: *NS(=O)(=O)N1CCCCC1] |
| 63 | 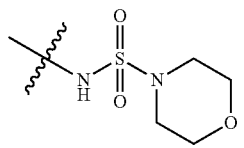 [SMILES: *NS(=O)(=O)N1CCOCC1] |
| 64 | 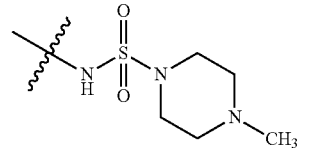 [SMILES: *NS(=O)(=O)N1CCN(C)CC1] |
| 65 | 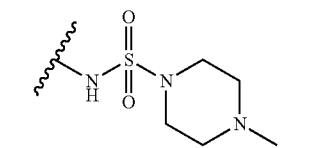 [SMILES: *NS(=O)(=O)N1CCN(C)CC1] |
TABLE 4-continued
Representative Compounds of the Invention
| Compound | R$^{10}$ |
|---|---|
| 66 | 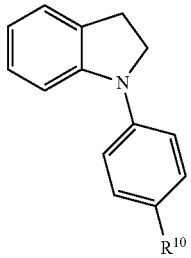 |
| 67 | 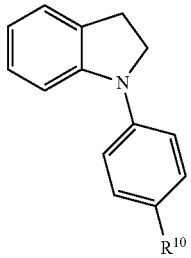 |
TABLE 5
Representative Compounds of the Invention
| Compound | R$^{11}$ |
|---|---|
| 68 | 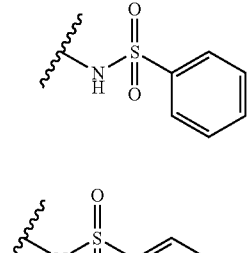 |
| 69 | 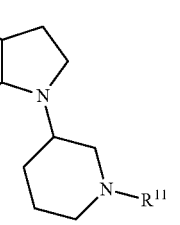 |
| 70 | 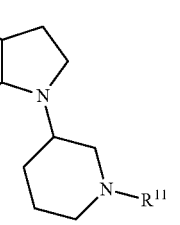 |

TABLE 5-continued

Representative Compounds of the Invention

[Structure: indoline N-linked to piperidine with N-R¹¹]

| Compound | R¹¹ |
|---|---|
| 71 | -S(=O)₂-N(piperidine) |
| 72 | -S(=O)₂-N(morpholine) |
| 73 | -C(=O)-N(4-methylpiperazine) |
| 74 | -S(=O)₂-N(4-methylpiperazine) |
| 75 | -S(=O)₂-(4-fluorophenyl) |
| 76 | -S(=O)₂-phenyl |
| 77 | -S(=O)₂-(4-methoxyphenyl) |

TABLE 6

Structures of NOX4 inhibitors

[Structure: indoline-N-CH₂CH₂-piperazine-N-R²]

| Compound | R¹¹ |
|---|---|
| 78 | -S(=O)₂-(4-fluorophenyl) |
| 79 | -S(=O)₂-phenyl |

TABLE 6-continued

Structures of NOX4 inhibitors

| Compound | R[11] |
|---|---|
| 80 | 4-methoxyphenylsulfonyl |
| 81 (UANOX062) | 4-(trifluoromethoxy)phenylsulfonyl |
| 82 | 4-(trifluoromethyl)phenylsulfonyl |
| 83 | 4-cyanophenylsulfonyl |
| 84 | 3,4-difluorophenylsulfonyl |
| 85 | benzo[d][1,3]dioxol-5-ylsulfonyl |
| 86 | 2,3-dihydrobenzo[b][1,4]dioxin-6-ylsulfonyl |
| 87 | 4-hydroxyphenylsulfonyl |

TABLE 6-continued
Structures of NOX4 inhibitors
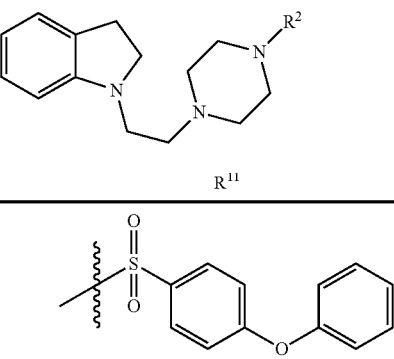
| Compound | R[11] |
|---|---|
| 88 | 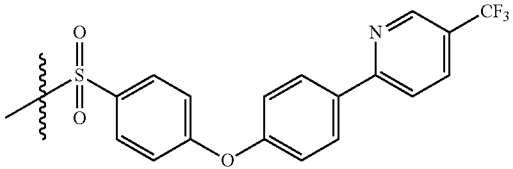 [SMILES: *S(=O)(=O)c1ccc(Oc2ccc(-c3ccc(C(F)(F)F)cn3)cc2)cc1] |
| 89 | 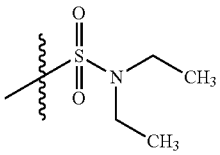 |
| 90 (UANOX063) | 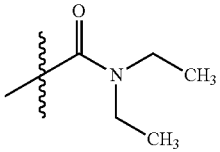 |
| 91 (UANOX066) | 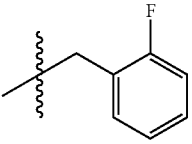 [SMILES: *Cc1ccccc1F] |
| 92 (UANOX067) | 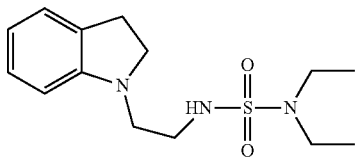 |
In some embodiments, the compound is
| Compound Number | Compound Structure | Compound Name |
|---|---|---|
| UANOX001 | 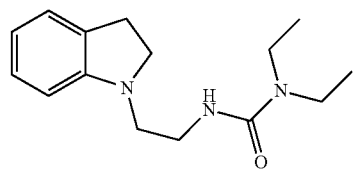 | N-(N,N-diethylaminosulfonyl)-2-(indolin-1-yl)ethane-1-amine |
| UANOX002 | 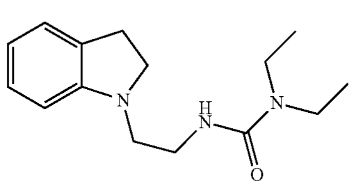 [SMILES: CCN(CC)C(=O)NCCN1CCc2ccccc21] | 1,1-diethyl-3-(2-(indolin-1-yl)ethyl)urea |

-continued

| Compound Number | Compound Structure | Compound Name |
|---|---|---|
| UANOX003 | 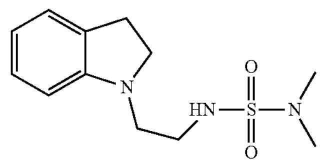 [SMILES: CN(C)S(=O)(=O)NCCN1CCc2ccccc21] | N-(N,N-dimethylaminosulfonoyl)-2-(indolin-1-yl)ethane-1-amine |
| UANOX004 | 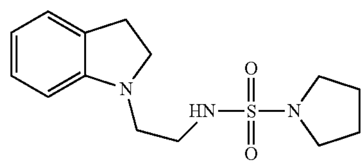 [SMILES: O=S(=O)(NCCN1CCc2ccccc21)N1CCCC1] | N-(2-(indolin-1-yl)ethyl)pyrrolidine-1-sulfonamide |
| UANOX006 | 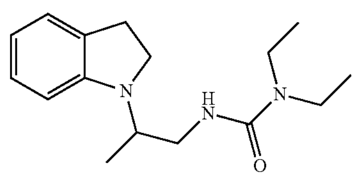 [SMILES: CCN(CC)C(=O)NCC(C)N1CCc2ccccc21] | 1,1-diethyl-3-(2-(indolin-1-yl)propyl)urea |
| UANOX007 | 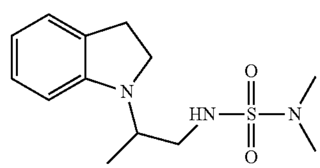 [SMILES: CC(CNS(=O)(=O)N(C)C)N1CCc2ccccc21] | N-(N,N-dimethylaminosulfonyl)-2-(indolin-1-yl)propane-1-amine |
| UANOX008 | 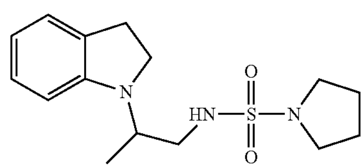 [SMILES: CC(CNS(=O)(=O)N1CCCC1)N1CCc2ccccc21] | N-(2-(indolin-1-yl)propyl)pyrrolidine-1-sulfanamide |
| UANOX009 | 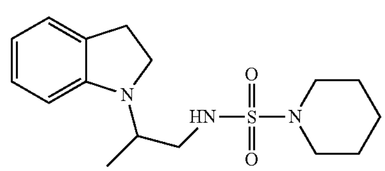 [SMILES: CC(CNS(=O)(=O)N1CCCCC1)N1CCc2ccccc21] | N-(2-(indolin-1-yl)propyl)piperidine-1-sulfonamide |
| UANOX0UAN10 | 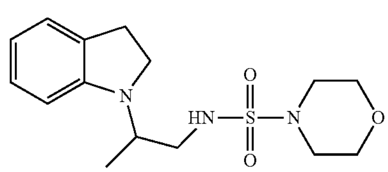 | N-(2-(indolin-1-yl)propyl)morpholine-4-sulfonamide |
| UANOX011 | 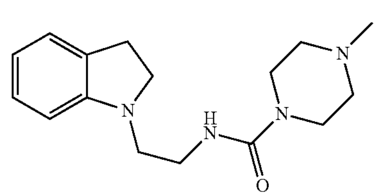 [SMILES: CN1CCN(C(=O)NCCN2CCc3ccccc32)CC1] | N-(2-(indolin-1-yl)ethyl)-4-methylpiperazine-1-carboxamide |
| UANOX012 | 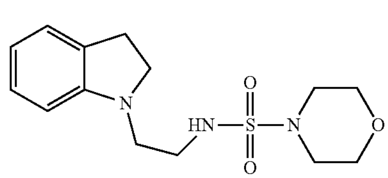 [SMILES: O=S(=O)(NCCN1CCc2ccccc21)N1CCOCC1] | N-(2-(indolin-1-yl)ethyl)morpholine-4-sulfonamide |

| Compound Number | Compound Structure | Compound Name |
|---|---|---|
| UANOX013 | 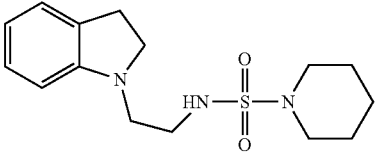 [SMILES: O=S(=O)(NCCN1CCc2ccccc21)N1CCCCC1] | N-(2-(indolin-1-yl)ethyl)piperidine-1 sulfonamide |
| UANOX017 | 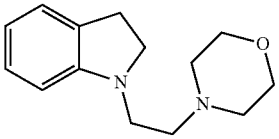 [SMILES: c1ccc2c(c1)CCN2CCN1CCOCC1] | 4-(2-(indolin-1-yl)ethyl)morpholine |
| UANOX018 | 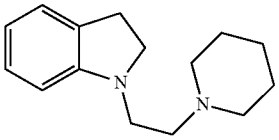 [SMILES: c1ccc2c(c1)CCN2CCN1CCCCC1] | 1-(2-(piperidin-1-yl)ethyl)indoline |
| UANOX019 | 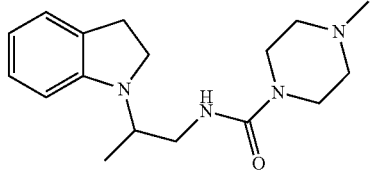 [SMILES: CC(CNC(=O)N1CCN(C)CC1)N1CCc2ccccc21] | N-(2-(indolin-1-yl)propyl)-4-methylpiperazine-1-carboxamide |
| UANOX020 | 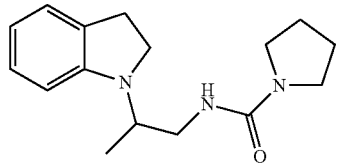 [SMILES: CC(CNC(=O)N1CCCC1)N1CCc2ccccc21] | N-(2-(indolin-1-yl)propyl)pyrrolidine-1-carboxamide |
| UANOX021 | 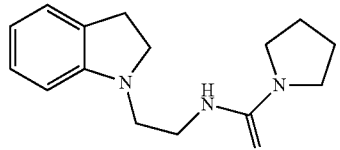 | N-(2-(indolin-1-yl)ethyl)pyrrolidine-1-carboxamide |
| UANOX0192 | 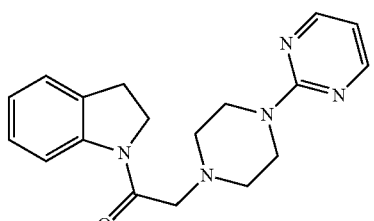 | 1-(indolin-1-yl)-2-(4-(pyrimidin-2-yl)piperazin-1-yl)ethan-1-one |
| UANOX022 | 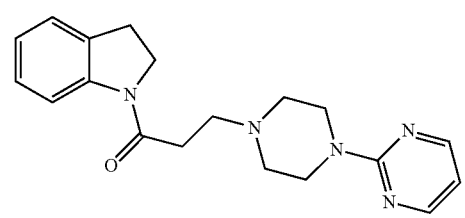 [SMILES: O=C(CCN1CCN(c2ncccn2)CC1)N1CCc2ccccc21] | 1-(indolin-1-yl)-3-(4-(pyrimidin-2-yl)piperazin-1-yl)propan-1-one |

| Compound Number | Compound Structure | Compound Name |
|---|---|---|
| UANOX023 | 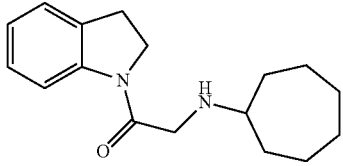 [SMILES: O=C(CNC1CCCCCC1)N1CCc2ccccc21] | 2-(cycloheptylamino)-1-(indolin-1-yl)ethan-1-one |
| UANOX024 | 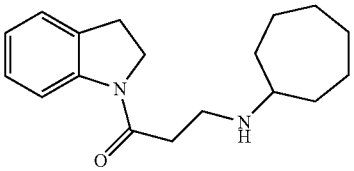 [SMILES: O=C(CCNC1CCCCCC1)N1CCc2ccccc21] | 3-(cycloheptylamino)-1-(indolin-1-yl)propan-1-one |
| UANOX025 | 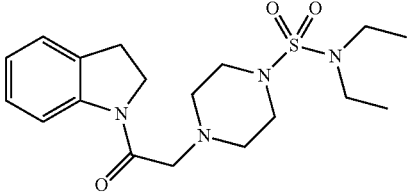 [SMILES: CCN(CC)S(=O)(=O)N1CCN(CC(=O)N2CCc3ccccc32)CC1] | N,N-diethyl-4-(2-(indolin-1-yl)-2-oxoethyl)piperazine-1-sulfonamide |
| UANOX026 | 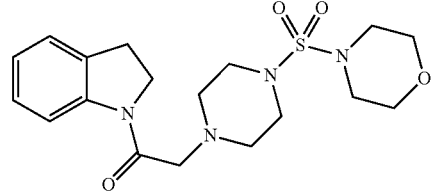 [SMILES: O=C(CN1CCN(S(=O)(=O)N2CCOCC2)CC1)N1CCc2ccccc21] | 1-(indolin-1-yl)-2-(4-(morpholinosulfonyl)piperazin-1-yl)ethan-1-one |
| UANOX027 | 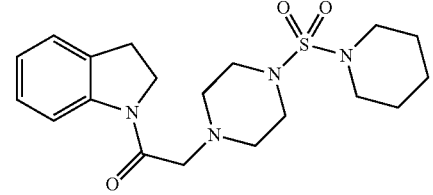 [SMILES: O=C(CN1CCN(S(=O)(=O)N2CCCCC2)CC1)N1CCc2ccccc21] | 1-(indolin-1-yl)-2-(4-(piperidin-1-ylsulfonyl)piperazin-1-yl)ethan-1-one |
| UANOX028 | 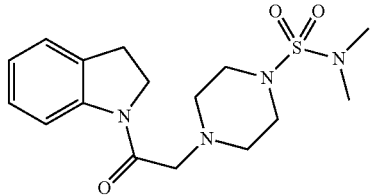 [SMILES: CN(C)S(=O)(=O)N1CCN(CC(=O)N2CCc3ccccc32)CC1] | 4-(2-(indolin-1-yl)-2-oxoethyl)-N,N-dimethylpiperazine-1-sulfonamide |
| UANOX029 | 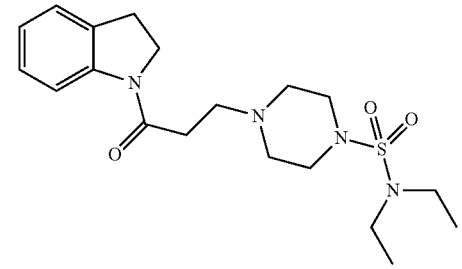 [SMILES: CCN(CC)S(=O)(=O)N1CCN(CCC(=O)N2CCc3ccccc32)CC1] | N,N-diethyl-4-(3-(indolin-1-yl)-3-oxopropyl)piperazine-1-sulfonamide |

-continued

| Compound Number | Compound Structure | Compound Name |
|---|---|---|
| UANOX030 | 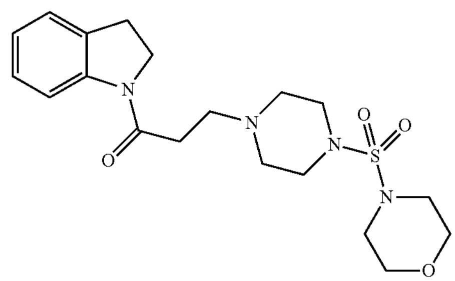 [SMILES: O=C(CCN1CCN(S(=O)(=O)N2CCOCC2)CC1)N1CCc2ccccc21] | 1-(indolin-1-yl)-3-(4-(morpholinosulfonyl)piperazin-1-yl)propan-1-one |
| UANOX031 | 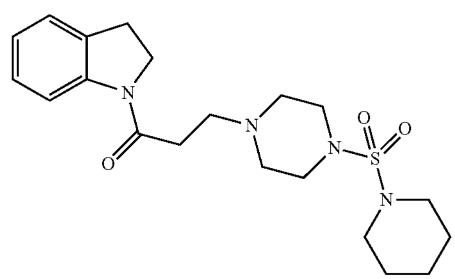 [SMILES: O=C(CCN1CCN(S(=O)(=O)N2CCCCC2)CC1)N1CCc2ccccc21] | 1-(indolin-1-yl)-3-(4-(piperidin-1-ylsulfonyl)piperazin-1-yl)propan-1-one |
| UANOX032 | 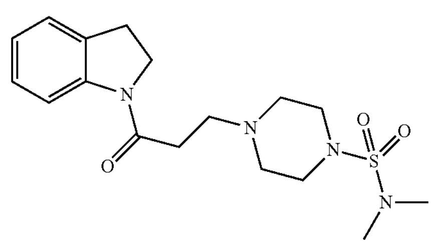 [SMILES: CN(C)S(=O)(=O)N1CCN(CCC(=O)N2CCc3ccccc32)CC1] | 4-(3-(indolin-1-yl)-3-oxopropyl)-N,N-dimethylpiperazine-1-sulfonamide |
| UANOX033 | 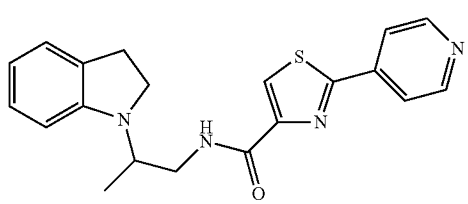 [SMILES: CC(CNC(=O)c1csc(-c2ccncc2)n1)N1CCc2ccccc21] | N-(2-(indolin-1-yl)propyl)-2-(pyridin-4-yl)thiazole-4-carboxamide |
| UANOX034 | 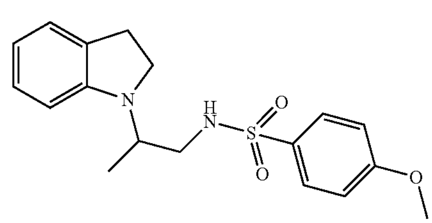 [SMILES: COc1ccc(S(=O)(=O)NCC(C)N2CCc3ccccc32)cc1] | N-(2-(indolin-1-yl)propyl)-4-methoxybenzenesulfonamide |
| UANOX035 | 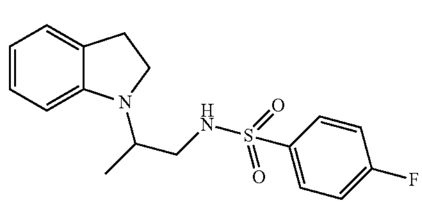 [SMILES: CC(CNS(=O)(=O)c1ccc(F)cc1)N1CCc2ccccc21] | 4-fluoro-N-(2-(indolin-1-yl)propyl)benzenesulfonamide |

-continued

| Compound Number | Compound Structure | Compound Name |
|---|---|---|
| UANOX036 | 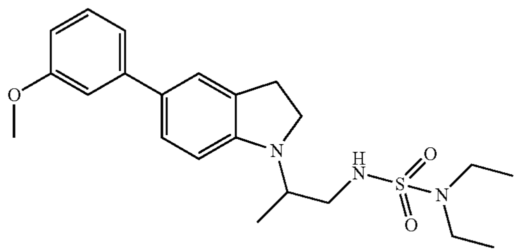 [SMILES: CCN(CC)S(=O)(=O)NCC(C)N1CCc2cc(-c3cccc(OC)c3)ccc21] | N-(2-(5-(3-methoxyphenyl)indolin-1-yl)propyl)-N,N-diethyl-1-sulfonamide |
| UANOX037 | 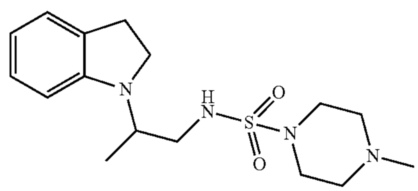 [SMILES: CC(CNS(=O)(=O)N1CCN(C)CC1)N1CCc2ccccc21] | N-(2-indolin-1-yl)propyl)-4-methylpiperazine-1-sulfonamide |
| UANOX0254 | 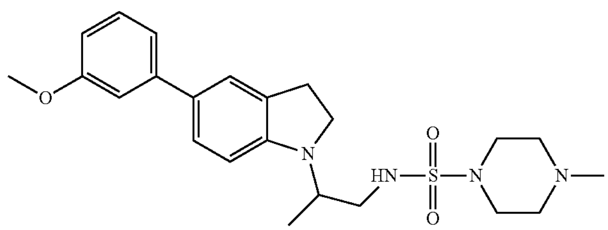 | N-(2-(5-(3-methoxyphenyl)indolin-1-yl)propyl)-4-methylpiperazine-1-sulfonamide |
| UANOX038 | 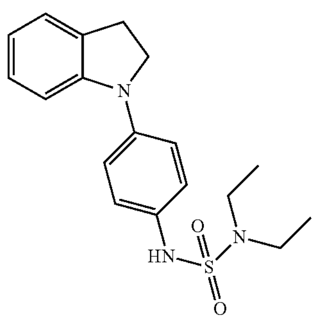 [SMILES: CCN(CC)S(=O)(=O)Nc1ccc(N2CCc3ccccc32)cc1] | N-(N,N-diethylaminosulfonyl)-4-(indolin-1-yl)-phenyl-1-amine |
| UANOX048 | 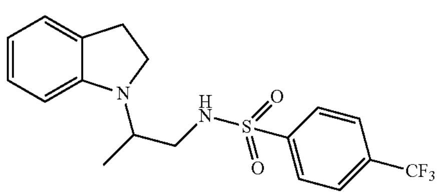 [SMILES: CC(CNS(=O)(=O)c1ccc(C(F)(F)F)cc1)N1CCc2ccccc21] | N-(2-indolin-1-yl)propyl)-4-(trifluoromethyl)benzenesulfonamide |
| UANOX049 | 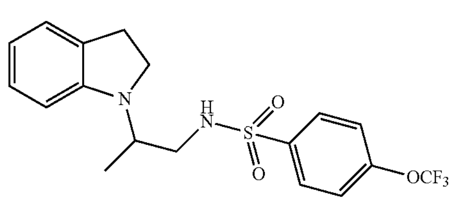 [SMILES: CC(CNS(=O)(=O)c1ccc(OC(F)(F)F)cc1)N1CCc2ccccc21] | N-(2-(indolin-1-yl)propyl)-4-(trifluoromethoxy)benzenesulfonamide |
| UANOX050 | 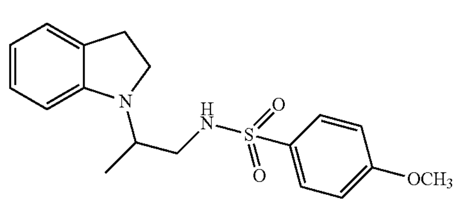 [SMILES: COc1ccc(S(=O)(=O)NCC(C)N2CCc3ccccc32)cc1] | N-(2-(indolin-1-yl)ethyl)-4-methoxybenzenesulfonamide |

-continued

| Compound Number | Compound Structure | Compound Name |
|---|---|---|
| UANOX051 | 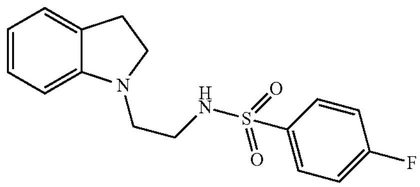 [SMILES: O=S(=O)(NCCN1CCc2ccccc21)c1ccc(F)cc1] | N-(2-(indolin-1-yl)ethyl)-4-fluorobenzene)sulfonamide |
| UANOX054 | 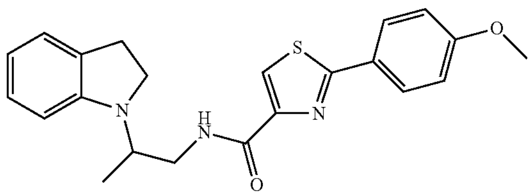 [SMILES: COc1ccc(-c2nc(C(=O)NCC(C)N3CCc4ccccc43)cs2)cc1] | N-(2-(indolin-1-yl)propyl)-2-(4-methoxyphenyl)thiazole-4-carboxamide |
| UANOX055 | 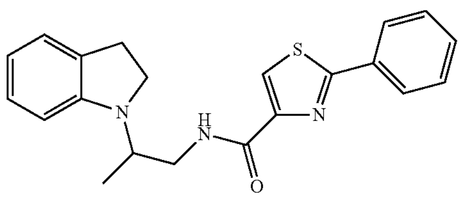 [SMILES: CC(CNC(=O)c1csc(-c2ccccc2)n1)N1CCc2ccccc21] | N-(2-(indolin-1-yl)propyl)-2-phenylthiazole-4-carboxamide |
| UANOX056 | 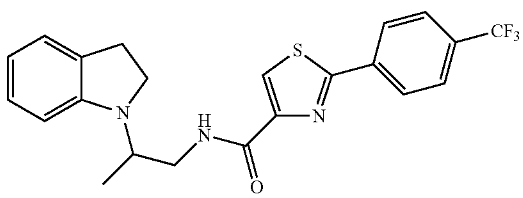 [SMILES: CC(CNC(=O)c1csc(-c2ccc(C(F)(F)F)cc2)n1)N1CCc2ccccc21] | N-(2-(indolin-1-yl)propyl)-2-(4-(trifluoromethyl)phenyl)thiazole-4-carboxamide |
| UANOX062 | 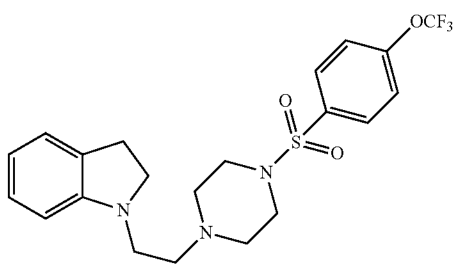 [SMILES: O=S(=O)(c1ccc(OC(F)(F)F)cc1)N1CCN(CCN2CCc3ccccc32)CC1] | 1-(2-(4-((4-(trifluoromethoxy)phenyl)sulfonyl)piperazin-1-yl)ethyl)indoline |
| UANOX063 | 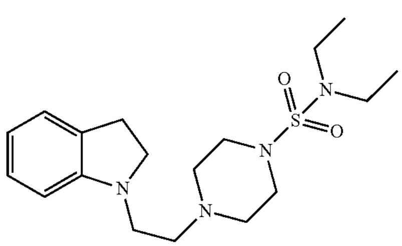 [SMILES: CCN(CC)S(=O)(=O)N1CCN(CCN2CCc3ccccc32)CC1] | N,N-diethyl-4-(2-(indolin-1-yl)ethyl)piperazine-1-sulfonamide |

-continued

| Compound Number | Compound Structure | Compound Name |
| --- | --- | --- |
| UANOX064 | 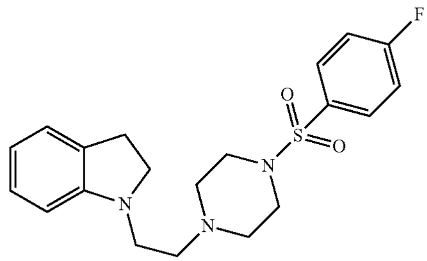 [SMILES: O=S(=O)(c1ccc(F)cc1)N1CCN(CCN2CCc3ccccc32)CC1] | 1-(2-(4-((4-fluorophenyl)sulfonyl)piperazin-1-yl)ethyl)indoline |
| UANOX066 | 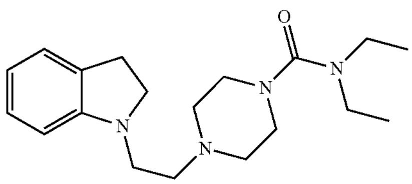 [SMILES: CCN(CC)C(=O)N1CCN(CCN2CCc3ccccc32)CC1] | N,N-diethyl-4-(2-(indolin-1-yl)ethyl)piperazine-1-carboxamide |
| UANOX067 | 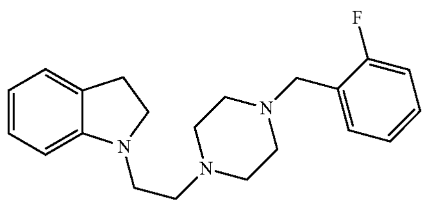 [SMILES: Fc1ccccc1CN1CCN(CCN2CCc3ccccc32)CC1] | 1-(2-(4-(2-fluorobenzyl)piperazine-1-yl)ethyl)indoline |
| UANOX069 | 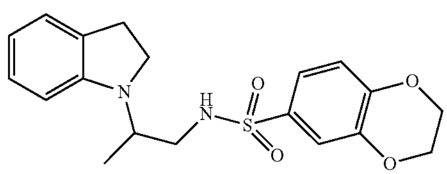 [SMILES: CC(CNS(=O)(=O)c1ccc2c(c1)OCCO2)N1CCc2ccccc21] | N-(2-(indolin-1-yl)propyl)-2,3-dihydrobenzo[b][1,4]dioxine-6-sulfonamide |
| UANOX070 | 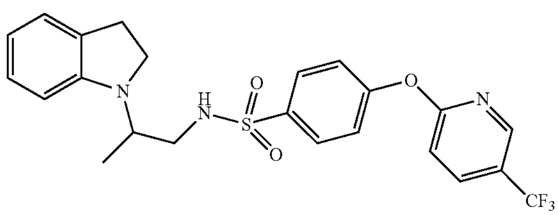 [SMILES: CC(CNS(=O)(=O)c1ccc(Oc2ccc(C(F)(F)F)cn2)cc1)N1CCc2ccccc21] | N-(2-(indolin-1-yl)propyl)-4-((5-(trifluoromethyl)pyridin-2-yl)oxy)benzenesulfonamide |
| UANOX071 | 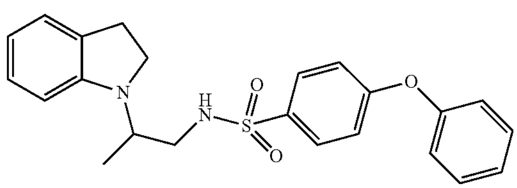 [SMILES: CC(CNS(=O)(=O)c1ccc(Oc2ccccc2)cc1)N1CCc2ccccc21] | N-(2-(indolin-1-yl)propyl)-4-phenoxybenzenesulfonamide |
| UANOX072 | 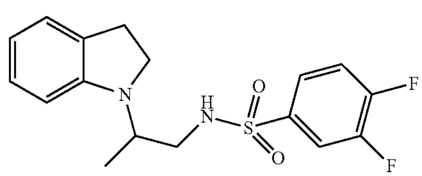 [SMILES: CC(CNS(=O)(=O)c1ccc(F)c(F)c1)N1CCc2ccccc21] | 3,4-difluoro-N-(2-(indolin-1-yl)propyl)benzenesulfonamide |
| UANOX073 | 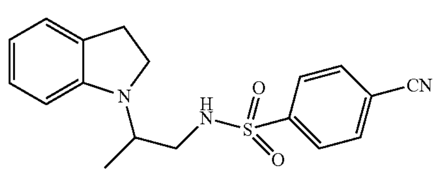 [SMILES: CC(CNS(=O)(=O)c1ccc(C#N)cc1)N1CCc2ccccc21] | 4-cyano-N-(2-indolin-1-yl)propyl)benzenesulfonamide |

-continued

| Compound Number | Compound Structure | Compound Name |
|---|---|---|
| UANOX075 | 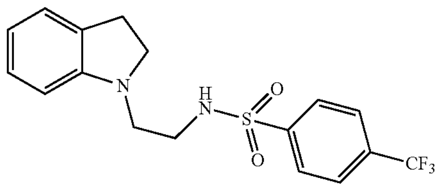 [SMILES: O=S(=O)(NCCN1CCc2ccccc21)c1ccc(C(F)(F)F)cc1] | N-(2-indolin-1-yl)ethyl)-4-(trifluoromethyl)benzenesulfonamide |
| UANOX076 | 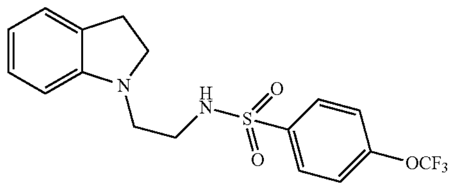 [SMILES: O=S(=O)(NCCN1CCc2ccccc21)c1ccc(OC(F)(F)F)cc1] | N-(2-indolin-1-yl)ethyl)-4-(trifluoromethoxy)benzenesulfonamide |
| UANOX077 | 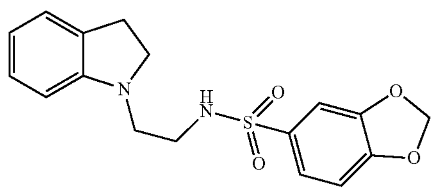 [SMILES: O=S(=O)(NCCN1CCc2ccccc21)c1ccc2c(c1)OCO2] | N-(2-(indolin-1-yl)ethyl)benzo[d][1,3]dioxole-5-sulfonamide |
| UANOX078 | 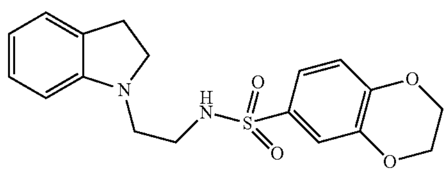 [SMILES: O=S(=O)(NCCN1CCc2ccccc21)c1ccc2c(c1)OCCO2] | N-(2-indolin-1-yl)ethyl)-2,3-dihydrobenzo[b][1,4]dioxine-6-sulfonamide |
| UANOX079 | 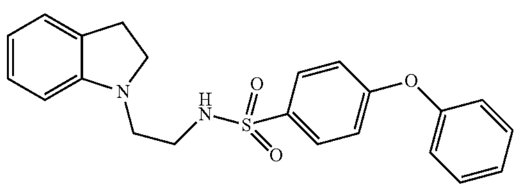 [SMILES: O=S(=O)(NCCN1CCc2ccccc21)c1ccc(Oc2ccccc2)cc1] | N-(2-indolin-1-yl)ethyl)-4-phenoxybenzenesulfonamide |
| UANOX080 | 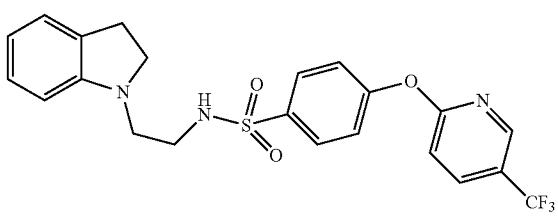 | N-(2-indolin-1-yl)ethyl)-4-((5-(trifluoromethyl)pyridin-2-yl)oxy)benzenesulfonamide |
| UANOX081 | 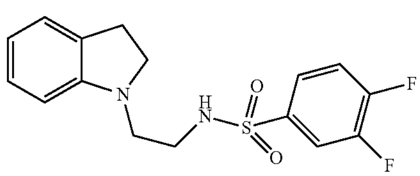 [SMILES: O=S(=O)(NCCN1CCc2ccccc21)c1ccc(F)c(F)c1] | 3,4-difluoro-N-(2-(indolin-1-yl)ethyl)benzenesulfonamide |
| UANOX082 | 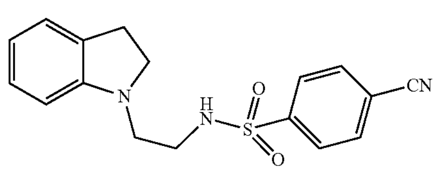 [SMILES: N#Cc1ccc(S(=O)(=O)NCCN2CCc3ccccc32)cc1] | 4-cyano-N-(2-(indolin-1-yl)ethyl)benzenesulfonamide |

-continued

| Compound Number | Compound Structure | Compound Name |
|---|---|---|
| UANOX083 | 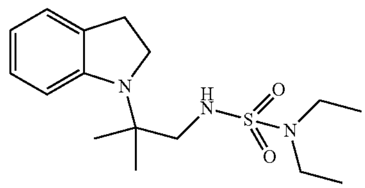 [SMILES: CCN(CC)S(=O)(=O)NCC(C)(C)N1CCc2ccccc21] | N-(N,N-diethylaminosulfonyl)-2-(indolin-1-yl)-2-methylpropane-1-amine |
| UANOX084 | 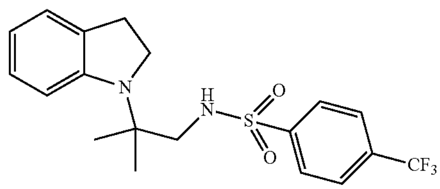 [SMILES: CC(C)(CNS(=O)(=O)c1ccc(C(F)(F)F)cc1)N1CCc2ccccc21] | N-(2-indolin-1-yl)-2-methylpropyl)-4-(trifluoromethyl)benzenesulfonamide |
| UANOX085 | 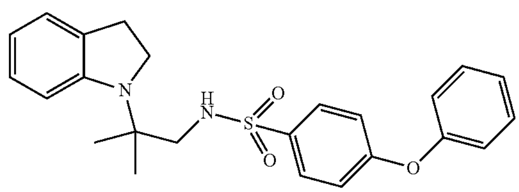 [SMILES: CC(C)(CNS(=O)(=O)c1ccc(Oc2ccccc2)cc1)N1CCc2ccccc21] | N-(2-indolin-1-yl)-2-methylpropyl)-4-phenoxybenzenesulfonamide |
| UANOX086 | 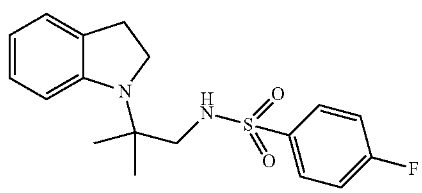 [SMILES: CC(C)(CNS(=O)(=O)c1ccc(F)cc1)N1CCc2ccccc21] | 4-fluoro-N-(2-(indolin-1-yl)-2-methylpropyl)benzenesulfonamide |
| UANOX087 | 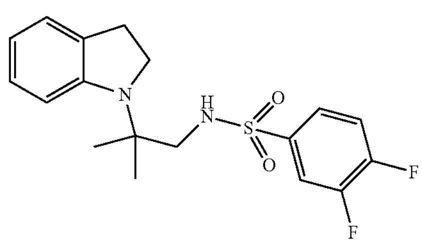 [SMILES: CC(C)(CNS(=O)(=O)c1ccc(F)c(F)c1)N1CCc2ccccc21] | 3,4-difluoro-N-(2-indolin-1-yl)-2-methylpropyl)benzenesulfonamide |
| UANOX088 | 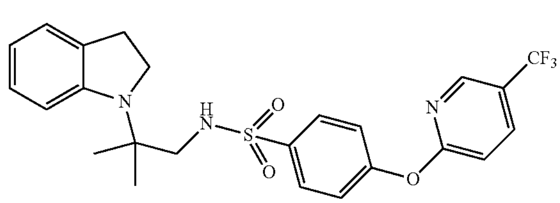 [SMILES: CC(C)(CNS(=O)(=O)c1ccc(Oc2ccc(C(F)(F)F)cn2)cc1)N1CCc2ccccc21] | N-(2-indolin-1-yl)-2-methylpropyl)-4-((5-(trifluoromethyl)pyridin-2-yl)oxy)benzenesulfonamide |
| UANOX089 | 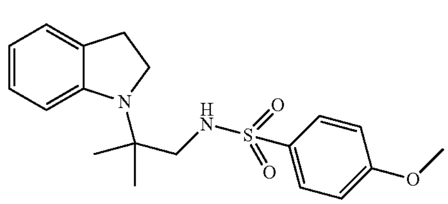 [SMILES: COc1ccc(S(=O)(=O)NCC(C)(C)N2CCc3ccccc32)cc1] | N-(2-indolin-1-yl)-2-methylpropyl)-4-(methoxy)benzenesulfonamide |

| Compound Number | Compound Structure | Compound Name |
|---|---|---|
| UANOX090 | 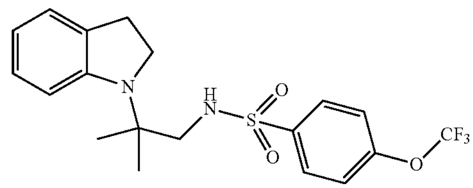 [SMILES: CC(C)(CNS(=O)(=O)c1ccc(OC(F)(F)F)cc1)N1CCc2ccccc21] | N-(2-indolin-1-yl)-2-methylpropyl)-4-(trifluoromethyl)benzenesulfonamide |

In some embodiments, the invention provide compounds of the formula

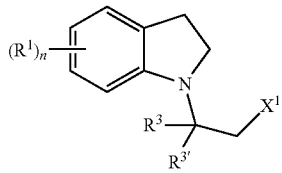

(Ia)

wherein
n is 0 or 1;
$R^1$ is optionally substituted aryl;
$X^1$ is —$NR^4R^5$, —$NR^bC(O)R^6$, —$NR^bSO_2NR^4R^5$ or —$NR^bSO_2R^6$;
$R^3$ and $R^{3'}$ are each independently hydrogen or alkyl;
each of $R^4$ and $R^5$ is independently hydrogen or alkyl, or $R^4$ and $R^5$ together with the nitrogen atom to which they are attached to form an optionally substituted heterocycloalkyl;
$R^b$ is hydrogen or alkyl; and
$R^6$ is optionally substituted aryl or optionally substituted heterocyclyl.

In some embodiments, the compounds are of formula (Ia), wherein
$X^1$ is —$NR^4R^5$, —$NHC(O)R^6$, —$NHSO_2NR^4R^5$ or —$NHSO_2R^6$;
$R^3$ and $R^{3'}$ are each independently hydrogen or methyl;
$R^{4'}$ and $R^5$ are alkyl,
or $R^4$ and $R^5$ together with the nitrogen atom to which they are attached to form an optionally substituted piperazine ring; and
$R^6$ is optionally substituted phenyl or optionally substituted pyrolidinyl.

In some embodiments, the compounds are of formula (Ia), wherein
$X^1$ is —$NR^4R^5$, —$NHC(O)R^6$, —$NHSO_2NR^4R^5$ or —$NHSO_2R^6$;
$R^3$ and $R^{3'}$ are each independently hydrogen or methyl;
$R^4$ and $R^5$ are ethyl,
or $R^4$ and $R^5$ together with the nitrogen atom to which they are attached to form an optionally substituted piperazine ring; and
$R^6$ is optionally substituted phenyl or optionally substituted pyrolidinyl.

In some embodiments, the compounds are of formula (Ia), wherein
n is 1;
$R^1$ is 3-methoxyphenyl; and
$R^4$ and $R^5$ are ethyl.

In some embodiments, the compounds are of formula (Ia), wherein
n is 0;
$R^4$ and $R^5$ together with the nitrogen atom to which they are attached to form piperazine ring substituted with $R^7$, wherein $R^7$ is alkyl —$SO_2R^{12}$ or —$SO_2NR^8R^9$, wherein
$R^8$ and $R^9$ are alkyl,
$R^{12}$ is optionally substituted aryl; and
$R^6$ is phenyl or pyrolidinyl, wherein the phenyl is substituted with one or more of halogen, haloalkyl, —O-haloalkyl, —O-(5-(trifluoromethyl)pyridin-2-yl), —O-phenyl, cyano, -4-methoxyphenyl.

In some embodiments, the compounds are of formula (Ia), wherein $R^3$ and $R^{3'}$ are hydrogen.

In some embodiments, the compounds are of formula (Ia), wherein $R^3$ is hydrogen and $R^3$ is methyl.

In some embodiments, the compounds are of formula (Ia), wherein wherein $R^3$ and $R^{3'}$ are methyl.

In some embodiments, the compounds are of formula (Ib)

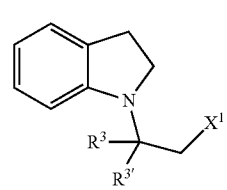

(Ib)

wherein
$X^1$ is —$NR^4R^5$, —$NHC(O)R^6$, —$NHSO_2NR^4R^5$ or —$NHSO_2R^6$;
$R^3$ and $R^{3'}$ are each independently hydrogen or methyl;
when $X^1$ is —$NR^4R^5$, $R^4$ and $R^5$ together with the nitrogen atom to which they are attached to form a piperazine ring, wherein the piperazine ring substituted with $R^7$, wherein $R^7$ is —$SO_2R^{12}$ or —$SO_2NR^8R^9$, wherein $R^8$ and $R^9$ are alkyl; and
$R^{12}$ is phenyl substituted with halogen or —O-haloalkyl,
when $X^1$ is —$NHC(O)R^6$, $R^6$ is pyrrolidinyl,
when $X^1$ is —$NHSO_2NR^4R^5$, wherein $R^4$ and $R^5$ are alkyl, and
when $X^1$ is —$NHSO_2R^6$, $R^6$ is phenyl substituted with one or more of —O-alkyl, halogen, haloalkyl, —O-haloalkyl, —O-(5-(trifluoromethyl)pyridin-2-yl), —O-phenyl or cyano;
provided that
a) when $R^6$ is phenyl substituted with —O-alkyl, both $R^3$ and $R^{3'}$ are methyl;

b) when $R^6$ is phenyl substituted with one halogen, both $R^3$ and $R^{3'}$ are methyl;
c) when $R^6$ is phenyl substituted with two halogens, both $R^3$ and $R^{3'}$ are hydrogen, or both $R^3$ and $R^{3'}$ are methyl;
d) when $X^1$ is —NHSO$_2$NR$^4$R$^5$, wherein $R^4$ and $R^5$ are alkyl, both $R^3$ and $R^{3'}$ are methyl.

In some embodiments, the compounds are of formula (Ib), wherein
$X^1$ is —NR$^4$R$^5$, —NHC(O)R$^6$, —NHSO$_2$NR$^4$R$^5$ or —NHSO$_2$R$^6$;
$R^3$ and $R^{3'}$ are each independently hydrogen or methyl;
when $X^1$ is —NR$^4$R$^5$, $R^4$ and $R^5$ together with the nitrogen atom to which they are attached to form a piperazine ring, wherein the piperazine ring substituted with $R^7$, wherein $R^7$ is —SO$_2$R$^{12}$ or —SO$_2$NR$^8$R$^9$, wherein $R^8$ and $R^9$ are ethyl; and
$R^{12}$ is phenyl substituted with fluoro or —O—CF$_3$,
when $X^1$ is —NHC(O)R$^6$, $R^6$ is pyrrolidinyl,
when $X^1$ is —NHSO$_2$NR$^4$R$^5$, wherein $R^4$ and $R^5$ are ethyl, and
when $X^1$ is —NHSO$_2$R$^6$, $R^6$ is phenyl substituted with one or more of —O-Me, fluoro, —CF$_3$, —O—CF$_3$, —O-(5-(trifluoromethyl)pyridin-2-yl), —O-phenyl or cyano;
provided that
a) when $R^6$ is phenyl substituted with —OMe, both $R^3$ and $R^{3'}$ are methyl;
b) when $R^6$ is phenyl substituted with one fluoro group, both $R^3$ and $R^{3'}$ are methyl;
c) when $R^6$ is phenyl substituted with two fluoro groups, both $R^3$ and $R^{3'}$ are hydrogen, or both $R^3$ and $R^{3'}$ are methyl; and
d) when $X^1$ is —NHSO$_2$NR$^4$R$^5$, wherein $R^4$ and $R^5$ are ethyl, both $R^3$ and $R^{3'}$ are methyl.

In some embodiments, the compounds are of formula (Ib), wherein
$X^1$ is —NR$^4$R$^5$ or —NHSO$_2$R$^6$;
$R^3$ and $R^{3'}$ are each independently hydrogen or methyl;
$R^4$ and $R^5$ together with the nitrogen atom to which they are attached to form a piperazine ring, wherein the piperazine ring substituted with $R^7$, wherein $R^7$ is —SO$_2$R$^{12}$ or —SO$_2$NR$^8$R$^9$, wherein $R^8$ and $R^9$ are alkyl; and
$R^{12}$ is phenyl substituted with halogen or —O-haloalkyl, and
$R^6$ is phenyl substituted with one or more of —O-alkyl, halogen, haloalkyl, —O— haloalkyl, —O-(5-(trifluoromethyl)pyridin-2-yl), —O-phenyl or cyano;
provided that
a) when $R^6$ is phenyl substituted with —O-alkyl, both $R^3$ and $R^{3'}$ are methyl;
b) when $R^6$ is phenyl substituted with one halogen, both $R^3$ and $R^{3'}$ are methyl; and
c) when $R^6$ is phenyl substituted with two halogens, both $R^3$ and $R^{3'}$ are hydrogen, or both $R^3$ and $R^{3'}$ are methyl.

In some embodiments, the compounds are of formula (Ib), wherein
$X^3$ is —NR$^4$R$^5$ or —NHSO$_2$R$^6$;
$R^3$ and $R^{3'}$ are each independently hydrogen or methyl;
$R^4$ and $R^5$ together with the nitrogen atom to which they are attached to form a piperazine ring, wherein the piperazine ring substituted with $R^7$, wherein $R^7$ is —SO$_2$R$^{12}$ or —SO$_2$NR$^8$R$^9$, wherein $R^8$ and $R^9$ are ethyl; and
$R^{12}$ is phenyl substituted with fluoro or —O—CF$_3$, and $R^6$ is phenyl substituted with one or more of —O-Me, fluoro, —CF$_3$, —O—CF$_3$, —O-(5-(trifluoromethyl)pyridin-2-yl), —O-phenyl or cyano;
provided that
a) when $R^6$ is phenyl substituted with —OMe, both $R^3$ and $R^{3'}$ are methyl;
b) when $R^6$ is phenyl substituted with one fluoro group, both $R^3$ and $R^{3'}$ are methyl;
c) when $R^6$ is phenyl substituted with two fluoro groups, both $R^3$ and $R^{3'}$ are hydrogen, or both $R^3$ and $R^{3'}$ are methyl.

In some embodiments, the compounds are of formula (Ib), wherein
$X^1$ is —NR$^4$R$^5$;
$R^3$ and $R^{3'}$ are each independently hydrogen or methyl;
$R^4$ and $R^5$ together with the nitrogen atom to which they are attached to form a piperazine ring, wherein the piperazine ring substituted with $R^7$, wherein $R^7$ is —SO$_2$R$^{12}$ or —SO$_2$NR$^8$R$^9$, wherein
$R^8$ and $R^9$ are alkyl; and
$R^{12}$ is phenyl substituted with halogen or —O-haloalkyl,
provided that
a) when $R^6$ is phenyl substituted with —O-alkyl, both $R^3$ and $R^{3'}$ are methyl;
b) when $R^6$ is phenyl substituted with one halogen, both $R^3$ and $R^{3'}$ are methyl; and
c) when $R^6$ is phenyl substituted with two halogens, both $R^3$ and $R^{3'}$ are hydrogen, or both $R^3$ and $R^{3'}$ are methyl.

In some embodiments, the compounds are of formula (Ib), wherein
$X^1$ is —NR$^4$R$^5$;
$R^3$ and $R^{3'}$ are each independently hydrogen or methyl;
$R^4$ and $R^5$ together with the nitrogen atom to which they are attached to form a piperazine ring, wherein the piperazine ring substituted with $R^7$, wherein $R^7$ is —SO$_2$R$^{12}$ or —SO$_2$NR$^8$R$^9$, wherein
$R^8$ and $R^9$ are ethyl; and
$R^{12}$ is phenyl substituted with fluoro or —O—CF$_3$.

In some embodiments, the compounds are of formula (Ib), wherein
$X^1$ is —NHSO$_2$R$^6$;
$R^3$ and $R^{3'}$ are each independently hydrogen or methyl; and
$R^6$ is phenyl substituted with one or more of —O-alkyl, halogen, haloalkyl, —O— haloalkyl, —O-(5-(trifluoromethyl)pyridin-2-yl), —O-phenyl or cyano;
provided that
a) when $R^6$ is phenyl substituted with —O-alkyl, both $R^3$ and $R^{3'}$ are methyl;
b) when $R^6$ is phenyl substituted with one halogen, both $R^3$ and $R^{3'}$ are methyl; and
c) when $R^6$ is phenyl substituted with two halogens, both $R^3$ and $R^{3'}$ are hydrogen, or both $R^3$ and $R^{3'}$ are methyl.

In some embodiments, the compounds are of formula (Ib), wherein
$X^1$ is —NHSO$_2$R$^6$;
$R^3$ and $R^{3'}$ are each independently hydrogen or methyl;
$R^6$ is phenyl substituted with one or more of —O-Me, fluoro, —CF$_3$, —O—CF$_3$, —O-(5-(trifluoromethyl)pyridin-2-yl), —O-phenyl or cyano;
provided that
a) when $R^6$ is phenyl substituted with —OMe, both $R^3$ and $R^{3'}$ are methyl;

b) when $R^6$ is phenyl substituted with one fluoro group, both $R^3$ and $R^{3'}$ are methyl;
c) when $R^6$ is phenyl substituted with two fluoro groups, both $R^3$ and $R^{3'}$ are hydrogen, or both $R^3$ and $R^{3'}$ are methyl.

In some embodiments, the compounds are of formula (Ib), wherein
$X^1$ is —NHC(O)$R^6$ or —NHSO$_2$NR$^4$R$^5$;
$R^3$ and $R^{3'}$ are each independently hydrogen or methyl;
$R^6$ is pyrrolidinyl; and
when $X^1$ is —NHSO$_2$NR$^4$R$^5$, wherein $R^4$ and $R^5$ are alkyl;
provided that
a) when $R^4$ and $R^5$ are alkyl, both $R^3$ and $R^{3'}$ are methyl.

In some embodiments, the compounds are of formula (Ib), wherein
$X^1$ is —NHC(O)$R^6$ or —NHSO$_2$NR$^4$R$^5$;
$R^3$ and $R^{3'}$ are each independently hydrogen or methyl;
$R^6$ is pyrrolidinyl; and
when $X^1$ is —NHSO$_2$NR$^4$R$^5$, wherein $R^4$ and $R^5$ are ethyl;
provided that
a) when $R^4$ and $R^5$ are ethyl, both $R^3$ and $R^{3'}$ are methyl.

In some embodiments, the compounds are of formula (Ib), wherein
$X^1$ is —NR$^4$R$^5$, —NHC(O)$R^6$ or —NHSO$_2$R$^6$;
$R^3$ is hydrogen and $R^{3'}$ is hydrogen or methyl;
when $X^1$ is —NR$^4$R$^5$, $R^4$ and $R^5$ together with the nitrogen atom to which they are attached to form a piperazine ring, wherein the piperazine ring substituted with $R^7$, wherein $R^7$ is —SO$_2$R$^{12}$ or —SO$_2$NR$^8$R$^9$, wherein $R^8$ and $R^9$ are alkyl; and
$R^{12}$ is phenyl substituted with halogen or —O—haloalkyl,
when $X^1$ is —NHC(O)$R^6$, $R^6$ is pyrrolidinyl,
when $X^1$ is —NHSO$_2$R$^6$, $R^6$ is phenyl substituted with haloalkyl, —O-haloalkyl, —O-(5-(trifluoromethyl)pyridin-2-yl), —O-phenyl or cyano.

In some embodiments, the compounds are of formula (Ib), wherein
$X^1$ is —NR$^4$R$^5$, —NHC(O)$R^6$ or —NHSO$_2$R$^6$;
$R^3$ is hydrogen and $R^{3'}$ is hydrogen or methyl;
when $X^1$ is —NR$^4$R$^5$, $R^4$ and $R^5$ together with the nitrogen atom to which they are attached to form a piperazine ring, wherein the piperazine ring substituted with $R^7$, wherein $R^7$ is —SO$_2$R$^{12}$ or —SO$_2$NR$^8$R$^9$, wherein $R^8$ and $R^9$ are ethyl; and
$R^{12}$ is phenyl substituted with fluoro or —O—CF$_3$,
when $X^1$ is —NHC(O)$R^6$, $R^6$ is pyrrolidinyl,
when $X^1$ is —NHSO$_2$R$^6$, $R^6$ is phenyl substituted with —CF$_3$, —O—CF$_3$, —O-(5-(trifluoromethyl)pyridin-2-yl), —O-phenyl or cyano.

In some embodiments, the compounds are of formula (Ib), wherein
$X^1$ is —NR$^4$R$^5$ or —NHSO$_2$R$^6$;
$R^3$ is hydrogen and $R^{3'}$ is hydrogen or methyl;
when $X^1$ is —NR$^4$R$^5$, $R^4$ and $R^5$ together with the nitrogen atom to which they are attached to form a piperazine ring, wherein the piperazine ring substituted with $R^7$, wherein $R^7$ is —SO$_2$R$^{12}$ or —SO$_2$NR$^8$R$^9$, wherein $R^8$ and $R^9$ are alkyl; and
$R^{12}$ is phenyl substituted with halogen or —O-haloalkyl,
when $X^1$ is —NHSO$_2$R$^6$, $R^6$ is phenyl substituted with haloalkyl, —O-haloalkyl, —O-(5-(trifluoromethyl)pyridin-2-yl), —O-phenyl or cyano.

In some embodiments, the compounds are of formula (Ib), wherein
$X^1$ is —NR$^4$R$^5$ or —NHSO$_2$R$^6$;
$R^3$ is hydrogen and $R^{3'}$ is hydrogen or methyl;
when $X^1$ is —NR$^4$R$^5$, $R^4$ and $R^5$ together with the nitrogen atom to which they are attached to form a piperazine ring, wherein the piperazine ring substituted with $R^7$, wherein $R^7$ is —SO$_2$R$^{12}$ or —SO$_2$NR$^8$R$^9$, wherein $R^8$ and $R^9$ are ethyl; and
$R^{12}$ is phenyl substituted with fluoro or —O—CF$_3$,
when $X^1$ is —NHSO$_2$R$^6$, $R^6$ is phenyl substituted with haloalkyl, —O-haloalkyl, —O-(5-(trifluoromethyl)pyridin-2-yl), —O-phenyl or cyano.

In some embodiments, the compounds are of formula (Ib), wherein
$X^1$ is —NR$^4$R$^5$;
$R^3$ is hydrogen and $R^{3'}$ is hydrogen or methyl;
$R^4$ and $R^5$ together with the nitrogen atom to which they are attached to form a piperazine ring, wherein the piperazine ring substituted with $R^7$, wherein $R^7$ is —SO$_2$R$^{12}$ or —SO$_2$NR$^8$R$^9$, wherein $R^8$ and $R^9$ are alkyl; and
$R^{12}$ is phenyl substituted with halogen or —O-haloalkyl.

In some embodiments, the compounds are of formula (Ib), wherein
$X^1$ is —NR$^4$R$^5$;
$R^3$ is hydrogen and $R^{3'}$ is hydrogen or methyl;
NR$^4$R$^5$, $R^4$ and $R^5$ together with the nitrogen atom to which they are attached to form a piperazine ring, wherein the piperazine ring substituted with $R^7$, wherein $R^7$ is —SO$_2$R$^{12}$ or —SO$_2$NR$^8$R$^9$, wherein $R^8$ and $R^9$ are ethyl; and
$R^{12}$ is phenyl substituted with fluoro or —O—CF$_3$.

In some embodiments, the compounds are of formula (Ib), wherein
$X^1$ is —NHSO$_2$R$^6$;
$R^3$ is hydrogen and $R^{3'}$ is hydrogen or methyl;
$R^6$ is phenyl substituted with haloalkyl, —O-haloalkyl, —O-(5-(trifluoromethyl)pyridin-2-yl), —O-phenyl or cyano.

In some embodiments, the compounds are of formula (Ib), wherein
$X^1$ is —NHSO$_2$R$^6$;
$R^3$ is hydrogen and $R^{3'}$ is hydrogen or methyl;
$R^6$ is phenyl substituted with haloalkyl, —O-haloalkyl, —O-(5-(trifluoromethyl)pyridin-2-yl), —O-phenyl or cyano.

In some embodiments, the compounds are of formula (Ib), wherein
$X^1$ is —NHSO$_2$R$^6$;
$R^3$ and $R^{3'}$ are methyl;
$R^6$ is phenyl substituted with one or more of —O-alkyl, halogen, haloalkyl, —O— haloalkyl, —O-(5-(trifluoromethyl)pyridin-2-yl), —O-phenyl or cyano.

In some embodiments, the compounds are of formula (Ib), wherein
$X^1$ is —NHSO$_2$R$^6$;
$R^3$ and $R^{3'}$ are methyl;
$R^6$ is phenyl substituted with one or more of —OMe, fluoro, —CF$_3$, —O—CF$_3$, —O-(5-(trifluoromethyl)pyridin-2-yl), —O-phenyl or cyano.

In some embodiments, the compound is
N—(N,N-diethylaminosulfonyl)-2-(indolin-1-yl)ethane-1-amine
N-(2-(indolin-1-yl)ethyl)pyrrolidine-1-sulfonamide
1,1-diethyl-3-(2-(indolin-1-yl)propyl)urea N—(N,N-dimethylaminosulfonyl)-2-(indolin-1-yl)propane-1-amine
N-(2-(indolin-1-yl)propyl)pyrrolidine-1-sulfonamide
N-(2-(indolin-1-yl)ethyl)-4-methylpiperazine-1-carboxamide
N-(2-(indolin-1-yl)ethyl)morpholine-4-sulfonamide
N-(2-(indolin-1-yl)ethyl)piperidine-1-sulfonamide
N-(2-(indolin-1-yl)propyl)-4-methylpiperazine-1-carboxamide
N-(2-(indolin-1-yl)propyl)pyrrolidine-1-carboxamide
N-(2-(indolin-1-yl)ethyl)pyrrolidine-1-carboxamide
1-(indolin-1 yl)-2-(4-(pyrimidin-2-yl)piperazin-1-yl)ethan-1-one
1-(indolin-1-yl)-2-(4-(piperidin-1-ylsulfonyl)piperazin-1-yl)ethan-1-one
4-(2-(indolin-1-yl)-2-oxoethyl)-N,N-di methylpiperazine-1-sulfonamide
1-(indolin-1-yl)-3-(4-(piperidin-1-ylsulfonyl)piperazin-1-yl)propan-1-one
N-(2-(indolin-1-yl)propyl)-2-(pyridin-4-yl)thiazole-4-carboxamide
N-(2-(indolin-1-yl)propyl)-4-methoxybenzenesulfonamide
N-(2-(5-(3-methoxyphenyl)indolin-1-yl)propyl)-N,N-diethyl-1-sulfonamide
N-(2-(indolin-1-yl)propyl)-4-methylpiperazine-1-sulfonamide
N-(2-(5-(3-methoxyphenyl)indolin-1-yl)propyl)-4-methylpiperazine-1-sulfonamide
N—(N N-diethylaminosulfonyl)-4-(indolin-1-yl)-phenyl-1-amine
N-(2-(indolin-1-yl)propyl)-4-(trifluoromethyl)benzenesulfonamide
N-(2-(indolin-1-yl)propyl)-4-(trifluoromethoxy)benzenesulfonamide
N-(2-(indolin-1-yl)propyl)-2-(4-methoxy phenyl)thiazole-4-carboxamide
N-(2-(indolin-1-yl)propyl)-2-phenylthiazole-4-carboxamide
N-(2-(indol in-1-yl)propyl)-2-(4-(trifluoromethyl)phenyl)thiazole-4-carboxamide
1-(2-(4-((4-(trifluoromethoxy)phenyl)sulfonyl)piperazin-1-yl)ethyl)indoline
N,N-diethyl-4-(2-(indolin-1-yl)ethyl)piperazine-1-sulfonamide
1-(2-(4-((4-fluorophenyl)sulfonyl)piperazin-1-yl)ethyl)indoline
N,N-diethyl-4-(2-(indolin-1-yl)ethyl)piperazine-1-carboxamide
1-(2-(4-(2-fluorobenzyl)piperazin-1-yl)ethyl)indoline
N-(2-(indolin-1-yl)propyl)-4-((5-(trifluoromethyl)pyridin-2-yl)oxy)benzenesulfonamide
N-(2-(indolin-1-yl)propyl)-4-phenoxybenzenesulfonamide
4-cyano-N-(2-(indolin-1-yl)propyl)benzenesulfonamide
N-(2-(indolin-1-yl)ethyl)-4-(trifluoromethyl)benzenesulfonamide
N-(2-(indolin-1-yl)ethyl)-4-(trifluoromethoxy)benzenesulfonamide
N-(2-(indol in-1-yl)ethyl)-4-phenoxybenzenesulfonamide
N-(2-(indolin-1-yl)ethyl)-4-((5-(trifluoromethyl)pyridin-2-yl)oxy)benzenesulfonamide
3,4-difluoro-N-(2-(indolin-1-yl)ethyl)benzenesulfonamide
4-cyano-N-(2-(indolin-1-yl)ethyl)benzenesulfonamide
N—(N,N-diethylaminosulfonyl)-2-(indolin-1-yl)-2-methyl-propane-1-amine
N-(2-(indolin-1-yl)-2-methylpropyl)-4-(trifluoromethyl)benzenesulfonamide
N-(2-(indolin-1-yl)-2-methylpropyl)-4-phenoxybenzenesulfonamide
4-fluoro-N-(2-(indolin-1-yl)-2-methylpropyl)benzenesulfonamide
3,4-difluoro-N-(2-(indolin-1-yl)-2-methylpropyl)benzenesulfonamide
N-(2-(indolin-1-yl)-2-methylpropyl)-4-((5-(trifluoromethyl)pyrindin-2-yl)oxy)benzenesulfonamide
N-(2-(indolin-1-yl)-2-methylpropyl)-4-(methoxy)benzenesulfonamide
N-(2-(indolin-1-yl)-2-methylpropyl)-4-(trifluoromethoxy)benzenesulfonamide or a pharmaceutically acceptable salt thereof.

In some embodiments, the compound is
N-(2-(indol in-1-yl)propyl)-4-methoxybenzenesulfonamide
N-(2-(indolin-1-yl)propyl)-4-(trifluoromethoxy)benzenesulfonamide
N-(2-(indolin-1-yl)propyl)-4-(trifluoromethyl)benzenesulfonamide
4-cyano-N-(2-(indolin-1-yl)propyl)benzenesulfonamide
N-(2-(indolin-1-yl)propyl)-4-phenoxybenzenesulfonamide
N-(2-(indolin-1-yl)propyl)-4-((5-(trifluoromethyl)pyridin-2-yl)oxy)benzenesulfonamide
N-(2-(indolin-1-yl)ethyl)-4-(trifluoromethyl)benzenesulfonamide
N-(2-(indolin-1-yl)ethyl)-4-(trifluoromethoxy)benzenesulfonamide
N-(2-(indolin-1-yl)ethyl)-4-phenoxybenzenesulfonamide
N-(2-(indolin-1-yl)ethyl)-4-((5-(trifluoromethyl)pyridin-2-yl)oxy)benzenesulfonamide
3,4-difluoro-N-(2-(indolin-1-yl)ethyl)benzenesulfonamide
4-cyano-N-(2-(indolin-1-yl)ethyl)benzenesulfonamide
N-(2-(indolin-1-yl)-2-methylpropyl)-4-(trifluoromethyl)benzenesulfonamide
N-(2-(indolin-1-yl)-2-methylpropyl)-4-phenoxybenzenesulfonamide
4-fluoro-N-(2-(indolin-1-yl)-2-methylpropyl)benzenesulfonamide
3,4-difluoro-N-(2-(indolin-1-yl)-2-methylpropyl)benzenesulfonamide
N-2-(indolin-1-yl)-2-methylpropyl)-4-((5-(trifluoromethyl)pyridin-2-yl)oxy)benzenesulfonamide
N-(2-(indolin-1-yl)-2-methylpropyl)-4-methoxybenzenesulfonamide
N-(2-(indolin-1-yl)-2-methylpropyl)-4-(trifluoromethoxy)benzenesulfonamide
N-(2-(indolin-1-yl)ethyl)pyrrolidine-1-carboxamide
N-(2-(indolin-1-yl)propyl)-4-methylpiperazine-1-carboxamide
N-(2-(indolin-1-yl)propyl)-4-methylpiperazine-1-sulfonamide
N—(N,N-diethylaminosulfonyl)-2-(5-(3-methoxyphenyl)indolin-1-yl)-propane-1-amine
N—(N,N-diethylaminosulfonyl)-2-(indolin-1-yl)-2-methyl-propane-1-amine
1-(2-(4-((4-fluorophenyl)sulfonyl)piperazin-1-yl)ethyl)indoline
1-(2-(4-((4-trifluoromethoxy)phenyl)sulfonyl)piperazin-1-yl)ethyl)indoline
N,N-diethyl-4-(2-(indolin-1-yl)ethyl)piperazine-1-sulfonamide
N,N-diethyl-4-(2-(indolin-1-yl)ethyl)piperazine-1-carboxamide or a pharmaceutically acceptable salt thereof.

In some embodiments, the compound is
N-(2-(indolin-1-yl)propyl)-4-(trifluoromethoxy)benzenesulfonamide
N-(2-(indolin-1-yl)propyl)-4-(trifluoromethyl)benzenesulfonamide N-(2-(indolin-1-yl)propyl)-4-((5-(trifluoromethyl)pyridin-2-yl)oxy)benzenesulfonamide
N-(2-(indolin-1-yl)ethyl)-4-(trifluoromethyl)benzenesulfonamide
N-(2-(indolin-1-yl)ethyl)-4-(trifluoromethoxy)benzenesulfonamide
N-(2-(indolin-1-yl)ethyl)-4-phenoxybenzenesulfonamide
N-(2-(indolin-1-yl)ethyl)-4-((5-(trifluoromethyl)pyridin-2-yl)oxy)benzenesulfonamide
3,4-difluoro-N-(2-(indolin-1-yl)ethyl)benzenesulfonamide
4-cyano-N-(2-(indolin-1-yl)ethyl)benzenesulfonamide
N-(2-(indolin-1-yl)-2-methylpropyl)-4-(trifluoromethyl)benzenesulfonamide
N-(2-(indolin-1-yl)-2-methylpropyl)-4-phenoxybenzenesulfonamide
N-(2-(indolin-1-yl)-2-methylpropyl)-4-((5-(trifluoromethyl)pyridin-2-yl)oxy)benzenesulfonamide
N-(2-(indolin-1-yl)-2-methylpropyl)-4-methoxybenzenesulfonamide
N-(2-(indolin-1-yl)-2-methylpropyl)-4-(trifluoromethoxy)benzenesulfonamide
N-(2-(indolin-1-yl)ethyl)pyrrolidine-1-carboxamide
N—(N,N-diethylaminosulfonyl)-2-(indolin-1-yl)-2-methylpropane-1-amine
1-(2-(4-((4-fluorophenyl)sulfonyl)piperazin-1-yl)ethyl)indoline
1-(2-(4-((4-trifluoromethoxy)phenyl)sulfonyl)piperazin-1-yl)ethyl)indoline
N,N-diethyl-4-(2-(indolin-1-yl)ethyl)piperazine-1-sulfonamide
or a pharmaceutically acceptable salt thereof.
In some embodiments, the compound is
N-(2-(indolin-1-yl)ethyl)-4-phenoxybenzenesulfonamide
N-(2-(indolin-1-yl)ethyl)-4-((5-(trifluoromethyl)pyridin-2-yl)oxy)benzenesulfonamide
3,4-difluoro-N-(2-(indolin-1-yl)ethyl)benzenesulfonamide
4-cyano-N-(2-(indolin-1-yl)ethyl)benzenesulfonamide
or a pharmaceutically acceptable salt thereof.
In some embodiments, the compound is
1-(2-(4-((4-(trifluoromethoxy)phenyl)sulfonyl)piperazin-1-yl)ethyl)indoline
N,N-diethyl-4-(2-(indolin-1-yl)ethyl)piperazine-1-sulfonamide
1-(2-(4-((4-fluorophenyl)sulfonyl)piperazin-1-yl)ethyl)indoline
or a pharmaceutically acceptable salt thereof.

It should be appreciated that various substituents on the compounds of the present invention can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups are known in the art, and can be employed. Examples of many of the possible groups can be found in "Protective Groups in Organic Synthesis" by T. W. Green, John Wiley and Sons. 1981. For example, nitro groups can be added by nitration and the nitro group can be converted to other groups, such as amino by reduction, and halogen by diazotization of the amino group and replacement of the diazo group with halogen. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product, including isolated products.

Still further, combinations of the various variable groups described herein form other embodiments. In this manner, a variety of compounds are embodied within the present invention.

In another aspect, the invention provides pharmaceutical compositions. In one embodiment, the pharmaceutical composition may include a compound as described herein and a pharmaceutically acceptable carrier.

In another aspect, the compounds of the present invention are selective inhibitors of Nox4, and therefore can be used therapeutically for inter alia treating a clinical condition associated with fibrotic disorder.

In some embodiments, the invention provides a method for treating a clinical condition associated with fibrotic disorder, the method involving administering to a subject in need of such a treatment a therapeutically acceptable amount of a compound described herein, or a pharmaceutically acceptable salt thereof, or pharmaceutical composition described herein, to treat the clinical condition associated with fibrotic disorder.

In some embodiments, the clinical condition associated with fibrotic disorder comprises fibrotic disease of the kidney, liver, skin, lung or heart.

In some embodiments, the clinical condition associated with fibrotic disorder comprises idiopathic pulmonary fibrosis.

The compounds of the present invention can be administered to a patient to achieve a desired physiological effect. The compound can be administered in a variety of forms adapted to the chosen route of administration, i.e., orally or parenterally. Parenteral administration in this respect includes administration by the following routes: intravenous; intramuscular; subcutaneous; intraocular; intrasynovial; transepithelially including transdermal, ophthalmic, sublingual and buccal; topically including ophthalmic, dermal, ocular, rectal and nasal inhalation via insufflation and aerosol; intraperitoneal; and rectal systemic. In some embodiments, administration is accomplished by oral inhalation, for example, through use of a mouth inhaler.

The active compound can be orally administered, for example, with an inert diluent or with an assimilable edible carrier, or it can be enclosed in hard or soft shell gelatin capsules, or it can be compressed into tablets, or it can be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparation can contain at least 0.1% of active compound. The percentage of the compositions and preparation can, of course, be varied and can conveniently be between about 1 to about 10% of the weight of the unit. The amount of active compound in such therapeutically useful compositions is such that a suitable dosage will be obtained. Preferred compositions or preparations according to the present invention are prepared such that an oral dosage unit form contains from about 1 to about 1000 mg of active compound.

The tablets, troches, pills, capsules and the like can also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin can be added or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the active compound, sucrose as a sweetening agent, methyl and propylparabens a preservative, a dye and flavoring such as cherry or orange flavor. Of course, any material used in preparing any dosage unit form should be pharmaceutically pure and substantially non-toxic in the amounts employed. In addition, the active compound can be incorporated into sustained-release preparations and formulation.

The active compound can also be administered parenterally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It can be stable under the conditions of manufacture and storage and must be preserved against the contaminating action of microorganisms such as bacterial and fungi. The carrier can be a solvent of dispersion medium containing, for example, water, ethanol, polyol (e.g., glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, e.g., sugars or sodium chloride. Prolonged absorption of the injectable compositions of agents delaying absorption, e.g., aluminum monostearate and gelatin.

Sterile injectable solutions are prepared by incorporating the active compound in the required amount in the appropriate solvent with various other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying techniques which yield a powder of the active ingredient plus any additional desired ingredient from previously sterile-filtered solution thereof.

The therapeutic compounds of the present invention can be administered to a mammal alone or in combination with pharmaceutically acceptable carriers, as noted above, the proportion of which is determined by the solubility and chemical nature of the compound, chosen route of administration and standard pharmaceutical practice.

The therapeutic compounds of the present invention can be administered in combination with one or more drugs for the treatment of idiopathic pulmonary fibrosis (IPF) and/or an antioxidant. For example, the compounds of the present invention can be administered in combination with Pirfenidone, N-acetylcysteine, triple therapy (i.e., N-acetylcysteine in combination with prednisone and azathioprine), Nintedanib or a combination thereof.

The physician will determine the dosage of the present therapeutic agents which will be most suitable for prophylaxis or treatment and it will vary with the form of administration and the particular compound chosen, and also, it will vary with the particular patient under treatment. The physician will generally wish to initiate treatment with small dosages by small increments until the optimum effect under the circumstances is reached. The therapeutic dosage can generally be from about 0.1 to about 1000 mg/day, and preferably from about 10 to about 100 mg/day, or from about 0.1 to about 50 mg/Kg of body weight per day and preferably from about 0.1 to about 20 mg/Kg of body weight per day and can be administered in several different dosage units. Higher dosages, on the order of about 2× to about 4×, may be required for oral administration.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

The following abbreviations are used: HOBt (1-Hydroxybenzotriazole); DCM (Dichloromethane); EtOAc (Ethyl acetate); MeOH (Methanol); HBTU (2-(1H-benzotriazol-1-yl)-1,1,3,3-tetramethyluronium hexafluorophosphate); DIEA (N,N-diisopropylethylamine); DMF (N,N-dimethylformamide); $Pd_2(dba)_3$ (Tris(dibenzylideneacetone)dipalladium(0)); Boc (t-Butyloxycarbonyl); $(Boc)_2O$ (Di-tert-butyl dicarbonate); AcOH (Acetic acid); EtOH (Ethanol); $Et_3N$ (Triethylamine); TLC (Thin layer chromatography); and NMR (Nuclear magnetic resonance).

General Procedure:

All the chemicals were purchased from commercial vendors. All the solvents were obtained from Fischer Scientific. Flash chromatography was performed with silica gel (230/400 mesh, Fisher Scientific). All anhydrous reactions were carried out under positive pressure of nitrogen. HPLC-MS analyses were performed on an Agilent 1100 series instrument with a Zorbax C18 reverse-phase column. The gradient was 90 to 95 ACN in water over 20 minutes at 10 mL/min. The Chiral HPLC analyses were performed on Agilent 1100 series instrument with Chiralcel OD-RH, 5 um, 4.6×150 mm column. HPLC purification of chiral compounds were performed on Phenomenex Lux Amylose-2, Axia Packed, 5 urn, 21.20×250 mm. The solvent system used was 60% ACN in water isocratic run (no gradient) at 1 mL/min. HRMS results were obtained on an apex-Qe instrument. All $^1$H-NMR and $^{13}$C-NMR spectra were recorded on a BRUKER AVANCE-III 400 MHz NMR instrument, using deuterated solvents. The spectra are reported in ppm and referenced to deuterated DMSO (2.49 ppm for $^1$H, 39.5 ppm for $^{13}$C) or deuterated chloroform (7.26 ppm for $^1$H, 77 ppm for $^{13}$C). High-resolution mass spectra (HRMS) were acquired on a Bruker 9.4 T Apex-Qh FTICR mass spectrometer. All the microwave assisted reactions were performed using a biotage initiator instrument. All compounds were analyzed for purity by HPLC using either MS or UV absorbance detectors.

Scheme 1: Synthesis of 2-(indolin-1-yl)ethan-1-amine (i)

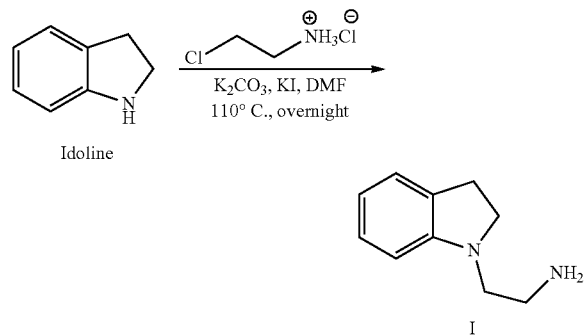

In a round bottomed flask equipped with a nitrogen inlet, a magnetic stir bar and a reflux condenser, a solution of indoline (4.52 g, 35.68 mmol, 4 mL) in 30 mL DMF was added. To the above solution, $K_2CO_3$ (14 g, 101 mmol) was added and then the mixture was stirred for 30 min. Potassium iodide (0.58 g, 3.57 mmol, 0.1 eq) and 2-chloroethylamine hydrochloride (4.64 g, 39.25 mmol) were then added to the mixture. The mixture was then heated at 110° C. overnight. The reaction was then diluted with 200 mL water, extracted with EtOAc (100 mL×3). The combined organic layers were dried over anhydrous $Na_2SO_4$, concentrated and then dried in vacuo yielding 8.35 g of the crude product. The crude was then diluted with diethyl ether and then, 2 N HCl was added. The phases were then separated, and the aqueous layer was then basified with 2.5 N NaOH. The aqueous was then extracted with EtOAc and the combined organic layers were dried over anhydrous $Na_2SO_4$, concentrated and then dried in vacuo yielding 6.32 g of the crude. The product was purified by a silica gel column chromatography using 1:1 EtOAc:hexanes to separate excess indoline and the desired product was eluted with 10% MeOH in $CH_2Cl_2$. The combined fractions were concentrated and then dried in vacuo to yield 2.38 g (41%) of the brown oily compound as the desired product. $^1$H NMR (400 MHz, $CDCl_3$) δ 7.10 (t, J=6.8 Hz, 1H), 7.07 (t, J=8 Hz, 1H), 6.71 (t, J=8 Hz, 1H), 6.52 (d, J=8 Hz, 1H), 3.56 (q, J=8 Hz, 2H), 3.38 (t, J=8 Hz, 2H), 3.23 (t, J=8 Hz, 2H), 3.30 (t, J=8 Hz, 2H).

Compound UANOX001 (N—(N,N-diethylaminosulfonyl)-2-(indolin-1-yl)ethan-1-amine)

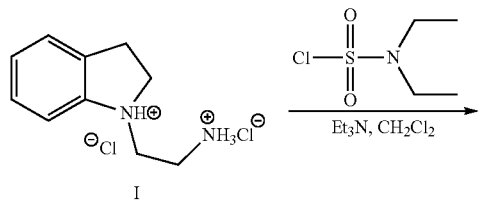

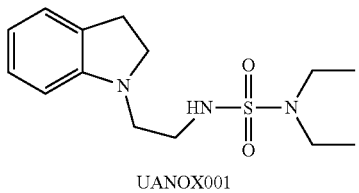

UANOX001

In a round bottomed flask equipped with a nitrogen inlet and a magnetic stir bar, a solution of 0.21 g (1.22 mmol) of N,N-diethylsulfamoyl chloride in 5 mL of $CH_2Cl_2$ was added. To the above solution 0.235 g (1 mmol) of 2-(indolin-1-yl)ethan-1-amine dihydrochloride (i.2HCl) and 0.40 mL (2.87 mmol) of triethylamine was added. The reaction was stirred vigorously at room temperature for 18 h and then, quenched using 20 mL water. The aqueous layer was then extracted with $CH_2Cl_2$ (15 mL×3). The combined organic extracts were dried over anhydrous $Na_2SO_4$, concentrated and then dried in vacuo giving 0.40 g of the crude product. The crude was then purified by column chromatography using 30% EtOAc in hexanes. The fractions were concentrated and then dried in vacuo yielding 170 mg (57%) of the desired product as light yellow oil. $^1$H NMR (400 MHz, $CDCl_3$) δ 7.13 (d, J=8.0 Hz, 1H), 7.11 (t, J=8 Hz, 1H), 6.74 (t, J=8 Hz, 1H), 6.57 (d, J=8 Hz, 1H), 4.63 (s, 2H), 3.38 (t, J=8 Hz, 2H), 3.32 (q, J=8 Hz, 4H), 3.28-3.23 (m, 4H), 3.02 (t, J=8 Hz, 2H), 1.23 (t, J=8 Hz, 6H). HPLC-MS: Expected: 298 (MH+); Found: 298.

UANOX002 (1,1-diethyl-3-(2-(indolin-1-yl)ethyl)urea)

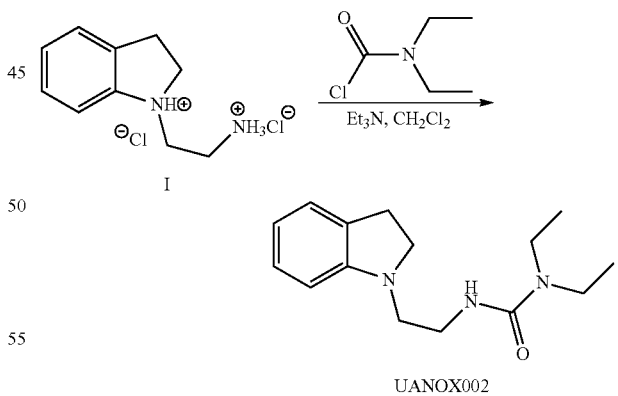

UANOX002

Compound UANOX002 was synthesized as per the procedure described for compound UANOX001. $^1$H NMR (400 MHz, $CDCl_3$) δ 7.28-7.09 (m, 2H), 6.74 (t, J=8 Hz, 1H), 6.55 (d, J=8 Hz, 1H), 4.63 (bs, 1H), 3.38 (t, J=8 Hz, 2H), 3.32 (quartet, J=8 Hz, 4H), 3.28-3.23 (m, 4H), 3.02 (t, J=8 Hz, 2H), 1.23 (t, J=8 Hz, 6H). HPLC-MS: Expected: 262 (MH+); Found: 262.

UANOX003 (N—(N,N-dimethylaminosulfonyl)-2-(indolin-1-yl)ethan-1-amine)

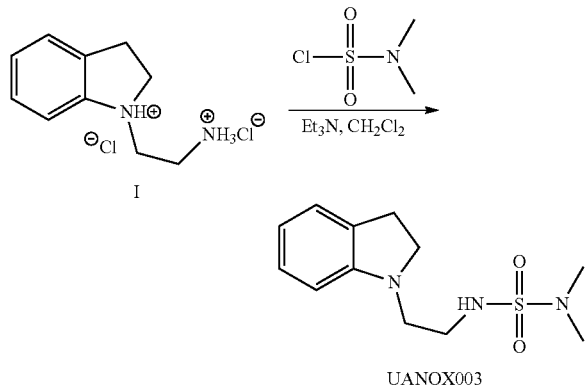

UANOX003 was synthesized as per the procedure described for compound UANOX001. $^1$H NMR (400 MHz, CDCl3) δ 7.13 (d, J=8.0 Hz, 1H), 7.10 (t, J=8 Hz, 1H), 6.74 (t, J=8 Hz, 1H), 6.56 (d, J=8 Hz, 1H), 4.69 (s, 1H), 3.39 (t, J=8 Hz, 2H), 3.34-3.25 (m, 4H), 3.02 (t, J=8 Hz, 2H), 2.85 (s, 6H). HPLC-MS: Expected: 270 (MH$^+$); Found: 270.

UANOX004 (N-(2-(indolin-1-yl)ethyl)pyrrolidine-1-sulfonamide)

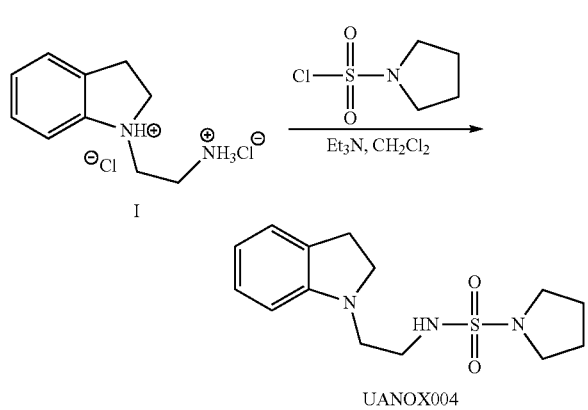

UANOX004 was synthesized as per the procedure described for compound UANPX001. $^1$H NMR (400 MHz, CDCl$_3$) δ 7.13 (d, J=8.0 Hz, 1H), 7.10 (t, J=8 Hz, 1H), 6.74 (t, J=8 Hz, 1H), 6.56 (d, J=8 Hz, 1H), 4.70 (s, 1H), 3.39 (t, J=8 Hz, 2H), 3.36-3.26 (m, 8H), 3.02 (t, J=8 Hz, 2H), 1.95 (s, 4H). HPLC-MS: Expected: 296 (MH$^+$); Found: 296.

UANOX011 (N-(2-(indolin-1-yl)ethyl)-4-methylpiperazine-1-carboxamide)

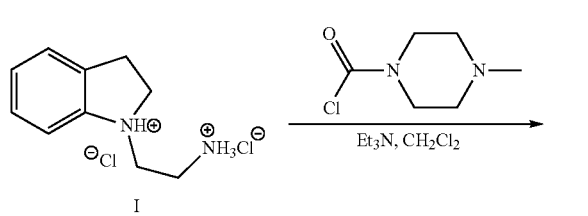

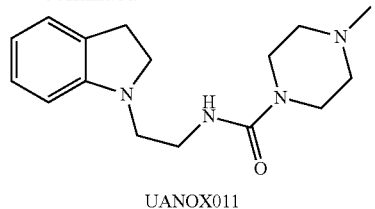

UANOX011 was synthesized as per the procedure described for compound UANOX001. $^1$H NMR (400 MHz, CDCl$_3$) δ 7.11 (d, J=8 Hz, 1H), 7.08 (t, J=8 Hz, 1H), 6.70 (1, J=8 Hz, 1H), 6.58 (d, J=8 Hz, 1H), 4.65 (bs, 1H), 3.53 (q, 4 Hz, 2H), 3.43 (t, J=8 Hz, 2H), 3.39-3.30 (m, 6H), 3.26 (t, J=8 Hz, 2H), 2.85 (s, 3H), 1.9-1.88 (m, 2H), 1.86-1.82 (m, 2H). HPLC-MS: Expected: 310 (M+Na); Found: 310.

UANOX012 (N-(2-(indolin-1-yl)ethyl)morpholine-4-sulfonamide)

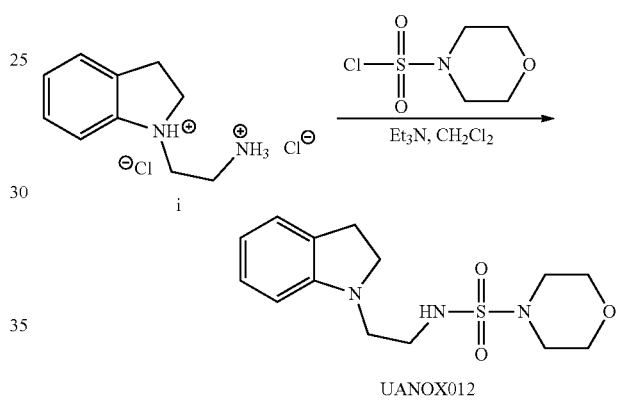

UANOX012 was synthesized as per the procedure described for compound UANOX001. $^1$H NMR (400 MHz, CDCl$_3$) δ 7.17-7.07 (m, 2H), 6.75 (t, J=8 Hz, 1H), 6.58 (d, J=8 Hz, 1H), 4.70 (bs, 1H), 3.78-3.75 (m, 6H), 3.39 (t, J=8 Hz, 2H), 3.26-3.23 (m, 6H), 3.03 (t, J=8 Hz, 2H). HPLC-MS: Expected: 312 (MH$^+$); Found: 312.

UANOX021 (N-(2-(indolin-1-yl)ethyl)pyrrolidine-1-carboxamide)

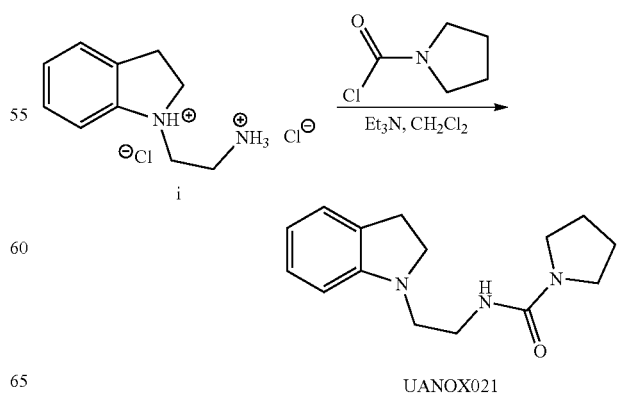

UANOX021 was synthesized as per the procedure described for UANOX001. ¹H NMR (400 MHz, CDCl₃) δ 7.12-7.06 (m, 2H), 6.70 (t, J=8 Hz, 1H), 6.57 (d, J=8 Hz, 1H), 4.61 (bs, 1H), 3.52 (quartet, J=8 Hz, 2H), 3.42 (t, J=8 Hz, 2H), 3.32 (t, J=8 Hz, 4H), 3.25 (t, J=8 Hz, 2H), 3.01 (t, J=8 Hz, 2H), 1.90 (t, J=8 Hz, 4H). HPLC-MS: Expected: 260 (MH⁺); Found: 260.

UANOX013 (N-(2-(indolin-1-yl)ethyl)piperidine-1-sulfonamide)

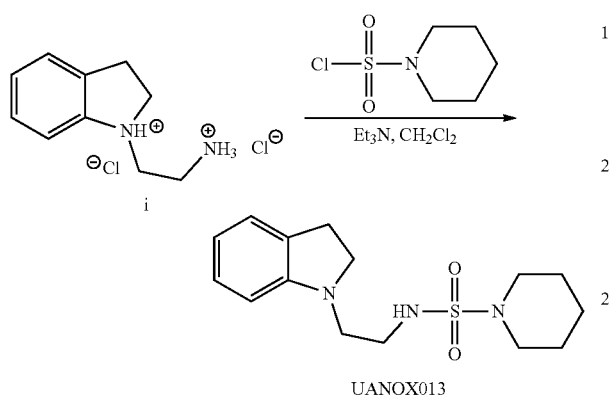

UANOX013

UANOX013 was synthesized as per the procedure described for compound UANOX001. ¹H NMR (400 MHz, Chloroform-d) δ 7.23-6.99 (m, 2H), 6.76 (td, J=7.4, 0.9 Hz, 1H), 6.59 (d, J=7.8 Hz, 1H), 4.60 (bs, 1H), 3.40 (t, J=8.2 Hz, 2H), 3.36-3.26 (m, 4H), 3.25-3.20 (m, 4H), 3.02 (t, J=8.2 Hz, 2H), 1.77-1.46 (m, 6H). HPLC-MS: Expected: 311 (M+2); Found: 311.

UANOX051 (4-fluoro-N-(2-(indolin-1-yl)ethyl)benzenesulfonamide)

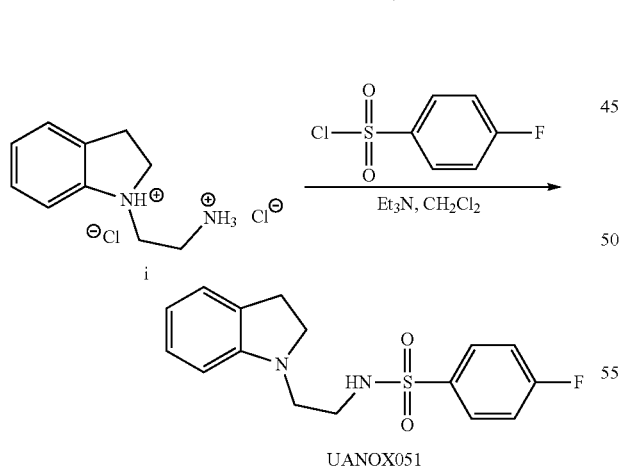

UANOX051

UANOX051 was synthesized as per the procedure described for compound UANOX001. ¹H NMR (400 MHz, CDCl₃) ¹H NMR (400 MHz, Chloroform-d) δ 7.92 (dd, J=9.0, 5.1 Hz, 2H), 7.21 (t, J=9.2, 2H), 7.11 (d, J=7.2 Hz, 1H), 7.07 (t, J=7.7 Hz, 1H), 6.73 (t, J=7.8 Hz, 1H), 6.39 (d, J=7.2 Hz, 1H), 3.44-3.07 (m, 6H), 2.95 (t, J=8.2 Hz, 2H). HPLC-MS: Expected: 321 (MH⁺); Found: 321.

UANOX050 (4-methoxy-N-(2-(indolin-1-yl)ethyl)benzenesulfonamide)

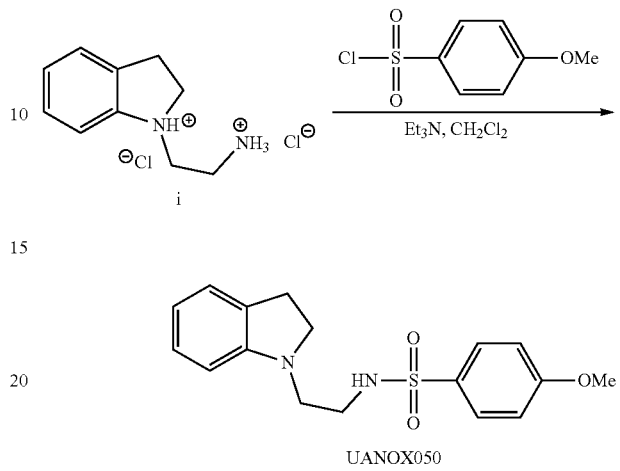

UANOX050

UANOX050 was synthesized as per the procedure described for compound UANOX001. ¹H NMR (400 MHz, Chloroform-d) δ 7.84 (d, J=9.1 Hz, 2H), 7.10 (d, J=7.9 Hz, 1H), 7.06 (d, J=8 Hz, 1H), 7.00 (d, J=9.1 Hz, 2H), 6.72 (t, J=8 Hz, 1H), 6.38 (d, J=8.1 Hz, 1H), 3.90 (s, 3H), 3.24-3.12 (m, 6H), 2.94 (t, J=8.3 Hz, 2H). HPLC-MS: Expected: 333 (MH⁺); Found: 333.

UANOX075 (4-trifluoromethyl-N-(2-(indolin-1-yl)ethyl)benzenesulfonamide)

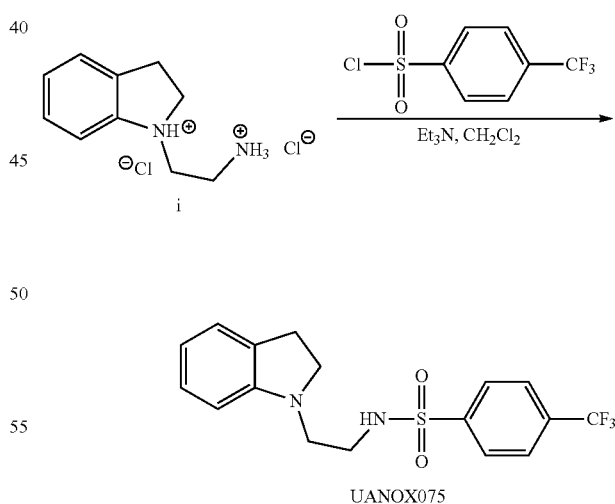

UANOX075

UANOX075 was synthesized as per the procedure described for compound UANOX001.

¹H NMR (400 MHz, Chloroform-d) δ 7.96 (d, J=8.7 Hz, 2H), 7.73 (d, J=8.2 Hz, 2H), 7.04 (d, J=7.2 Hz, 1H), 7.00 (t, J=7.7 Hz, 1H), 6.67 (t, J=7.4 Hz, 1H), 6.29 (d, J=7.9 Hz, 1H), 5.08 (bs, 1H), 3.26-3.06 (m, 6H), 2.87 (t, J=8.3 Hz, 2H). HPLC-MS: Expected: 371 (MH⁺); Found: 371.

UANOX076 (4-trifluoromethoxy-N-(2-(indolin-1-yl)ethyl)benzenesulfonamide)

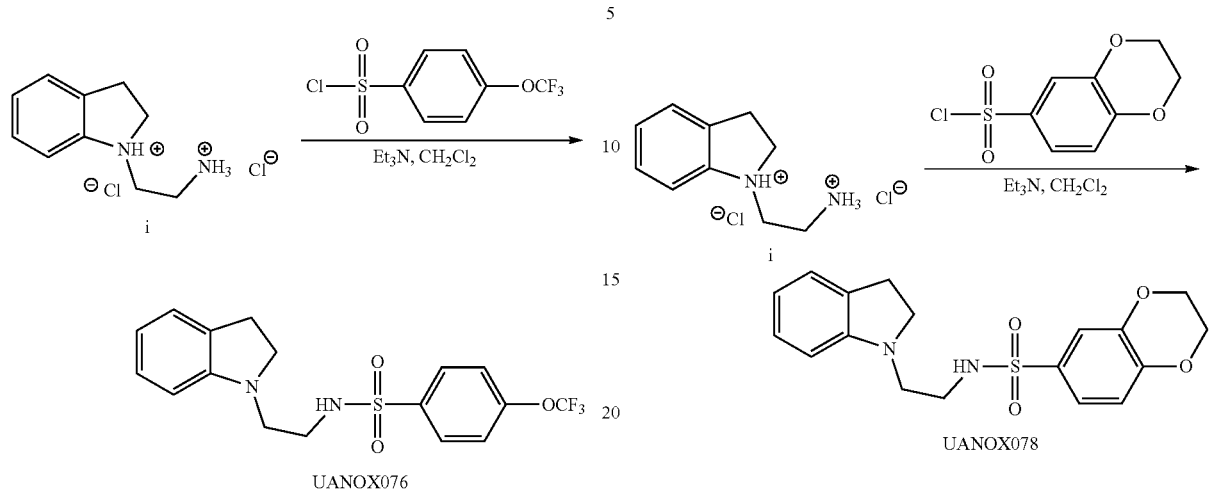

UANOX076 was synthesized as per the procedure described for compound UANOX001.

$^1$H NMR (400 MHz, Chloroform-d) δ 7.90 (d, J=9.7 Hz, 2H), 7.31 (d, J=8.7 Hz, 2H), 7.05 (d, J=7.2 Hz, 1H), 7.01 (t, J=7.7 Hz, 1H), 6.68 (t, J=7.4 Hz, 1H), 6.32 (d, J=7.2 Hz, 1H), 4.94 (bs, 1H), 3.25-3.04 (m, 6H), 2.89 (t, J=7.7 Hz, 2H). HPLC-MS: Expected: 387 (MH$^+$); Found: 387.

UANOX077 (N-(2-(indolin-1-yl)ethyl)benzo[d][1,3]dioxole-5-sulfonamide)

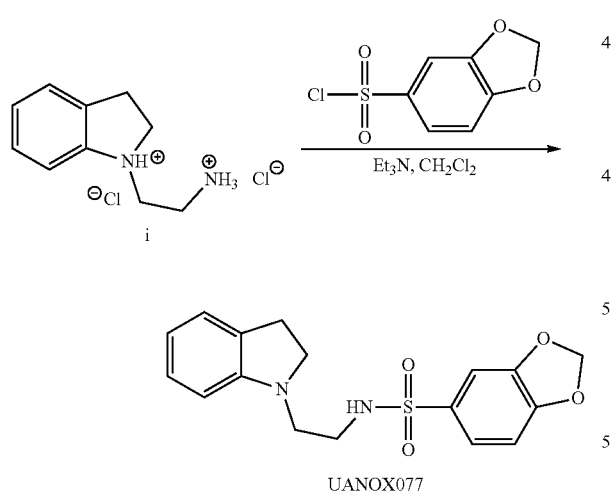

UANOX077 was synthesized as per the procedure described for compound UANOX001.

$^1$H NMR (400 MHz, Chloroform-d) δ 7.41 (dd, J=8.2, 1.8 Hz, 1H), 7.23 (dd, J=7.2, 1.3 Hz, 1H), 7.04 (d, J=7.2 Hz, 1H), 7.01 (t, J=7.7 Hz, 1H), 6.84 (d, J=8.2 Hz, 1H), 6.66 (t, J=7.4 Hz, 1H), 6.34 (d, J=7.9 Hz, 1H), 6.04 (s, 2H), 4.83 (bs, 1H), 3.24-3.02 (m, 6H), 2.89 (t, J=8.2 Hz, 2H). HPLC-MS: Expected: 347 (MH$^+$); Found: 347.

UANOX078 (N-(2-(indolin-1-yl)ethyl)-2,3-dihydrobenzo[b][1,4]dioxine-6-sulfonamide)

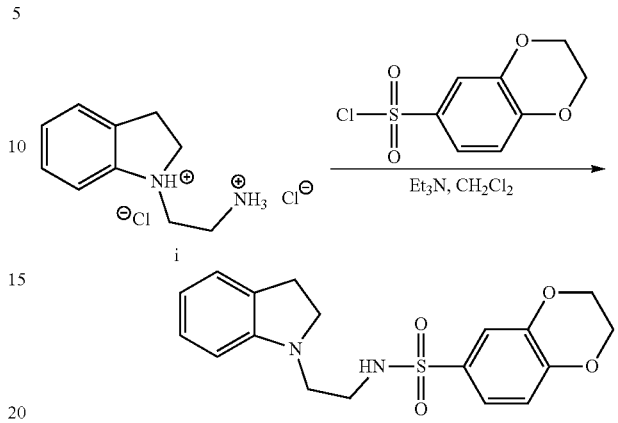

UANOX078 was synthesized as per the procedure described for compound UANOX001.

$^1$H NMR (400 MHz, Chloroform-d) δ 7.37 (dd, J=2.2, 1.2 Hz, 1H), 7.32 (ddd, J=8.5, 2.2, 1.3 Hz, 1H), 7.04 (d, J=7.0 Hz, 1H), 7.01 (t, J=7.7 Hz, 1H), 6.92 (dd, J=8.5, 0.9 Hz, 1H), 6.66 (t, J=7.4 Hz, 1H), 6.34 (d, J=7.9 Hz, 1H), 4.77 (bs, 1H), 4.35-4.12 (m, 4H), 3.22-3.00 (m, 6H), 2.89 (t, J=8.2 Hz, 2H). HPLC-MS: Expected: 361 (MH$^+$); Found: 361.

UANNOX079 (N-(2-(indolin-1-yl)ethyl)-4-phenoxybenzenesulfonamide)

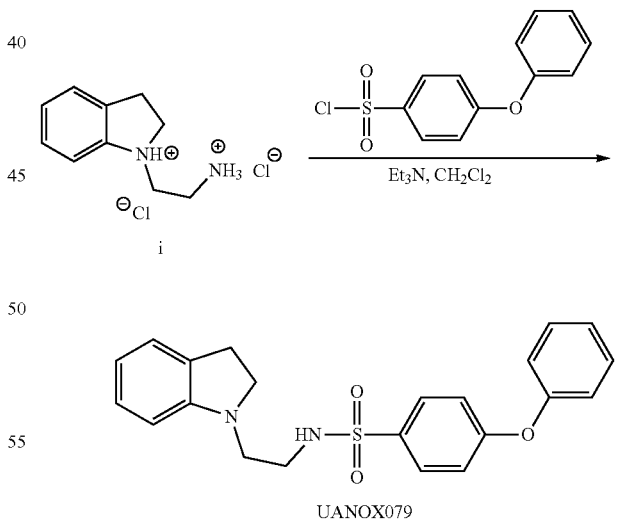

UANOX079 was synthesized as per the procedure described for compound UANOX001.

$^1$H NMR (400 MHz, Chloroform-d) δ 7.79 (d, J=8.8 Hz, 2H), 7.39 (t, J=8.0 Hz, 2H), 7.20 (t, J=7.4 Hz, 1H), 7.08-6.85 (m, 6H), 6.67 (t, J=7.3 Hz, 1H), 6.34 (d, J=7.9 Hz, 1H), 4.86 (t, J=5.6 Hz, 1H), 3.21-3.06 (m, 6H), 2.90 (t, J=8.2 Hz, 2H). HPLC-MS: Expected: 395 (MH$^+$); Found: 395.

UANOX080 (N-(2-(indolin-1-yl)ethyl)-4-((5-(trifluoromethyl)pyridin-2-yl)oxy)benzenesulfonamide)

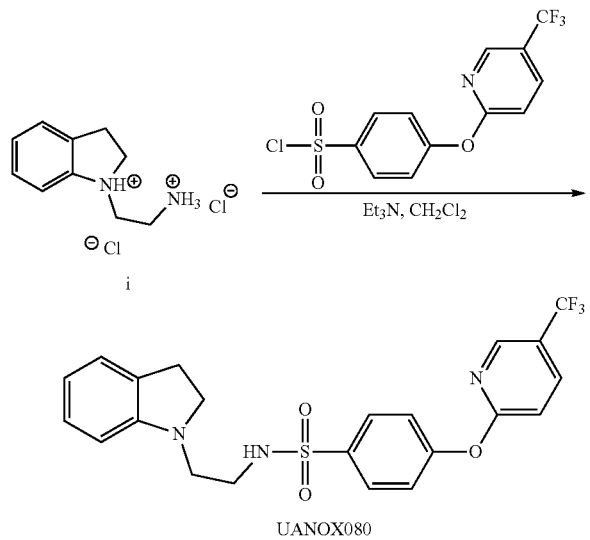

UANOX080 was synthesized as per the procedure described for compound UANOX080.

$^1$H NMR (400 MHz, Chloroform-d) δ 8.41 (s, 1H), 7.95 (dd, J=8.6, 2.5 Hz, 1H), 7.91 (d, J=8.9 Hz, 2H), 7.27 (d, J=8.5 Hz, 2H), 7.09 (d, J=9.2 Hz, 1H), 7.05 (d, J=7.2 Hz, 1H), 7.01 (t, J=8.0 Hz, 1H), 6.67 (t, J=7.4 Hz, 1H), 6.37 (d, J=7.8 Hz, 1H), 4.90 (t, J=5.7 Hz, 1H), 3.29-3.07 (m, 6H), 2.91 (t, J=8.1 Hz, 2H). HPLC-MS: Expected: 464 (MH$^+$); Found: 464.

UANOX082 (4-cyano-N-(2-(indolin-1-yl)ethyl)benzenesulfonamide)

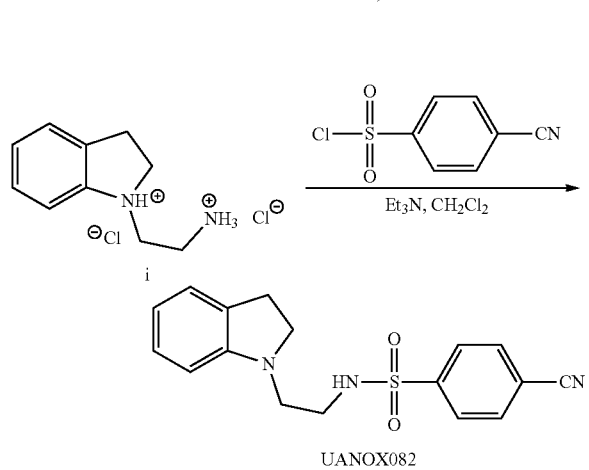

UANOX082 was synthesized as per the procedure described for compound UANOX001.

$^1$H NMR (400 MHz, Chloroform-d) δ 7.92 (d, J=7.7 Hz, 2H), 7.71 (d, J=7.4 Hz, 2H), 7.04 (d, J=7.2 Hz, 1H), 7.00 (t, J=7.7 Hz, 1H), 6.68 (t, J=7.4 Hz, 1H), 6.29 (d, J=7.9 Hz, 1H), 5.11 (bs, 1H), 3.27-3.03 (m, 6H), 2.87 (t, J=8.2 Hz, 2H). $^{13}$C NMR (101 MHz, Chloroform-d) δ 151.68, 144.25, 132.85, 129.77, 127.52, 127.32, 124.70, 118.87, 117.21, 116.26, 107.08, 53.57, 49.57, 41.25, 28.49. HPLC-MS: Expected: 328 (MH$^+$); Found: 328.

UANOX081 (3,4-difluoro-N-(2-(indolin-1-yl)ethyl)benzenesulfonamide)

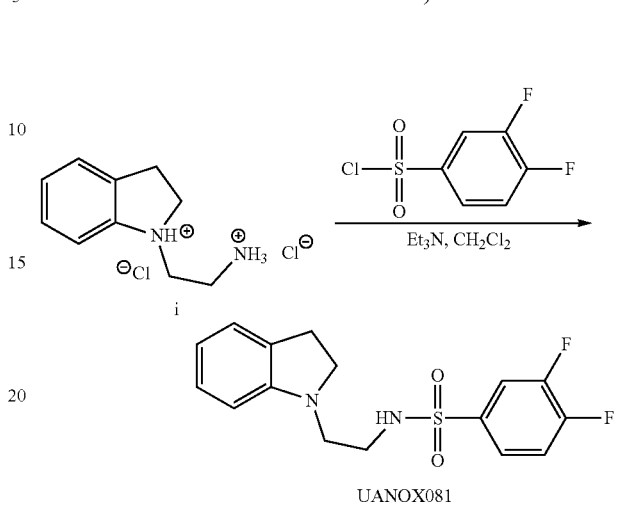

UANNOX081 was synthesized as per the procedure described for compound UANOX001.

$^1$H NMR (400 MHz, Chloroform-d) δ 7.67 (t, J=8.1 Hz, 1H), 7.61 (d, J=8.4 Hz, 1H), 7.30-7.22 (m, 1H), 7.05-6.99 (m, 2H), 6.67 (t, J=7.3 Hz, 1H), 6.34 (d, J=7.8 Hz, 1H), 4.94 (bs, 1H), 3.27-3.03 (m, 6H), 2.89 (t, J=8.1 Hz, 2H). HPLC-MS: Expected: 339 (MH$^+$); Found: 339.

Synthesis of UANOX017
(4-(2-(indolin-1-yl)ethyl)morpholine)

Scheme 2

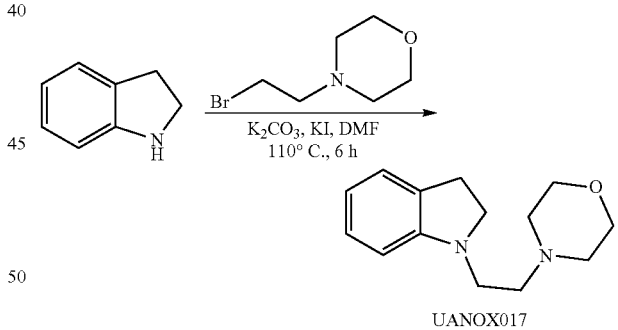

In a round bottomed flask equipped with a nitrogen inlet, a magnetic stir bar and a reflux condenser, solution of indoline (0.2 mL, 0.213 g, 1.78 mmol) in 2 mL DMF was added. To the above solution, K$_2$CO$_3$ (0.707 g, 5.11 mmol) was added and then the mixture was stirred for 30 min. Potassium iodide (0.03 g, 0.19 mmol) and 4-(2-bromoethyl)morpholine hydrochloride (0.34 g, 1.78 mmol) were then added. The reaction mixture was then heated at 110° C. or 6 hr. The mixture was then diluted with water (20 mL) and then, extracted with EtOAc (15 mL×3). The combined organic layers were dried over anhydrous Na$_2$SO$_4$, concentrated and then dried in vacuo. The crude product was purified using column chromatography, initially with 30% EtOAc in hexanes (to elute indoline) and then, with 10%

MeOH in CH$_2$Cl$_2$ to obtain 0.246 g (59%) of the desired product. $^1$H NMR (400 MHz, CDCl$_3$) δ 7.04-7.00 (m, 2H), 6.60 (t, J=8 Hz, 1H), 6.45 (d, J=8 Hz, 1H), 3.70 (t, J=4 Hz, 4H), 3.37 (t, J=8 Hz, 2H), 3.20 (t, J=4 Hz, 2H), 2.93 (t, J=8 Hz, 2H), 2.58 (t, J=8 Hz, 2H), 2.51 (m, 4H). HPLC-MS: Expected: 233 (MH$^+$); Found: 233.

UANOX018 (1-(2-(piperidin-1-yl)ethyl)indoline)

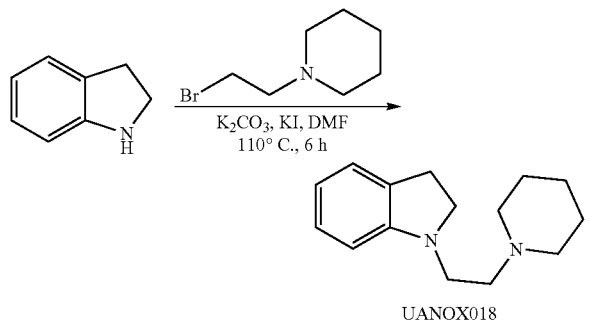

UANOX018

UANOX018 was synthesized from indoline and 1-(2-bromoethyl)piperidine according to the procedure described for the synthesis of compound UANOX017. $^1$H NMR (400 MHz, CDCl$_3$) δ 7.10-7.06 (m, 2H), 6.66 (t, J=8 Hz, 1H), 6.52 (d, J=8 Hz, 1H), 3.42 (t, J=8 Hz, 2H), 3.28 (t, J=8 Hz, 2H), 3.01-2.97 (m, 2H), 2.62 (t, J=8 Hz, 2H), 2.53 (t, J=8 Hz, 4H), 1.66 (quintet, J=4 Hz, 4H), 1.52-1.47 (n, 2H). HPLC-MS: Expected: 231 (MH$^+$); Found: 231.

Scheme 3

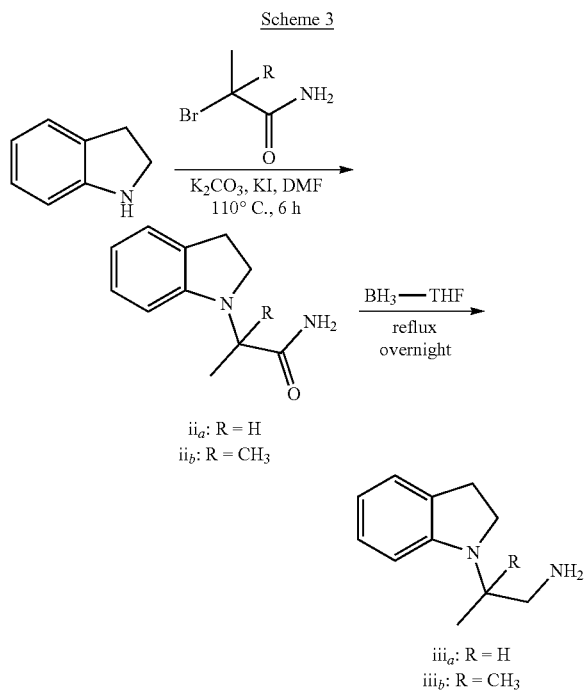

ii$_a$: R = H
ii$_b$: R = CH$_3$ iii$_a$: R = H
iii$_b$: R = CH$_3$

Synthesis of 2-(indolin-1-yl)propanamide (iia): In a round bottomed flask equipped with a nitrogen inlet, a magnetic stir bar and a reflux condenser, a solution of indoline (5.315 g, 44.6 mmol, 5 mL) in 42 mL DMF was added. To the above solution, K$_2$CO$_3$ (18 g, 130 mmol) was added and then the mixture was stirred for 30 min. Potassium iodide (0.8 g, 4.91 mmol, 0.1 eq) and 2-bromopropiomamide (7.46 g, 49.06 mmol) were then added to the mixture. The mixture was then heated at 110° C. or 2 hr. The mixture was then diluted with water (200 mL), extracted with CH$_2$Cl$_2$ (70 mL×3). The combined organic layers were dried over anhydrous Na$_2$SO$_4$, concentrated and then dried in vacuo yielding 13.45 g of the crude product. Crystals crashed out of the crude on standing for 48 hours. The supernatant oil was removed and the crystals were washed with minimal amount of anhydrous diethyl ether. The product was recrystallized with anhydrous diethyl ether to give 1.65 g (19%) of pure product (found by NOESY to be one of the enantiomers). The supernatant wine color oily crude (11.5 g) was column chromatographed with 5% MeOH in CH$_2$Cl$_2$ to yield two fractions. $^1$H NMR was used to confirm that the two fractions were the same compound. The combined organic layers of the two fractions containing the desired product were separately concentrated and then dried in vacuo to obtain the desired product as brown colored oil. This oily product turns solid on further drying. The solid was then washed with hexanes to remove excess DMF and the dried in vacuo yielding 6.85 g (79%) of the desired product as brown solid. Over all yield is 98%. $^1$H NMR (400 MHz, CDCl$_3$) δ 7.14 (d, J=8.0 Hz, 1H), 7.09 (t, J=8 Hz, 1H), 6.76 (t, J=8 Hz, 1H), 6.49 (d, J=8 Hz, 1H), 3.95 (q, J=8 Hz, 1H), 3.49 (q, J=8 Hz, 1H), 3.42 (q, J=8 Hz, 1H), 3.02 (t, J=8 Hz, 2H), 1.43 (d, J=8 Hz, 3H). HPLC-MS: Expected: 191 (MH$^+$); Found: 191.

2-(indolin-1-yl)-2-methylpropanamide (Iib) was synthesized from indoline and 2-bromo-2-methylpropanamide according to the procedure described for the synthesis of compound Ha. $^1$H NMR (400 MHz, Chloroform-d) δ 7.27 (d, J=7.3 Hz, 1H), 7.18 (t, J=7.7 Hz, 1H), 6.90 (t, J=7.4 Hz, 1H), 6.62 (d, J=7.9 Hz, 1H), 5.67 (bs, 1H), 3.56 (td, J=8.2, 1.4 Hz, 2H), 3.11 (t, J=8.1 Hz, 2H), 2.13 (t, J=1.1 Hz, 3H), 1.57 (t, J=1.1 Hz, 3H). LCMS: Expected: 205 (MH$^+$); Found: 205.

Synthesis of 2-(indolin-1-yl)propan-1-amine (iiia): A round bottomed flask equipped with a nitrogen inlet and a reflux condenser and 2-(indolin-1-yl)propanamide (8.04 mmol, 1.53 g) was dissolved in 1M BH$_3$.THF (25 mL) was added. The reaction mixture was then heated to reflux for 18 h. The reaction mixture was allowed to cool to room temperature and then quenched slowly with MeOH. The solution was concentrated, dissolved in MeOH, and again concentrated. The resulting oil was diluted with diethyl ether and extracted twice with 1 N HCl. The aqueous phase was treated with 2.5 N NaOH to adjust the pH >10 and then, extracted with EtOAc. The combined EtOAc extracts were dried over Na$_2$SO$_4$, and concentrated to provide 0.97 g of yellowish oil as crude. The crude product was purified by silica gel column chromatography using 10-20% MeOH in CH$_2$Cl$_2$. The combined fractions were evaporated and then dried in vacuo yielding 0.78 g (55%) of the pure product as a mixture of two enantiomers. $^1$H NMR (400 MHz, CDCl$_3$) δ 7.09-7.05 (m, 2H), 6.64 (t, J=8 Hz, 1H), 6.49 (d, J=8 Hz, 1H), 3.73-3.64 (m, 1H), 3.37 (quartet, J=8 Hz, 1H), 3.29 (quartet, J=8 Hz, 1H), 2.99 (dd, J=8 Hz, 7 Hz, 2H), 2.82 (ddd, J=36 Hz, 8 Hz, 12 Hz, 2H), 1.07 (d, J=8 Hz, 3H). 2-(indolin-1-yl)-2-methylpropan-1-amine (iiib) was synthesized according to the procedure described for the synthesis of compound iiia. $^1$H NMR (400 MHz, Chloroform-d) δ 7.31 (d, J=7.6 Hz, 1H), 7.24 (t, J=8.1 Hz, 1H), 7.00 (d, J=7.9 Hz, 1H), 6.88 (t, J=7.3 Hz, 1H), 3.68 (t, J=8.6 Hz, 2H), 3.20

(s, 2H), 3.14 (t, J=8.6 Hz, 2H), 1.85-1.64 (bs, 1H), 1.63 (d, J=30.5 Hz, 3H), 1.55 (s, 3H). LCMS: Expected: 191 (MH+); Found: 191.

UANOX006 (1,1-diethyl-3-(2-(indolin-1-yl)propyl)urea)

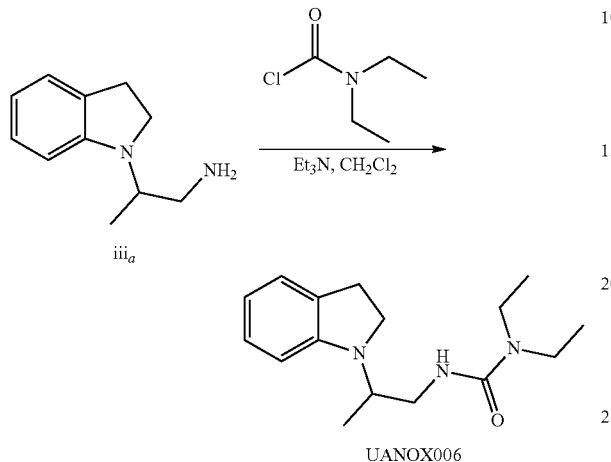

UANOX006 was synthesized as per the procedure described for compound UANOX001. $^1$H NMR (400 MHz, CDCl$_3$) δ 7.09-7.05 (m, 2H), 6.65 (t, J=8 Hz, 1H), 6.52 (d, J=8 Hz, 1H), 4.73 (bs, 1H), 3.93-3.81 (m, 1H), 3.60-3.54 (ddd, J=20, 12, 8 Hz, 1H), 3.34-3.29 (m, 2H), 3.33-3.31 (m, 5H), 3.24-3.91 (m, 2H), 1.14 (d, J=8 Hz, 3H), 1.06 (t, J=8 Hz, 6H). Minor conformer was also observed in proton NMR: $^1$H NMR (400 MHz, CDCl$_3$) δ 7.62 (dq, J=8, 0.8 Hz), 7.42 (dq, J=8, 0.8 Hz), 7.21 (d, J=3.6 Hz), 7.19 (dt, J=8, 1.2 Hz), 7.13 (dd, J=20, 1.2 Hz), 6.58 (d, J=3.6 Hz), 1.60 (d, J=8 Hz), 0.87 (t, J=8 Hz). HPLC-MS: Expected: 276 (MH+); Found: 276.

UANOX007 (N—(N,N-dimethylaminosulfonyl)-2-(indolin-1-yl)propane-1-amine)

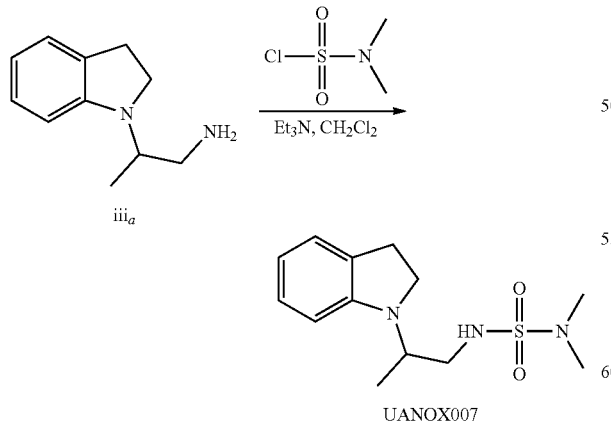

UANOX007 was synthesized as per the procedure described for compound UANOX001. $^1$H NMR (400 MHz, CDCl$_3$) δ 7.12-7.07 (m, 2H), 6.71 (t, J=8 Hz, 1H), 6.52 (d, J=8 Hz, 1H), 4.80 (bs, 1H), 3.93-3.84 (m, 1H), 3.40-3.26 (m, 2H), 3.19 (t, J=8 Hz, 2H). 3.02-2.98 (m, 2H), 2.82 (s, 6H), 1.11 (d, J=6.8 Hz, 3H). HPLC-MS: Expected: 284 (MH+); Found: 284.

UANOX008 (N-(2-(indolin-1-yl)propyl)pyrrolidine-1-sulfonamide)

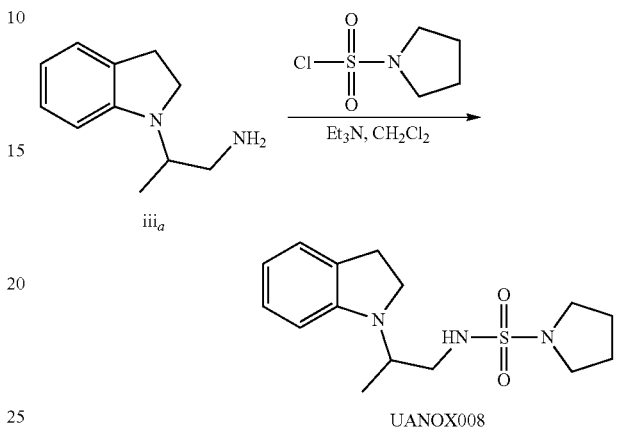

UANOX008 was synthesized as per the procedure described for compound UANOX001. 7.14-7.07 (m, 2H), 6.70 (t, J=8 Hz, 1H), 6.51 (d, J=8 Hz, 1H), 4.79-4.74 (m, 1H), 3.87 (sextet, J=7 Hz, 1H), 3.39-3.25 (m, 6H), 3.22-3.18 (m, 2H), 3.14 (t, J=8 Hz, 1H), 3.02-2.97 (m, 2H), 1.97-1.91 (m, 4H), 1.11 (d, J=6.4 Hz, 3H). HPLC-MS: Expected: 310 (MH+); Found: 310.

UANOX019 (N-(2-(indolin-1-yl)propyl)-4-methyl-piperazine-1-carboxamide)

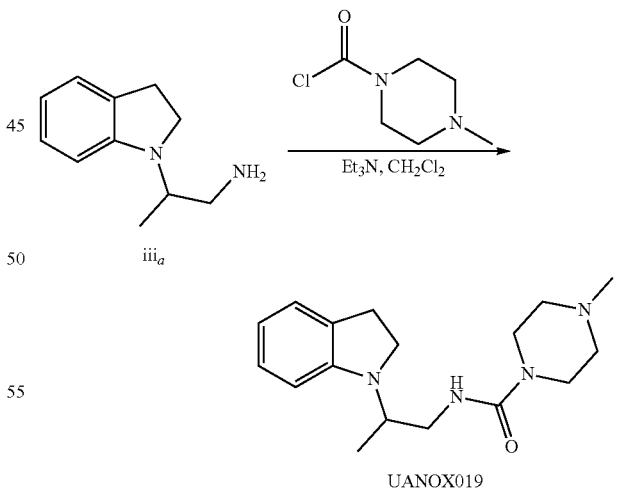

UANOX019 was synthesized as per the procedure described for compound UANOX001. $^1$H NMR (400 MHz, CDCl$_3$) δ 7.09-7.04 (m, 2H), 6.65 (t, J=8 Hz, 1H), 6.51 (d, J=8 Hz, 1H), 3.89-3.81 (m, 1H), 3.58-3.52 (ddd, J=20, 12, 8 Hz, 1H), 3.36-3.19 (m, 7H), 3.00-2.96 (m, 2H), 2.34 (t, J=5 Hz, 4H), 2.29 (s, 3H), 1.12 (d, J=8 Hz, 3H). HPLC-MS: Expected: 304 (M+2); Found: 304.

UANOX010 (N-(2-(indolin-1-yl)propyl)morpholine-4-sulfonamide)

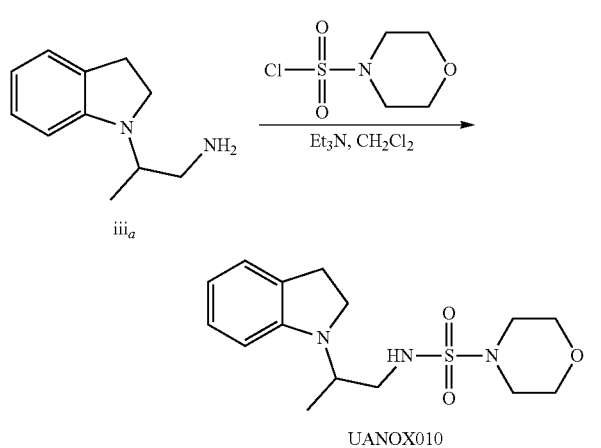

UANOX010 was synthesized as per the procedure described for compound UANOX001. $^1$H NMR (400 MHz, CDCl$_3$) δ 7.12 (d, J=8 Hz, 1H), 7.09 (t, J=8 Hz, 1H), 6.71 (t, J=8 Hz, 1H), 6.51 (d, J=8 Hz, 1H), 4.78 (t, J=8 Hz, 1H), 3.91-3.83 (m, 1H), 3.77 (t, J=8 Hz, 4H), 3.38-3.25 (m, 2H), 3.23-3.20 (m, 6H), 3.02-2.98 (m, 2H), 1.12 (d, J=8 Hz, 3H). HPLC-MS: Expected: 326 (MH$^+$); Found: 326 and Expected: 348 (M$^+$+Na); Found: 348.

UANOX020 (N-(2-(indolin-1-yl)propyl)pyrrolidine-1-carboxamide)

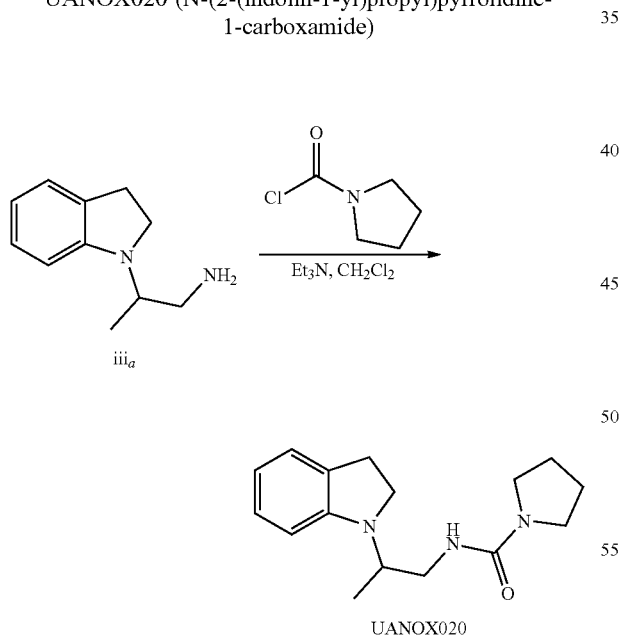

UANOX020 was synthesized as per the procedure described for compound UANOX001. $^1$H NMR (400 MHz, CDCl$_3$) δ 7.10-7.05 (m, 2H), 6.66 (t, J=8 Hz, 1H), 6.53 (d, J=8 Hz, 1H), 4.56 (bs, 1H), 3.92-3.84 (m, 1H), 3.62-3.56 (ddd, J=20, 12, 8 Hz, 1H), 3.42-3.31 (m, 2H), 3.27-3.19 (m, 5H), 3.02-2.97 (nm, 2H), 1.89-1.83 (m, 4H), 1.14 (d, J=8 Hz, 3H). HPLC-MS: Expected: 274 (MH$^+$); Found: 274.

UANOX009 (N-(2-(indolin-1-yl)propyl)piperidine-1-sulfonamide)

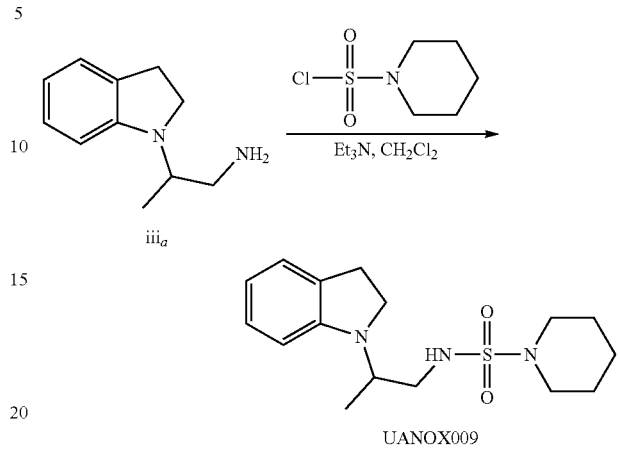

UANOX009 was synthesized as per the procedure described for compound UANOX001. $^1$H NMR (400 MHz, CDCl$_3$) δ 7.12-7.07 (m, 2H), 6.71 (t, J=8 Hz, 1H), 6.52 (d, J=8 Hz, 1H), 4.76 (t, J=8 Hz, 1H), 3.91-3.82 (m, 1H), 3.40-3.26 (m, 2H), 3.21-3.16 (m, 6H), 3.02-2.98 (m, 2H), 1.69-1.62 (m, 4H), 1.61-1.53 (m, 2H), 1.11 (d, J=6.8 Hz, 3H). HPLC-MS: Expected: 324 (MH$^+$); Found: 324.

UANOX033 (N-(2-(indolin-1-yl)propyl)-2-(pyridin-4-yl)thiazole-4-carboxamide)

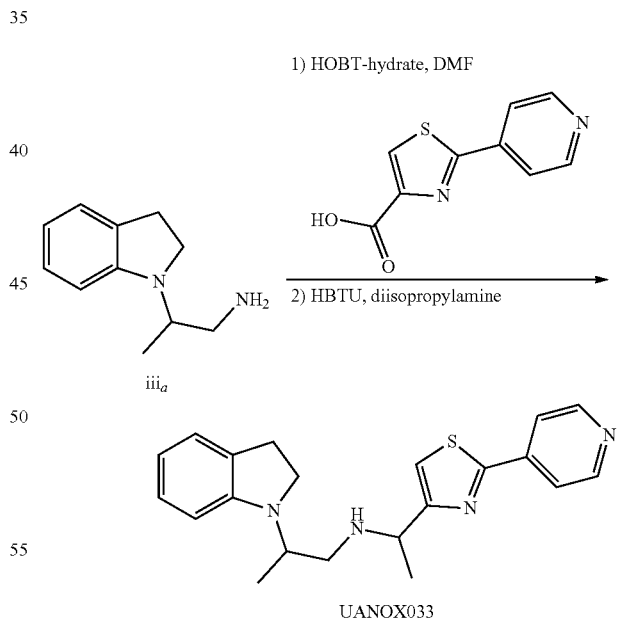

In a round bottomed flask equipped with a magnetic stir bar and a nitrogen inlet, a mixture of 2-(indolin-1-yl)propan-1-amine (iii) (0.15 g, 0.60 mmol), 2-(pyridin-4-yl)thiazole-4-carboxylic acid (0.149 g, 0.72 mmol) and HOBT-hydrate (0.11 g, 0.72 mmol) in 6 mL DMF were added. To the above solution, HBTU (0.27 g, 0.72 mmol) and diisopropylamine (0.28 mL, 1.60 mmol) were also added. The mixture was stirred at room temperature for 16 h. To the reaction mixture, aqueous saturated K₂CO₃ solution was added and then extracted with CH₂Cl₂. The combined organic layers were then washed with water, brine, dried over Na₂SO₄, and concentrated. The crude was purified by column chromatography with 0-2% MeOH in CH₂Cl₂. The compound was further purified by HPLC to give 20 mg (9%) of the pure and desired compound. ¹H NMR (400 MHz, CDCl₃) δ 8.71 (d, J=6 Hz, 2H), 8.22 (s, 1H), 7.71 (d, J=6 Hz, 2H), 7.68 (bs, NH), 7.11 (d, J=7 Hz, 1H), 7.07 (t, J=7 Hz, 1H), 6.66 (t, J=7 Hz, 1H), 6.56 (d, J=7 Hz, 1H), 4.06-3.97 (m, 1H), 3.79 (ddd, J=13.8, 7.0, 5.3 Hz, 1H), 3.62-3.31 (m, 3H), 3.04 (t, J=9 Hz, 2H), 1.24 (d, J=9 Hz, 3H). HPLC-MS: Expected: 365 (MH⁺); Found: 365.

UANOX034 (N-(2-(indolin-1-yl)propyl)-4-methoxybenzenesulfonamide)

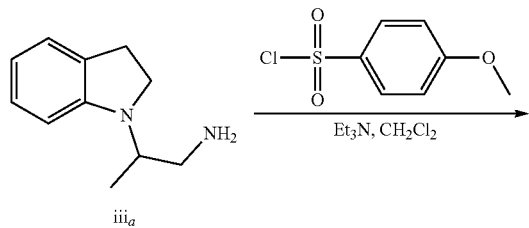

UANOX034 was synthesized as per the procedure described for compound UANOX001. ¹H NMR (400 MHz, CDCl₃) δ 7.82 (d, J=8 Hz, 2H), 7.09-7.04 (m, 2H), 7.01 (d, J=8 Hz, 2H), 6.69 (t, J=8 Hz, 1H), 6.31 (d, J=8 Hz, 1H), 4.94-4.91 (m, 1H), 3.92 (s, 3H), 3.73-3.64 (m, 1H), 3.20-3.11 (m, 2H), 3.06-2.96 (m, 2H), 2.94-2.84 (m, 2H), 1.01 (d J=8 Hz, 3H). HPLC-MS: Expected: 347 (MH⁺); Found: 347.

UANOX035 (4-fluoro-N-(2-(indolin-1-yl)propyl)benzenesulfonamide)

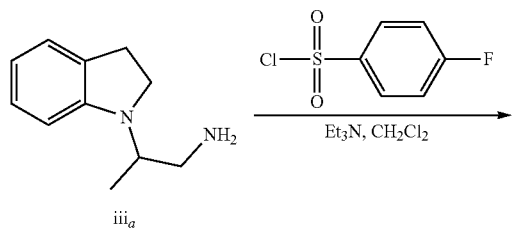

UANOX035 was synthesized as per the procedure described for compound UANOX001. ¹H NMR (400 MHz, CDCl₃) δ 7.93-7.89 (m, 2H), 7.22 (t, J=8 Hz, 2H), 7.09 (d, J=8 Hz, 1H), 7.05 (t, J=8 Hz, 1H), 6.71 (t, J=8 Hz, 1H), 6.32 (d, J=8 Hz, 1H), 4.98 (d, J=8 Hz, 1H), 3.75-3.66 (m, 1H), 3.23-3.13 (m, 2H), 3.08-2.86 (m, 4H), 1.03 (d J=8 Hz, 3H). HPLC-MS: Expected: 335 (MH⁺); Found: 335. The racemic mixture was separated by preparatory chiral HPLC.

Enantiomer A: ¹H NMR (400 MHz, CDCl₃) δ 7.92-7.89 (m, 2H), 7.21 (t, J=8 Hz, 2H), 7.09 (d, J=8 Hz, 1H), 7.07 (t, J=8 Hz, 1H), 6.69 (t, J=8 Hz, 1H), 6.32 (d, J=8 Hz, 1H), 5.07 (bs, 1H), 3.74-3.66 (m, 1H), 3.21-3.13 (m, 2H), 3.09-2.85 (m, 4H), 1.04 (d J=8 Hz, 3H). HPLC-MS: Expected: 335 (MH⁺); Found: 335.

Enantiomer B: ¹H NMR (400 MHz, CDCl₃) δ 7.92-7.89 (m, 2H), 7.21 (t, J=8 Hz, 2H), 7.09 (d, J=8 Hz, 1H), 7.07 (t, J=8 Hz, 1H), 6.69 (t, J=8 Hz, 1H), 6.32 (d, J=8 Hz, 1H), 5.07 (bs, 1H), 3.74-3.66 (m, 1H), 3.21-3.13 (m, 2H), 3.09-2.85 (m, 4H), 1.04 (d J=8 Hz, 3H). HPLC-MS: Expected: 335 (MH⁺); Found: 335.

UANOX037 (4-hydroxy-N-(2-(indolin-1-yl)propyl)piperazine-1-sulfonamide)

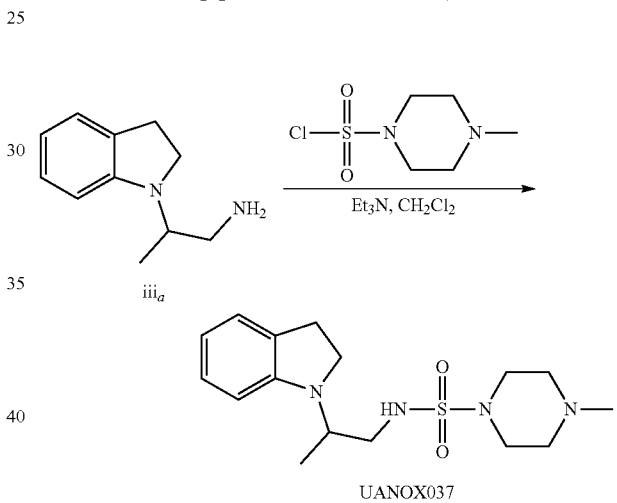

UANOX037 was synthesized as per the procedure described for compound UANOX001. ¹H NMR (400 MHz, CDCl₃) δ 7.11-7.07 (m, 2H), 6.70 (t, J=8 Hz, 1H), 6.51 (d, J=8 Hz, 1H), 5.14 (bs, 1H), 3.92-3.84 (m, 1H), 3.74 (bs, 4H), 3.40-3.34 (m, 2H), 3.19 (t, J=8 Hz, 2H), 2.99 (t, J=8 Hz, 2H), 2.75 (bs, 4H), 2.49 (bs, 3H), 1.11 (d, J=6.8 Hz, 3H). HPLC-MS: Expected: 339 (MH⁺); Found: 339.

UANOX049 (N-(2-(indolin-1-yl)propyl)-4-(trifluoromethoxy)benzenesulfonamide)

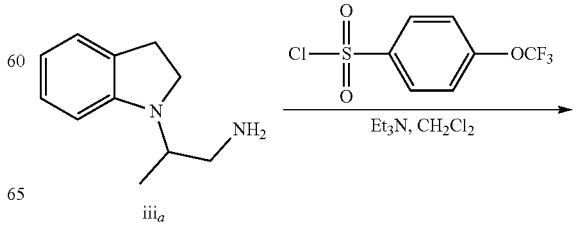

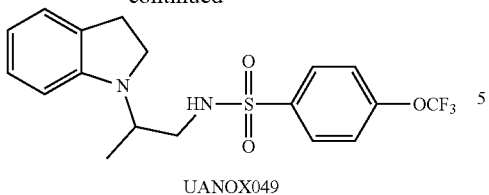

UANOX049

UANOX049 was synthesized as per the procedure described for UANOX001. ¹H NMR (400 MHz, CDCl₃) δ 7.93 (d, J=12 Hz, 2H), 7.35 (d, J=8 Hz, 2H), 7.08 (d, J=8 Hz, 1H), 7.04 (t, J=8 Hz, 1H), 6.70 (t, J=8 Hz, 1H), 6.30 (d, J=8 Hz, 1H), 5.17 (dd, J=8.4, 2.3 Hz, 1H), 3.74-3.66 (in, 1H), 3.32-3.13 (m, 2H), 3.09-3.00 (m, 2H), 2.97-2.84 (m, 2H), 1.05 (d, J=6.8 Hz, 3H). HPLC-MS: Expected: 401 (MH⁺); Found: 401.

UANOX048 (N-(2-(indolin-1-yl)propyl)-4-(trifluoromethyl)benzenesulfonamide)

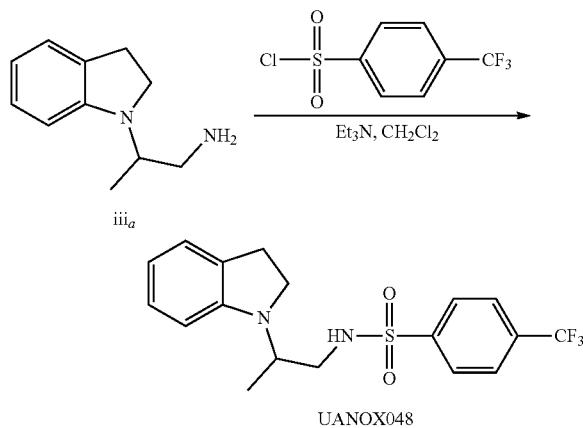

UANOX048

UANOX048 was synthesized as per the procedure described for UANOX001. ¹H NMR (400 MHz, Chloroform-d) δ 8.01 (d, J=7.6 Hz, 2H), 7.78 (d, J=8.2 Hz, 2H), 7.08 (d, J=8.3 Hz, 1H), 7.04 (t, J=7.1 Hz, 1H), 6.70 (t, J=7.8 Hz, 1H), 6.28 (d, J=7.9 Hz, 1H), 5.32-5.26 (m, 1H), 3.77-3.64 (m, 1H), 3.29-2.77 (m, 6H), 1.05 (d, J=6.7 Hz, 3H). HPLC-MS: Expected: 385 (MH⁺); Found: 385.

UANOX055 (N-(2-(indolin-1-yl)propyl)-2-phenylthiazole-4-carboxamide

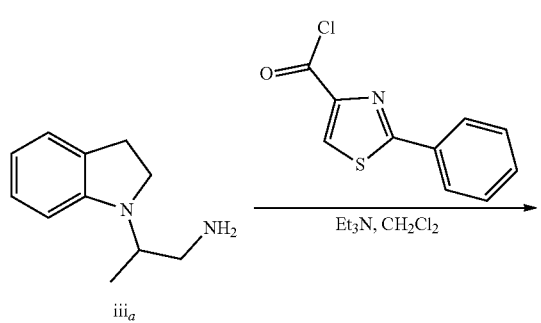

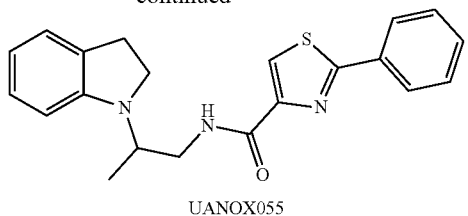

UANOX055

UANOX055 was synthesized as per the procedure described for UANOX001. ¹H NMR (400 MHz, CDCl₃) δ 8.10 (s, 1H), 7.90-7.87 (m, 2H), 7.71 (s, NH), 7.4-7.44 (m, 3H), 7.12-7.06 (m, 2H), 6.67 (t, J=8 Hz, 1H), 6.57 (d, J=8 Hz, 1H), 4.01 (dp, J=9.4, 6.6 Hz, 1H), 3.78 (ddd, J=13.7, 7.0, 5.6 Hz, 1H), 3.59-3.39 (m, 3H), 3.04 (t, J=8 Hz, 2H), 3.03 (d, J=8 Hz, 3H). HPLC-MS: Expected: 364 (MH⁺); Found: 364.

UANOX073 (4-fluoro-N-(2-(indolin-1-yl)propyl)benzenesulfonamide)

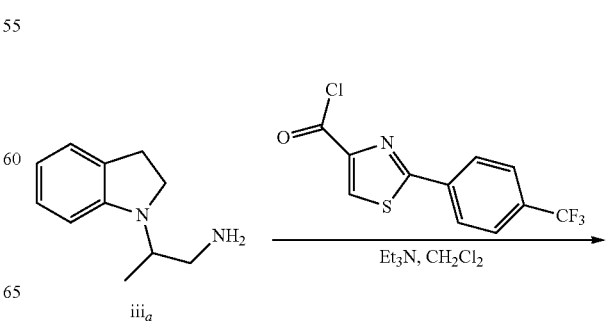

UANOX073

UANOX073 was synthesized as per the procedure described for UANOX001. ¹H NMR (400 MHz, Chloroform-d) δ 7.98 (d, J=8.7 Hz, 1H), 7.80 (d, J=8.7 Hz, 1H), 7.11-7.00 (m, 2H), 6.72 (t, J=7.8 Hz, 1H), 6.30 (d, J=7.9 Hz, 1H), 5.15 (d, J=6.9 Hz, 1H), 3.80-3.52 (m, 1H), 3.31-3.13 (m, 2H), 3.13-3.00 (m, 2H), 2.98-2.83 (m, 2H), 1.06 (d, J=6.7 Hz, 3H). HPLC-MS: Expected: 342 (MH⁺); Found: 342.

UANOX056 (N-(2-(indolin-1-yl)propyl)-2-(4-(trifluoromethyl)phenyl)thiazole-4-carboxamide)

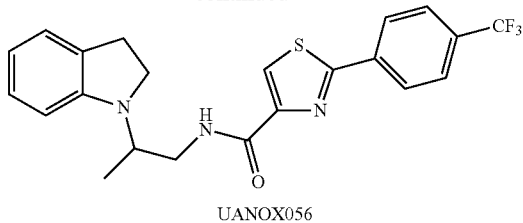

UANOX056

UANOX056 was synthesized as per the procedure described for UANOX001. $^1$H NMR (400 MHz, CDCl$_3$) δ 8.53 (s, 1H), 8.34 (d, J=8 Hz, 2H), 8.06 (d, J=12 Hz, 2H+1NH), 7.48 (d, J=8 Hz, 1H), 7.44 (t, J=8 Hz, 1H), 7.03 (t, J=8 Hz, 1H), 6.92 (d, J=8 Hz, 1H), 4.40-4.34 (m, 1H), 4.18-4.12 (m, 1H), 3.93-3.75 (m, 3H), 3.39 (d, J=8 Hz, 2H), 1.59 (d, J=8 Hz, 3H). HPLC-MS: Expected: 432 (MH$^+$); Found: 432.

UANOX054 (N-(2-(indolin-1-yl)propyl)-2-(4-(methoxy)phenyl)thiazole-4-carboxamide)

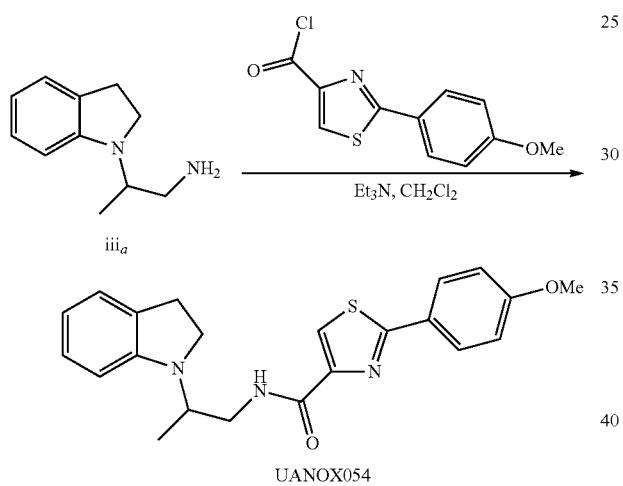

UANOX054

UANOX05 was synthesized as per the procedure described for UANOX001. $^1$H NMR (400 MHz, CDCl$_3$) δ 8.02 (s, 1H), 7.82 (d, J=8 Hz, 2H), 7.71 (s, NH), 7.11 (d, J=8 Hz, 1H), 7.09 (t, J=8 Hz, 1H), 6.96 (d, J=8 Hz, 2H), 6.66 (t, J=8 Hz, 1H), 6.57 (d, J=8 Hz, 1H), 4.03-3.97 (m, 1H), 3.89 (s, 3H), 3.81-3.74 (m, 1H), 3.58-3.39 (m, 3H), 3.04 (t, J=8 Hz, 2H), 1.23 (d, J=8 Hz, 3H). HPLC-MS: Expected: 394 (MH$^+$); Found: 394.

UANOX069 (N-(2-(indolin-1-yl)propyl)-2,3-dihydrobenzo[b][1,4]dioxine-6-sulfonamide)

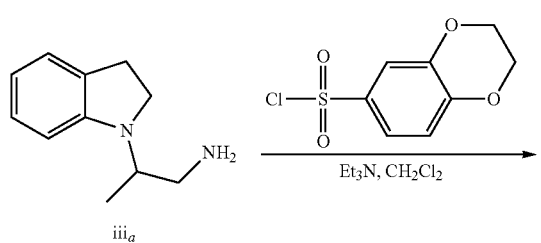

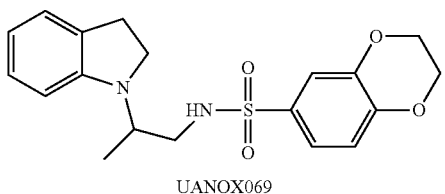

UANOX069

UANOX069 was synthesized as per the procedure described for UANOX001. $^1$H NMR (400 MHz, Chloroform-d) δ 7.42 (d, J=2.2 Hz, 1H), 7.37 (dd, J=8.5, 2.2 Hz, 1H), 7.13-7.02 (m, 2H), 6.98 (d, J=8.7 Hz, 1H), 6.69 (td, J=7.4, 0.9 Hz, 1H), 6.34 (d, J=7.9 Hz, 2H), 4.89 (d, J=8.8 Hz, 1H, NH), 4.41-4.20 (m, 4H), 3.76-3.66 (m, 1H), 3.21-3.10 (m, 2H), 3.06 (td, J=8.4, 4.4 Hz, 1H), 2.99 (ddd, J=12.7, 10.5, 2.4 Hz, 1H), 2.95-2.89 (m, 2H), 1.04 (d, J=6.7 Hz, 3H). HPLC-MS: Expected: 375 (MH$^+$); Found: 375.

UANOX071 (N-(2-(indolin-1-yl)propyl)-4-phenoxy-benzenesulfonamide)

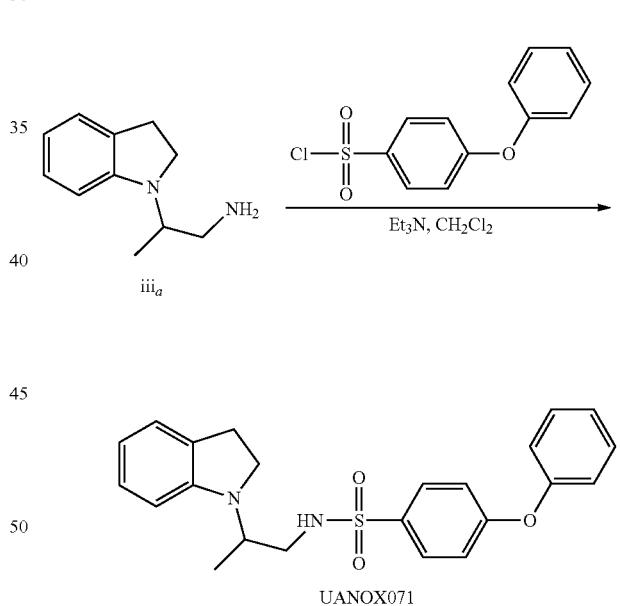

UANOX071

UANOX071 was synthesized as per the procedure described for UANOX001. $^1$H NMR (400 MHz, Chloroform-d) δ 7.84 (d, J=8.9 Hz, 2H), 7.45 (dd, J=8.5, 7.5 Hz, 2H), 7.28-7.21 (m, 1H), 7.13-7.01 (m, 6H), 6.70 (t, J=7.4 Hz, 1H), 6.33 (d, J=7.9 Hz, 1H), 4.97 (d, J=9.6 Hz, 1H, NH), 3.80-3.51 (m, 1H), 3.24-3.12 (m, 2H), 3.07 (dt, J=8.6, 4.0 Hz, 1H), 3.01 (dt, J=12.6, 10.4, 1H), 2.98-2.83 (m, 2H), 1.05 (d, J=6.7 Hz, 3H). HPLC-MS: Expected: 409 (MH$^+$); Found: 409.

UANOX070 (N-(2-(indolin-1-yl)propyl)-4-((5-(trifluoromethyl)pyridin-2-yl)oxy)benzenesulfonamide)

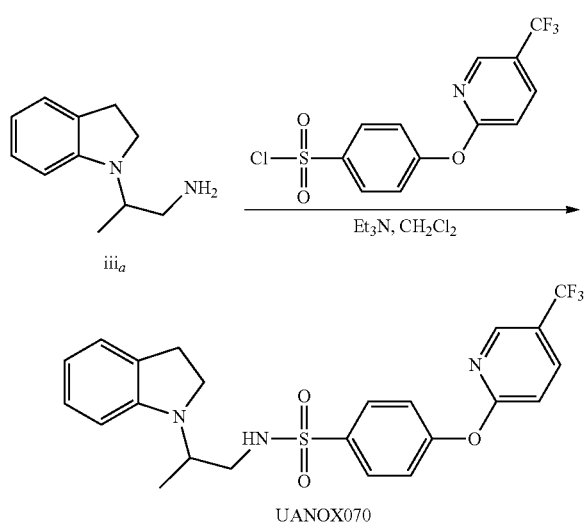

UANOX070 was synthesized as per the procedure described for UANOX001. $^1$H NMR (400 MHz, Chloroform-d) δ 8.47 (dt, J=2.6, 0.9 Hz, 1H), 8.01 (ddd, J=8.6, 2.5, 0.6 Hz, 1H), 7.95 (d, J=8.6 Hz, 2H), 7.33 (d, J=9.0 Hz, 2H), 7.15 (dp, J=8.6, 0.6 Hz, 1H), 7.09 (d, J=7.1 Hz, 1H), 7.04 (t, J=7.7 Hz, 1H), 6.71 (dd, J=7.4, 0.8 Hz, 1H), 6.37 (d, J=7.9 Hz, 1H), 5.02 (d, J=9.7 Hz, 1H, NH), 3.72 (dt, J=11.1, 6.8 Hz, 1H), 3.33-3.14 (m, 2H), 3.14-3.00 (m, 2H), 2.99-2.87 (m, 2H), 1.06 (d, J=6.7 Hz, 3H). HPLC-MS: Expected: 478 (MH$^+$); Found: 478.

UANOX072 (3,4-difluoro-N-(2-(indolin-1-yl)propyl)benzenesulfonamide)

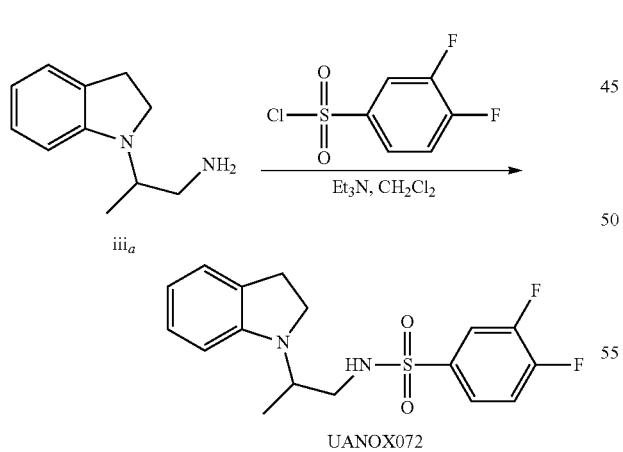

UANOX072 was synthesized as per the procedure described for UANOX001. $^1$H NMR (400 MHz, Chloroform-d) δ 7.73 (ddd, J=9.3, 7.2, 2.2 Hz, 1H), 7.70-7.63 (m, 1H), 7.33 (ddd, J=9.6, 8.6, 7.3 Hz, 1H), 7.12-7.02 (m, 2H), 6.71 (t, J=7.4 Hz, 1H), 6.35 (d, J=7.9 Hz, 1H), 5.07 (d, J=9.8 Hz, 1H, NH), 3.73 (dt, J=11.0, 6.8 Hz, 1H), 3.28-3.14 (m, 2H), 3.10 (td, J=8.7, 4.1 Hz, 1H), 3.02 (tdd, J=12.6, 10.4, 2.4 Hz, 1H), 2.96-2.89 (m, 2H), 1.06 (d, J=6.7 Hz, 3H). HPLC-MS: Expected: 353 (MH$^+$); Found: 353.

UANOX083 (N—(N,N-diethylaminosulfonyl)-2-(indolin-1-yl)-2-methylpropane-1-amine)

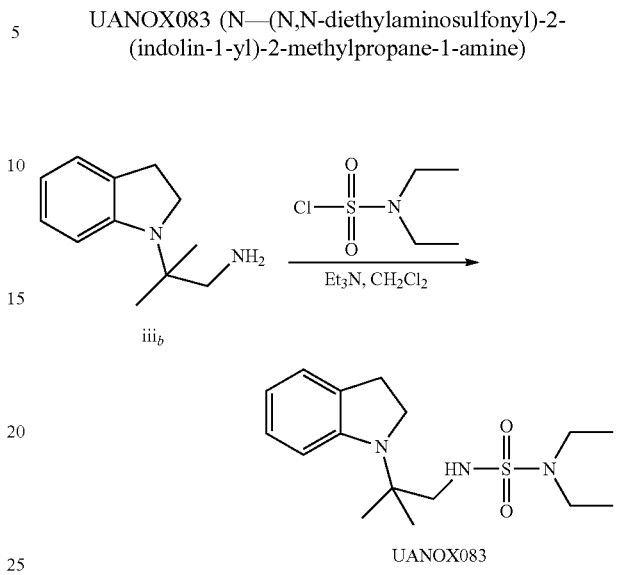

UANOX083 was synthesized as per the procedure described for UANOX001. $^1$H NMR (400 MHz, Chloroform-d) δ 6.69 (d, J=7.5 Hz, 1H), 6.61 (t, J=8.1 Hz, 1H), 6.45-6.02 (m, 2H), 4.25 (t, J=6.4 Hz, 1H), 3.00 (t, J=8.6 Hz, 2H), 2.93-2.74 (m, 6H), 2.49 (t, J=8.3 Hz, 2H), 0.95 (s, 6H), 0.78 (t, J=7.1 Hz, 6H). HPLC-MS: Expected: 326 (MH$^+$); Found: 326.

UANOX084 (N-(2-(indolin-1-yl)-2-methylpropyl)-4-(trifluoromethyl)benzenesulfonamide)

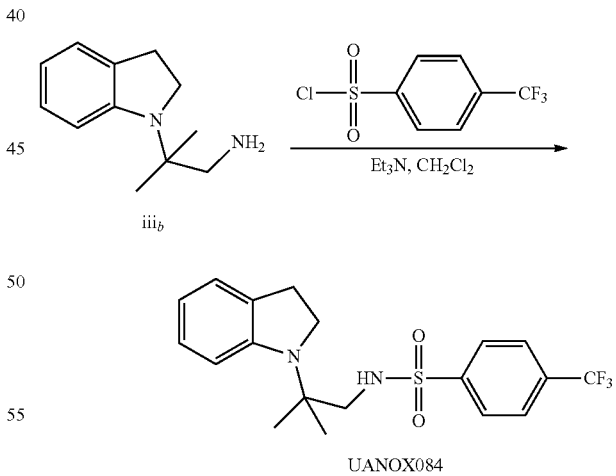

UANOX084 was synthesized as per the procedure described for UANOX001. $^1$H NMR (400 MHz, Chloroform-d) δ 7.81 (d, J=8.3 Hz, 2H), 7.62 (d, J=8.4 Hz, 2H), 6.95 (d, J=7.1 Hz, 1H), 6.63 (t, J=7.7 Hz, 1H), 6.56 (d, J=7.7 Hz, 1H), 6.06 (d, J=7.9 Hz, 1H), 5.02 (t, J=5.4 Hz, 1H), 3.24 (t, J=8.3 Hz, 2H), 3.12 (d, J=5.4 Hz, 2H), 2.76 (t, J=8.3 Hz, 2H), 1.19 (s, 6H). HPLC-MS: Expected: 399 (MH$^+$); Found: 399.

UANOX085 (N-(2-(indolin-1-yl)-2-methylpropyl)-4-phenoxybenzenesulfonamide)

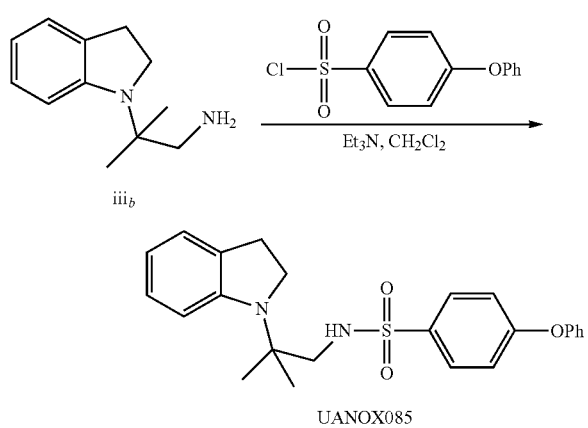

UANOX085 was synthesized as per the procedure described for UANOX001. $^1$H NMR (400 MHz, Chloroform-d) δ 7.98 (d, J=8.9 Hz, 2H), 7.67 (t, J=7.9 Hz, 2H), 7.52-7.43 (m, 1H), 7.33 (d, J=7.8 Hz, 2H), 7.29 (d, J=7.0 Hz, 1H), 7.24 (d, J=8.9 Hz, 2H), 7.06 (t, J=7.7 Hz, 1H), 6.89 (t, J=7.3 Hz, 1H), 6.51 (d, J=8.0 Hz, 1H), 5.20 (t, J=5.6 Hz, 1H), 3.59 (t, J=8.3 Hz, 2H), 3.44 (d, J=5.6 Hz, 2H), 3.11 (t, J=8.3 Hz, 2H), 1.53 (s, 6H). HPLC-MS: Expected: 423 (MH$^+$); Found: 423.

UANOX086 (4-fluoro-N-(2-(indolin-1-yl)-2-methylpropyl)benzenesulfonamide)

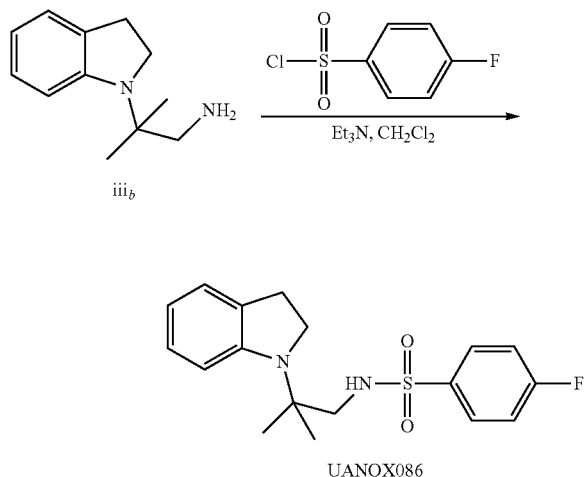

UANOX086 was synthesized as per the procedure described for UANOX001. $^1$H NMR (400 MHz, Chloroform-d) δ 7.85-7.81 (m, 2H), 7.18 (td, J=8.6, 2.6 Hz, 2H), 7.09 (d, J=7.0 Hz, 1H), 6.81 (t, J=7.9 Hz, 1H), 6.69 (td, J=7.4, 2.2 Hz, 1H), 6.24 (dd, J=8.1, 2.2 Hz, 1H), 5.02 (s, 1H), 3.37 (td, J=8.3, 2.5 Hz, 2H), 3.22 (dd, J=5.6, 2.6 Hz, 2H), 2.90 (t, J=8.0 Hz, 2H), 1.31 (s, 6H). HPLC-MS: Expected: 349 (MH$^+$); Found: 349.

UANOX087 (3,4-difluoro-N-(2-(indolin-1-yl)-2-methylpropyl)benzenesulfonamide)

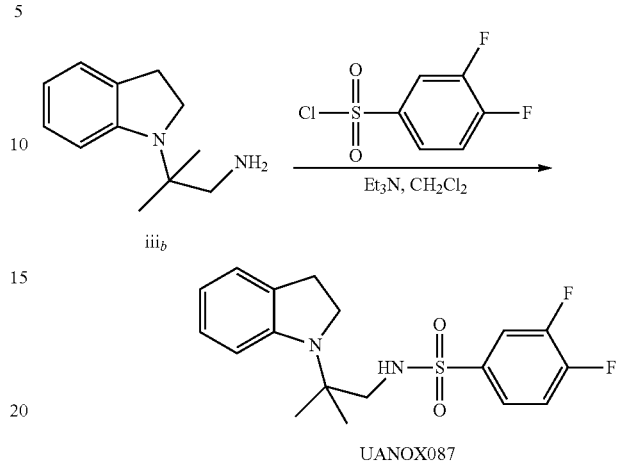

UANOX087 was synthesized as per the procedure described for UANOX001. $^1$H NMR (400 MHz, Chloroform-d) δ 7.69 (t, J=9.2 Hz, 1H), 7.67-7.58 (m, 1H), 7.31 (q, J=8.0 Hz, 1H), 7.13 (d, J=7.2 Hz, 1H), 6.86 (d, J=7.8 Hz, 1H), 6.73 (t, J=7.3 Hz, 1H), 6.30 (d, J=8.0 Hz, 1H), 5.13 (s, 1H), 3.41 (t, J=8.3 Hz, 2H), 3.27 (d, J=5.4 Hz, 2H), 2.93 (t, J=8.2 Hz, 2H), 1.35 (s, 6H). LCMS: Expected (M+H): 367 (M+H)$^+$ and 389 (M+Na)$^+$; Found: 367 and 389.

UANOX088 (N-(2-(indolin-1-yl)-2-methylpropyl)-4-(5-(trifluoromethyl)pyridin-2-yl)oxy)benzenesulfonamide)

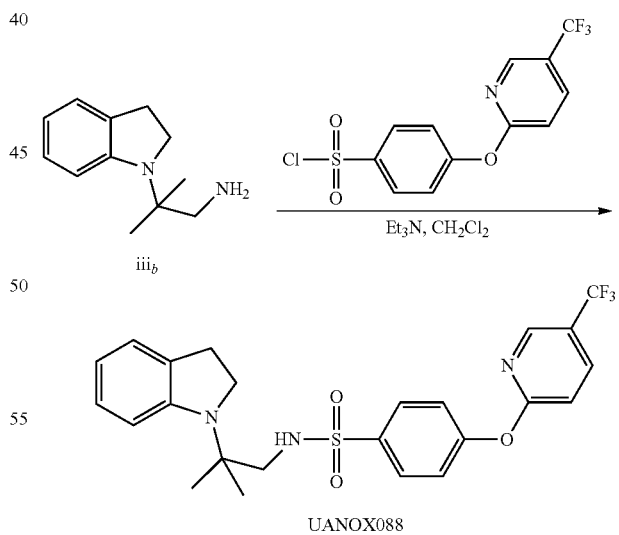

UANOX088 was synthesized as per the procedure described for UANOX001. $^1$H NMR (400 MHz, Chloroform-d) δ 8.42 (s, 1H), 7.94 (dd, J=8.5, 2.6 Hz, 1H), 7.81 (d, J=8.9 Hz, 2H), 7.26-7.20 (m, 2H), 7.08 (d, J=8.1 Hz, 1H), 7.02 (d, J=7.9 Hz, 1H), 6.81 (t, J=7.7 Hz, 1H), 6.61 (t, J=7.3 Hz, 1H), 6.23 (d, J=8.0 Hz, 1H), 4.94 (t, J=5.8 Hz, 1H), 3.32

(1, J=8.4 Hz, 2H), 3.20 (d, J=5.5 Hz, 2H), 2.84 (t, J=8.4 Hz, 2H), 1.26 (s, 6H). LCMS: Expected: 492 (MH⁺); Found: 492.

UANOX089 (N-(2-(indolin-1-yl)-2-methylpropyl)-4-methoxybenzenesulfonamide)

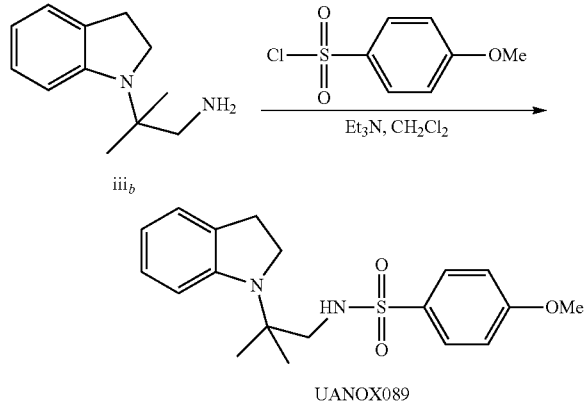

UANOX089 was synthesized as per the procedure described for UANOX001. ¹H NMR (400 MHz, Chloroform-d) δ 7.77 (d, J=10.7 Hz, 2H), 7.10 (d, J=7.3 Hz, 1H), 6.99 (d, J=7.2 Hz, 2H), 6.82 (t, J=8.0 Hz, 1H), 6.69 (t, J=7.8 Hz, 1H), 6.26 (d, J=7.9 Hz, 1H), 4.93 (t, J=5.5 Hz, 1H), 3.94 (s, 3H), 3.39 (t, J=8.7 Hz, 2H), 3.21 (d, J=7.1 Hz, 2H), 2.91 (t, J=8.3 Hz, 2H), 1.33 (s, 6H). LCMS: Expected: 361 (MH⁺); Found: 361.

UANOX090 (N-(2-(indolin-1-yl)-2-methylpropyl)-4-(trifluoromethoxy)benzenesulfonamide)

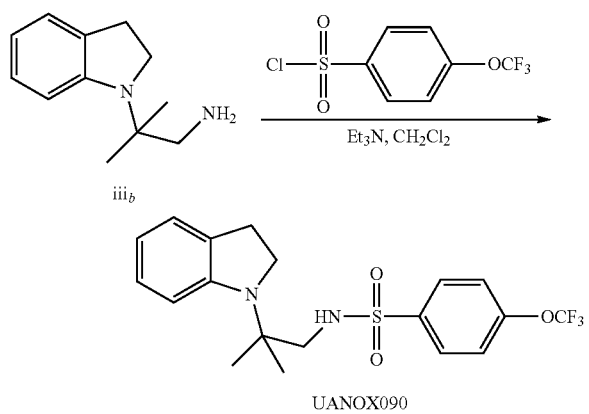

UANOX090 was synthesized as per the procedure described for UANOX001. ¹H NMR (400 MHz, Chloroform-d) δ 7.84 (d, J=8.5 Hz, 2H), 7.30 (d, J=8.3 Hz, 2H), 7.06 (d, J=7.1 Hz, 1H), 6.75 (d, J=7.8 Hz, 1H), 6.67 (d, J=7.3 Hz, 1H), 6.20 (d, J=8.0 Hz, 1H), 5.09 (s, 1H), 3.35 (t, J=8.3 Hz, 2H), 3.22 (d, J=5.4 Hz, 2H), 2.87 (t, J=8.3 Hz, 2H), 1.29 (s, 6H). LCMS: Expected: 415 (M+H) and 437 (M+Na); Found: 415 and 437.

Scheme 4

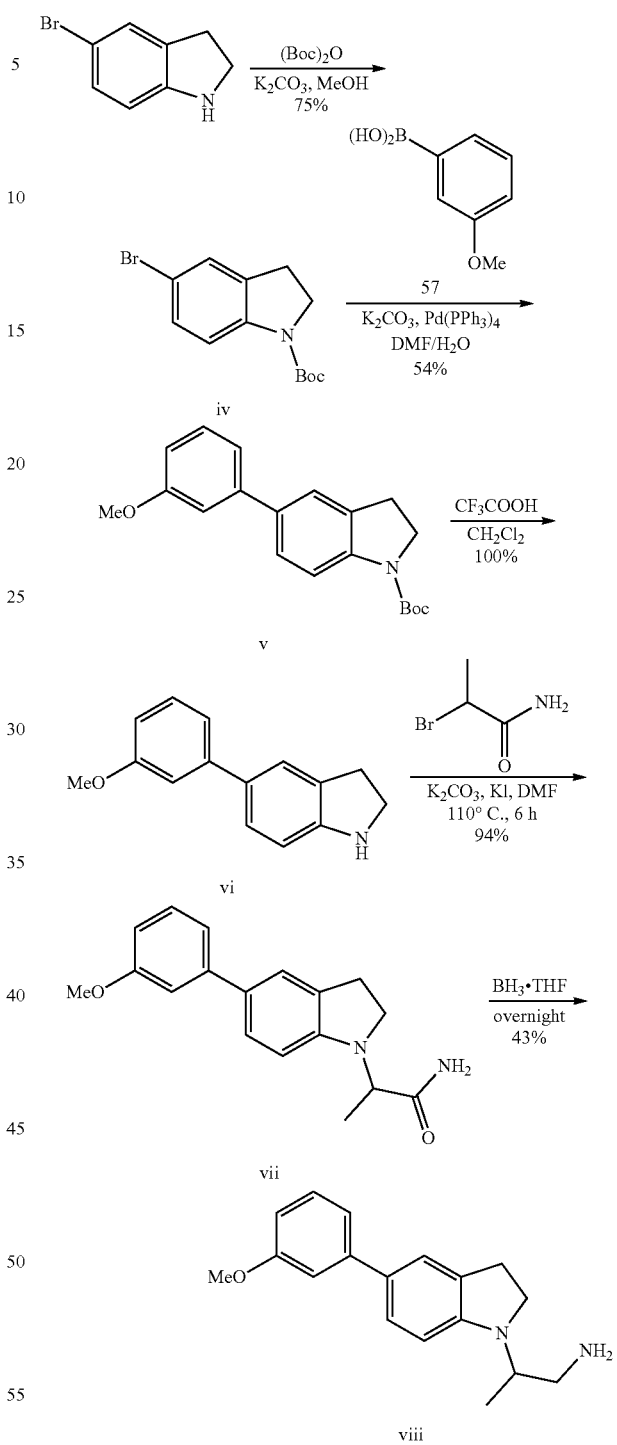

Synthesis of tert-butyl 5-bromoindoline-1-carboxylate (iv): To a round bottomed flask equipped with a nitrogen inlet and a magnetic stir bar, a solution of 5-bromoindoline (5 g, 25.24 mmol) in 200 mL MeOH was added. To the above solution, K₂CO₃ (4.2 g, 30.89 mmol) was added and then the reaction was stirred for 30 min followed by addition of boc anhydride (7.0 g, 32.07 mmol). The mixture was then stirred at room temperature for 72 hr, then diluted with water (300 mL). The aqueous mixture was extracted with CH₂Cl₂

(100 mL×3). The combined organic layers were dried over anhydrous $Na_2SO_4$, concentrated to obtain 7.25 g of crude. The crude was purified by column chromatography. The desired compound was eluted with 10-20% EtOAc in hexanes yielding 5.65 g (75%) of the desired product. $^1H$ NMR (400 MHz, $CDCl_3$) δ 7.28 (bs, 3H), 4.00 (t, J=8 Hz, 2H), 3.10 (t, J=8 Hz, 2H), 1.58 (s, 9H).

Synthesis of tert-butyl 5-(3-methoxyphenyl)indoline-1-carboxylate (v): In a round bottomed flask equipped with a magnetic stir bar and a nitrogen inlet, a solution of tert-butyl 5-bromoindoline-1-carboxylate (1.2 g, 4.04 mmol) and (3-methoxyphenyl)boronic acid (0.73 g, 4.80 mmol), $Na_2CO_3$ (0.852 g, 8.04 mmol) and $Pd(PPh_3)$. (0.464 g, 0.40 mmol) in 24 mL of $DMF/H_2O$ (1:1) were added. The reaction mixture was heated at 90° C. for 18 hr. The reaction mixture was then cooled to room temperature and 80 mL of water was added. The aqueous was then extracted with $CH_2Cl_2$ (50 mL×4), dried over $Na_2SO_4$, concentrated to yield 2.53 g black oil. The crude product was then purified by column chromatography with 10-20% EtOAc in hexanes to give 0.846 g (64%) of the desired compound as a white solid. $^1H$ NMR (400 MHz, Chloroform-d) δ 7.44-7.38 (m, 3H), 7.35 (t, J=7.9 Hz, 1H), 7.17 (ddd, J=7.7, 1.7, 1.0 Hz, 1H), 7.11 (dd, J=2.4, 1.7 Hz, 1H), 6.88 (ddd, J=8.2, 2.6, 0.9 Hz, 1H), 4.07 (t, J=8 Hz, 2H), 3.89 (s, 3H), 3.17 (t, J=8 Hz, 2H), 1.61 (s, 9H).

Synthesis of 5-(3-methoxyphenyl)indoline (vi): In a round bottomed flask equipped with a nitrogen inlet and a magnetic stir bar, the solution of tert-butyl 5-(4-methoxyphenyl)indoline-1-carboxylate (0.846 g, 2.6 mmol) in 40 mL $CH_2Cl_2$ was added. To the above solution, 11 mL $CF_3COOH$ was added and the mixture was stirred at room temperature for overnight. The reaction was monitored by TLC. After completion of reaction, solvent was removed. The residue was dissolved in water and then, saturated aqueous $Na_2CO_3$ solution was added to adjust pH=11. The aqueous layer was then extracted with $CH_2Cl_2$ (30 mL×3). The combined organic layers were concentrated and then dried in vacuo to give 0.60 mg (100%) of the desired product. $^1H$ NMR (400 MHz, $CDCl_3$) δ 7.40 (bs, 1H), 7.32 (quartet, J=8 Hz, 2H), 7.15 (dd, J=8 Hz, 2 Hz, $J_{meta}$=0.8 Hz, 1H), 7.10-7.09 (m, 1H), 6.68 (dd, J=8 Hz, 2.6 Hz, $J_{meta}$=0.8 Hz, 1H), 6.62 (d, J=8 Hz, 1H), 3.89 (s, 3H), 3.65 (t, J=8 Hz, 2H), 3.13 (t, J=8 Hz, 2H).

Synthesis of 2-(5-(3-methoxyphenyl)indolin-1-yl)propanamide (vii): To a round bottomed flask equipped with a nitrogen inlet and a reflux condenser, a solution of 5-(3-methoxyphenyl)indoline (829 mg, 3.68 mmol) in 7 mL DMF was added. To the above solution, $K_2CO_3$ (1.39 g, 10.1 mmol) was added and the reaction mixture was stirred for 30 min. Potassium iodide (70 mg, 0.42 mmol) and 2-bromopropionamide (616 mg, 1.71 mmol) were then added to the mixture and then heated at 110° C. or 2 hr. The reaction was cooled to room temperature and then diluted with 40 mL water. The aqueous mixture was extracted with $CH_2Cl_2$ (20 mL×3). The combined organic layers were dried over anhydrous $Na_2SO_4$ and concentrated to yield brown oil as crude. The crude was purified with 70% EtOAc in hexanes as eluent to give 1.024 g (94%) of the light brown oil as the desired product. $^1H$ NMR (400 MHz, $CDCl_3$) δ 7.39 (bs, 1H), 7.34-7.31 (m, 2H), 7.13 (ddd, J=7.6, 1.6, 0.9 Hz, 1H), 7.08-7.07 (m, 1H), 6.84 (ddd, J=8.2, 2.5, 0.8 Hz, 1H), 6.55 (d, J=8 Hz, 1H), 4.02 (quartet, J=8 Hz, 1H), 3.87 (s, 3H), 3.56 (quartet, J=8 Hz, 1H), 3.50 (quartet, J=8 Hz, 1H). 3.09 (t, J=8 Hz, 2H), 1.47 (d, J=8 Hz, 3H).

Synthesis of 2-(5-(3-methoxyphenyl)indolin-1-yl)propan-1-amine (viii): 2-(5-(3-Methoxyphenyl)indolin-1-yl) propanamide (6.83 mmol, 2.024 g) dissolved in 1M $BH_3$.THF (20 mL) was added to a round bottomed flask equipped with a nitrogen inlet and a reflux condenser. The reaction mixture was heated at reflux for 24 h. The reaction monitored by TLC. After the completion of reaction, the mixture was allowed to cool to room temperature and then quenched slowly with MeOH. The solution was concentrated, dissolved in MeOH, and again concentrated. The resulting oil was diluted with ether and extracted twice with 1 N HCl. The aqueous was treated with 2.5 N NaOH to adjust the pH >10 and extracted with chloroform. The combined chloroform extracts were dried over $Na_2SO_4$, and concentrated to provide yellow oil as crude. The crude was column chromatographed with 5% MeOH in $CH_2Cl_2$. The combined fractions containing the desired product were concentrated and then dried in vacuo yielding 820 mg (43%) of the product. $^1H$ NMR (400 MHz, $CDCl_3$) δ 7.35-7.29 (m, 3H), 7.13 (dd, J=8 Hz, 2 Hz, $J_{meta}$=0.8 Hz, 1H), 7.09-7.08 (m, 1H), 6.84 (dd, J=8 Hz, 3.6 Hz, $J_{meta}$=1.2 Hz, 1H), 6.55 (d, J=8 Hz, 1H), 3.88 (s, 3H), 3.75-3.66 (m, 1H), 3.48-3.36 (m, 2H), 3.06 (t, J=8 Hz, 2H), 2.94-2.78 (m, 2H), 1.12 (d, J=8 Hz, 3H).

UANOX036 (N-(2-(5-(3-methoxyphenyl)indolin-1-yl)propyl)-N,N-diethyl-1-sulfonamide)

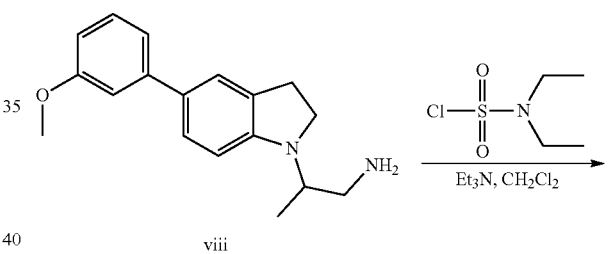

viii

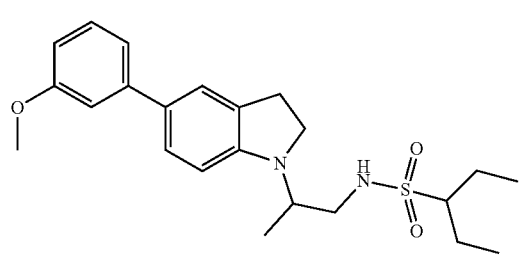

UANOX036

UANOX036 was synthesized as per the procedure described for UANOX001. $^1H$ NMR (400 MHz, $CDCl_3$) δ 7.35-7.33 (m, 3H), 7.14 (d, J=8 Hz, 1H), 7.08 (t, J=2.4 Hz, 1H), 6.84 (dd, J=7 Hz, 2.4 Hz, 1H), 6.56 (d, J=8 Hz, 1H), 4.60 (bs, 1H), 3.96-3.87 (m, 1H), 3.88 (s, 3H), 3.45-3.36 (m, 2H), 3.33 (quartet, J=6.8 Hz, 4H), 3.18-3.11 (m, 2H), 3.08-3.04 (m, 2H), 1.23 (t, J=8 Hz, 6H), 1.15 (d, J=6.8 Hz, 3H). HPLC-MS: Expected: 418 ($MH^+$); Found: 418.

UANOX0254 (N-(2-(5-(3-methoxyphenyl)indolin-1-yl)propyl)-4-methylpiperazine-1-sulfonamide)

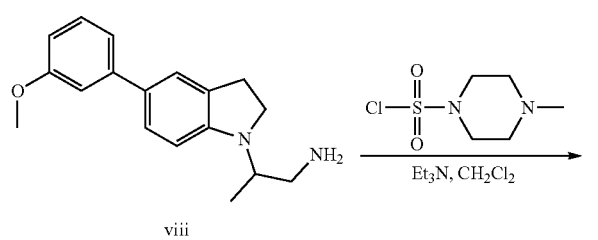

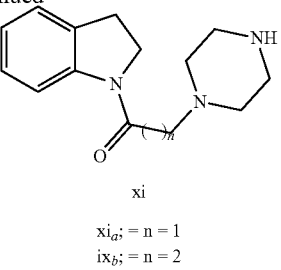

UANOX0254

UANOX0254 was synthesized as per the procedure described for UANOX001. $^1$H NMR (400 MHz, CDCl$_3$) δ 7.36-7.32 (m, 2H), 7.30 (bs, 1H), 7.14 (dd, J=8 Hz, 2 Hz, $J_{meta}$=0.8 Hz, 1H), 7.09-7.08 (m, 1H), 6.82 (dd, J=7 Hz, 2.4 Hz, 1H), 3.91 (t, J=8 Hz, 1H), 3.88 (s, 3H), 3.44-3.32 (m, 2H), 3.29 (t, J=5 Hz, 4H), 3.22 (t, J=6.8 Hz, 2H), 3.08-3.04 (m, 2H), 2.51 (t, J=8 Hz, 4H), 2.35 (s, 3H), 1.15 (d, J=8 Hz, 3H). HPLC-MS: Expected: 445 (MH$^+$); Found: 445.

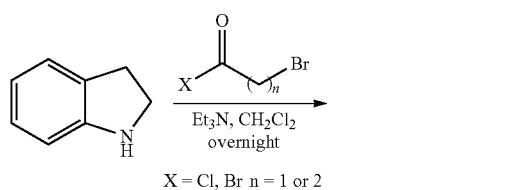

X = Cl, Br  n = 1 or 2

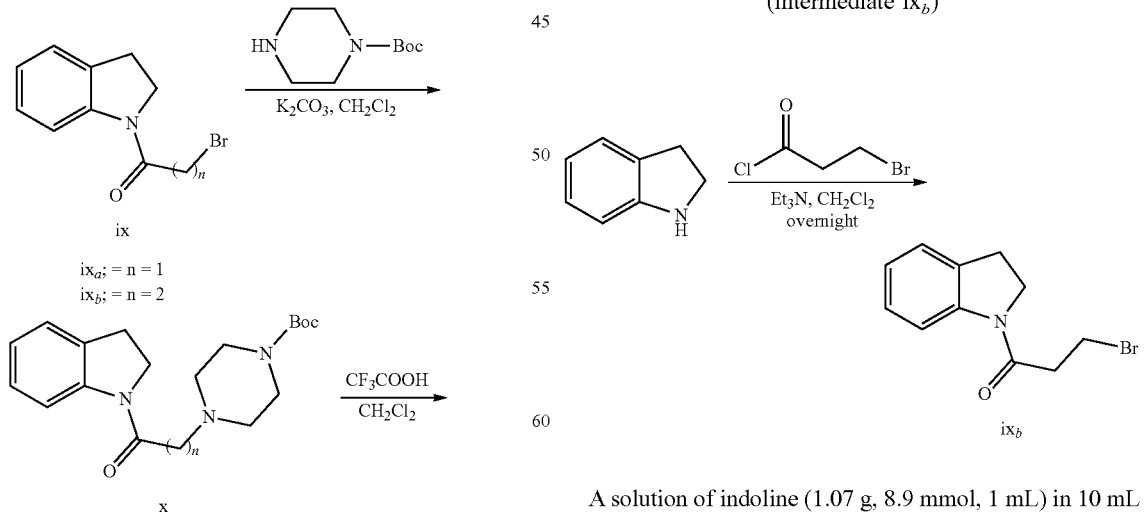

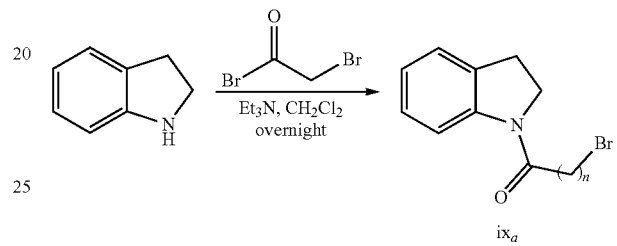

Scheme 5
Synthesis of 2-bromo-1-(indolin-1-yl)ethan-1-one (intermediate ix$_a$)

To a round bottomed flask equipped with a nitrogen inlet and a magnetic stir bar, a solution of indoline (1.07 g, 8.9 mmol, 1 mL) in 10 mL CH$_2$Cl$_2$ was added. To the above solution, Et$_3$N (0.90 g, 1.24 mmol) and 2-bromoacetyl bromide (1.8 g. 0.78 mL, 8.9 mmol) were subsequently added. The mixture was stirred at room temperature for overnight. The mixture was then concentrated. The residue was washed with water and then with Et$_2$O, dried in vacuo yielding 2.12 g (99%) of the desired product. $^1$H NMR (400 MHz, CDCl$_3$) δ 8.10 (d, J=8 Hz, 1H), 7.27 (d, J=8 Hz, 1H), 7.19 (quartet, J=8 Hz, 1H), 7.09 (t, J=8 Hz, $J_{meta}$=1.2 Hz, 1H), 4.25 (t, J=8 Hz, 2H), 4.15 (s, 2H), 3.23 (t, J=8 Hz, 2H). HPLC-MS: Expected: 364 (MH$^+$); Found: 364.

Synthesis of 3-bromo-1-(indolin-1-yl)propan-1-one (intermediate ix$_b$)

A solution of indoline (1.07 g, 8.9 mmol, 1 mL) in 10 mL CH$_2$Cl$_2$ was added to a round bottom flask equipped with a nitrogen inlet and a magnetic stir bar. To the above solution, Et$_3$N (0.90 g, 1.24 mmol) and 3-bromopropanoyl chloride (1.53 g, 0.9 mL, 8.9 mmol) were subsequently added. The mixture was stirred at room temperature for overnight. The mixture was then concentrated to give 2.92 g of crude product. The residue was washed with water and then washed with Et$_2$O, dried in vacuo yielding 2.4 g (100%) of crude which was used in the next step as it is. $^1$H NMR (400 MHz, CDCl$_3$) δ 8.13 (d, J=8 Hz, 1H), 7.25 (d, J=8 Hz, 1H), 7.18 (t, J=8 Hz, 1H), 7.04 (t, J=8 Hz, 1H), 4.16 (t, J=8 Hz, 2H), 3.74 (t, J=8 Hz, 2H), 3.32 (t, J=8 Hz, 2H), 3.15 (t, J=8 Hz, 2H). HPLC-MS: Expected: 254 (MH$^+$); Found: 254.

Synthesis of tert-butyl 4-(2-(indolin-1-yl)-2-oxo-ethyl)piperazine-1-carboxylate (intermediate x$_a$)

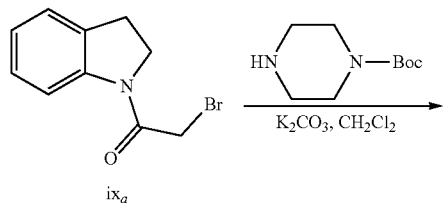

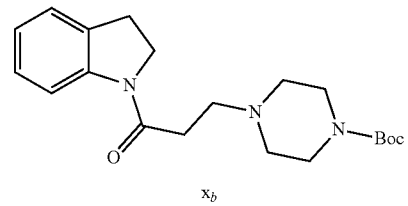

In a round bottomed flask equipped with a nitrogen inlet and a magnetic stir bar, the solution of 2-bromo-1-(indolin-1-yl)ethan-1-one (0.2 g, 0.83 mmol) in 5 mL CH$_2$Cl$_2$ was added. To the above solution, K$_2$CO$_3$ (0.29 g, 2.10 mmol) and tert-butyl piperazine-1-carboxylate (0.31 g, 1.67 mmol) were added. The mixture was stirred at room temperature for overnight and then washed with water (15 mL). The aqueous layer was then extracted with CH$_2$Cl$_2$ (10 mL×3). The combined organic layers were concentrated and the crude was purified using column chromatography. The desired product was eluted with 2% MeOH in CH$_2$Cl$_2$ to yield 176 mg (61%) of the desired product. $^1$H NMR (400 MHz, CDCl$_3$) δ 8.24 (d, J=8 Hz, 1H), 7.23-7.19 (m, 2H), 7.04 (t, J=8 Hz, 1H), 4.16 (t, J=8 Hz, 2H), 3.50 (t, J=8 Hz, 4H), 3.28 (s, 2H), 3.21 (t, J=8 Hz, 2H), 2.58 (t, J=8 Hz, 4H), 1.61 (s, 9H). HPLC-MS: Expected: 346 (MH$^+$); Found: 346.

Synthesis of tert-butyl 4-(3-(indolin-1-yl)-3-oxopropyl)piperazine-1-carboxylate (intermediate x$_b$)

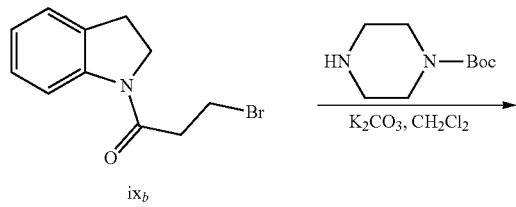

Compound x$_b$ was synthesized as per the procedure described for compound x$_a$. $^1$H NMR (400 MHz, CDCl$_3$) δ 8.24 (d, J=8 Hz, 1H), 7.24-7.20 (m, 2H). 7.04 (t, J=8 Hz, 1H), 4.10 (t, J=8 Hz, 2H), 3.47 (t, J=8 Hz, 4H), 3.24 (t, J=8 Hz, 2H), 2.88 (t, J=8 Hz, 2H), 2.67 (t, J=8 Hz, 2H), 2.50 (t, J=8 Hz, 4H), 1.61 (s, 9H). HPLC-MS: Expected: 360 (MH$^+$); Found: 360.

Synthesis of 1-(indolin-1-yl)-2-(piperazin-1-yl)ethan-1-one (intermediate xi$_a$)

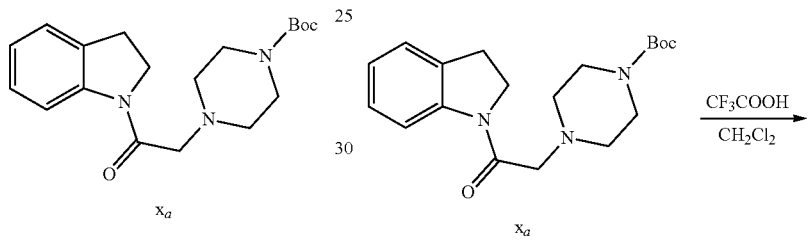

In a round bottomed flask equipped with a nitrogen inlet and a magnetic stir bar, a solution of 3-bromo-1-(indolin-1-yl)propan-1-one (1.1 g, 4.58 mmol) in 25 mL CH$_2$Cl$_2$ was added. To the above solution, K$_2$CO$_3$ (1.56 g, 11.30 mmol) and tert-butyl piperazine-1-carboxylate (1.70 g, 9.16 mmol) were added. The mixture was stirred at room temperature for overnight and then dissolved in 35 mL water. The aqueous layer was then extracted with CH$_2$Cl$_2$ (25 mL×3). The combined organic layers were concentrated to yield 1.86 g of crude. The crude was purified by column chromatography and the desired product was eluted with 2% MeOH in CH$_2$Cl$_2$ to yield 1.46 g (92%) of the desired product. $^1$H NMR (400 MHz, CDCl$_3$) δ 8.25 (d, J=8 Hz, 1H), 7.24-7.21 (m, 2H), 7.06 (t, J=8 Hz, 1H), 4.19 (t, J=8 Hz, 2H), 3.52 (t, J=8 Hz, 4H), 3.30 (s, 2H), 3.23 (t, J=8 Hz, 2H), 2.59 (t, J=8 Hz, 4H). HPLC-MS: Expected: 246 (MH$^+$); Found: 246.

Synthesis of 1-(indolin-1-yl)-3-(piperazin-1-yl)propan-1-one (intermediate xi$_b$)

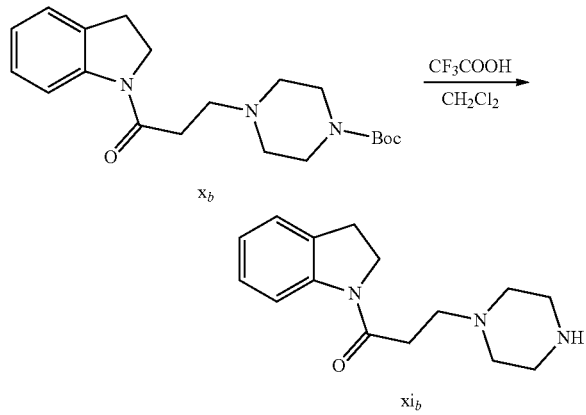

A solution of tert-butyl 4-(3-(indolin-1-yl)-3-oxopropyl)piperazine-1-carboxylate (1.2 g, 3.34 mmol) in 50 mL CH$_2$Cl$_2$ was added to a round bottomed flask equipped with a nitrogen inlet and a magnetic stir bar. To the above solution 12 mL CF$_3$COOH was added and the mixture was stirred at room temperature for overnight. The mixture was then adjusted to pH 11 with saturated aqueous Na$_2$CO$_3$ soln, and the layers were then separated. The aqueous layer was then extracted with CH$_2$Cl$_2$ (40 mL×3). The combined organic layers were concentrated to yield 0.78 g (90%) of the desired product. $^1$H NMR (400 MHz, Chloroform-d) δ 8.26 (d, J=8.2 Hz, 1H), 7.22 (t, J=7.9 Hz, 2H), 7.12-6.96 (m, 1H), 4.21 (t, J=8.5 Hz, 2H), 3.23 (t, J=8.5 Hz, 2H), 3.02-2.93 (m, 4H), 2.66-2.58 (m, 4H), 1.86-1.75 (m, 4H). HPLC-MS: Expected: 260 (MH$^+$); Found: 260.

UANOX028 (4-(2-(indolin-1-yl)-2-oxoethyl)-N,N-dimethylpiperazine-1-sulfonamide)

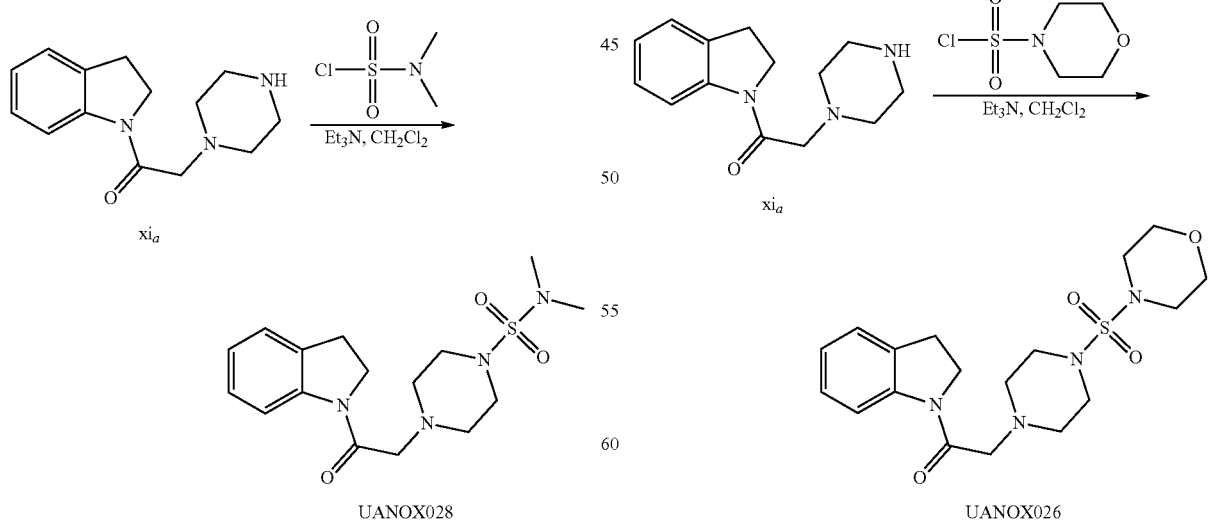

UANOX02 was synthesized as per the procedure described for UANOX001. $^1$H NMR (400 MHz, CDCl$_3$) δ 8.21 (d, J=8 Hz, 1H), 7.20-7.17 (m, 2H), 7.04 (t, J=8 Hz, 1H), 4.11 (t, J=8 Hz, 2H), 3.33 (t, J=8 Hz, 4H), 3.29 (s, 2H), 3.20 (t, J=8 Hz, 2H), 2.83 (s, 6H), 2.68 (t, J=8 Hz, 4H). HPLC-MS: Expected: 353 (MH$^+$); Found: 353.

UANOX025 (N,N-diethyl-4-(2-(indolin-1-yl)-2-oxoethyl)piperazine-1-sulfonamide)

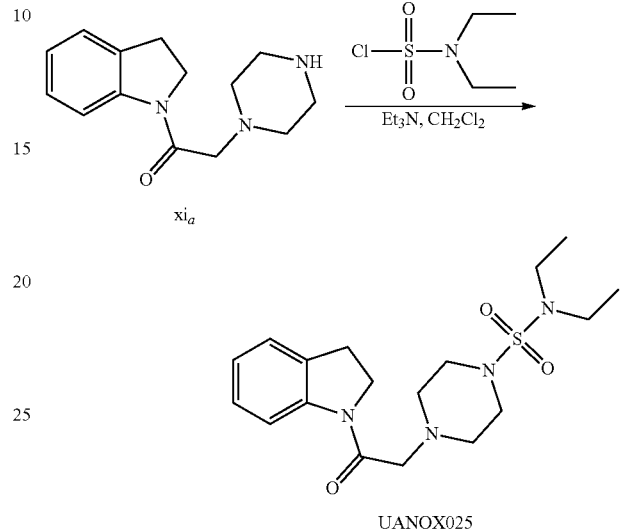

UANOX025 was synthesized as per the procedure described for UANOX001. $^1$H NMR (400 MHz, CDCl$_3$) δ 8.21 (d, J=8 Hz, 1H), 7.21-7.17 (m, 2H), 7.03 (t, J=8 Hz, 1H), 4.13 (t, J=8 Hz, 2H), 3.30-3.25 (m, 10H), 3.20 (t, J=8 Hz, 2H), 2.68 (t, J=8 Hz, 4H), 1.16 (t, J=7 Hz, 6H). HPLC-MS: Expected: 381 (MH$^+$); Found: 381.

UANOX026 (1-(indolin-1-yl)-2-(4-(morpholinosulfonyl)piperazin-1-yl)ethan-1-one)

UANOX026 was synthesized as per the procedure described for UANOX001. $^1$H NMR (400 MHz, CDCl$_3$) δ 8.24 (d, J=8 Hz, 1H), 7.24-7.21 (m, 2H), 7.06 (t, J=8 Hz, 1H), 4.14 (t, J=8 Hz, 2H), 3.75 (t, J=5 Hz, 4H), 3.39 (t, J=5 Hz, 4H), 3.34 (s, 2H), 3.26 (t, J=8 Hz, 4H), 3.24 (t, J=8 Hz, 2H, 2.73 (t, J=8 Hz, 4H). HPLC-MS: Expected: 395 (MH⁺); Found: 395.

UANOX027 (1-(indolin-1-yl)-2-(4-(piperidin-1-ylsulfonyl)piperazin-1-yl)ethan-1-one)

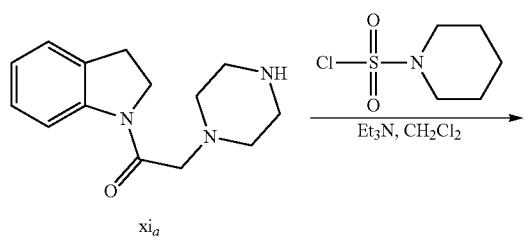

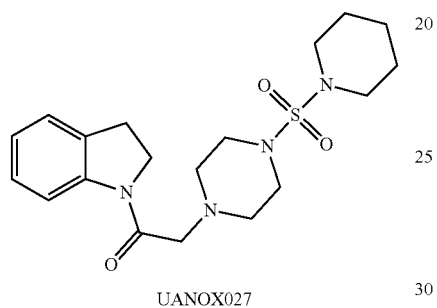

UANOX027 was synthesized as per the procedure described for UANOX001. ¹H NMR (400 MHz, CDCl₃) δ 8.23 (d, J=8 Hz, 1H), 7.22-7.18 (m, 2H), 7.04 (t, J=8 Hz, 1H), 4.13 (t, J=8 Hz, 2H), 3.34-3.30 (m, 6H), 3.25-3.19 (m, 6H), 2.69 (t, J=8 Hz, 4H), 1.65-1.60 (m, 4H), 1.58-1.53 (m, 2H). HPLC-MS: Expected: 393 (MH⁺); Found: 393.

UANOX0192 (1-(indolin-1-yl)-2-(4-(pyrimidin-2-yl)piperazin-1-yl)ethan-1-one)

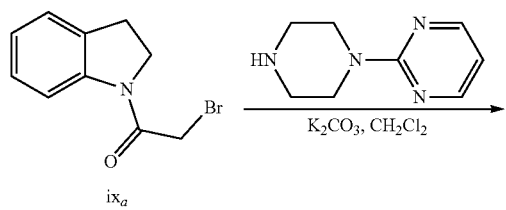

In a round bottomed flask equipped with a nitrogen inlet and a magnetic stir bar, the solution of 2-bromo-1-(indolin-1-yl)ethan-1-one (0.2 g, 0.83 mmol) in 5 mL CH₂Cl₂ was added. To the above solution, K₂CO₃ (0.29 g, 2.10 mmol) and 2-(piperazin-1-yl)pyrimidine (0.27 g, 1.64 mmol) were also added. The mixture was stirred at room temperature for overnight and then washed with 15 mL water. The aqueous layer was then extracted with CH₂Cl₂ (10 mL×3). The combined organic layers were concentrated to give crude product. The crude was purified using column chromatography with 2% MeOH in CH₂Cl₂ to yield 120 mg (45%) of the desired product. The fraction obtained was further purified using same condition to give 106 mg of the pure and desired product. ¹H NMR (400 MHz, CDCl₃) δ 8.33 (d, J=4 Hz, 2H), 8.27 (d, J=8 Hz, 1H), 7.25-7.21 (m, 2H), 7.05 (t, J=8 Hz, 1H), 6.50 (t, 0.1=4 Hz, 1H), 4.21 (t, J=4 Hz, 2H), 3.92 (t, J=8 Hz, 4H), 3.33 (s, 2H), 3.24 (t, J=8 Hz, 2H), 2.71 (t, J=8 Hz, 4H). HPLC-MS: Expected: 324 (MH⁺); Found: 324.

UANOX032 (4-(3-(indolin-1-yl)-3-oxopropyl)-N,N-dimethylpiperazine-1-sulfonamide)

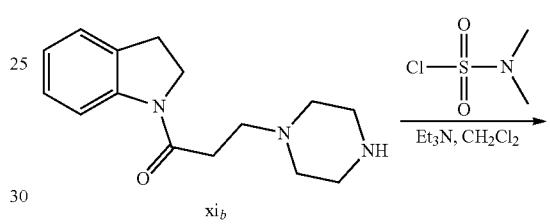

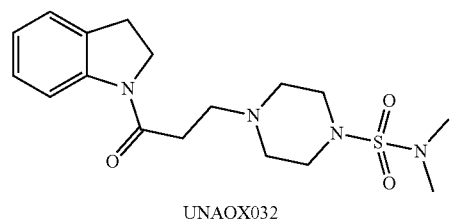

UANOX032 was synthesized as per the procedure described for UANOX001. ¹H NMR (400 MHz, CDCl₃) δ 8.22 (d, J=8 Hz, 1H), 7.23-7.19 (m, 2H), 7.04 (t, J=8 Hz, 1H), 4.09 (t, J=8 Hz, 2H), 3.30 (t, J=5 Hz, 4H), 3.23 (t, J=8 Hz, 2H), 2.90 (t, J=8 Hz, 2H), 2.86 (s, 6H), 2.65 (t, J=5 Hz, 2H), 2.60 (t, J=5 Hz, 4H). HPLC-MS: Expected: 367 (MH⁺); Found: 367.

UANOX029 (N,N-diethyl-4-(3-(indolin-1-yl)-3-oxopropyl)piperazine-1-sulfonamide)

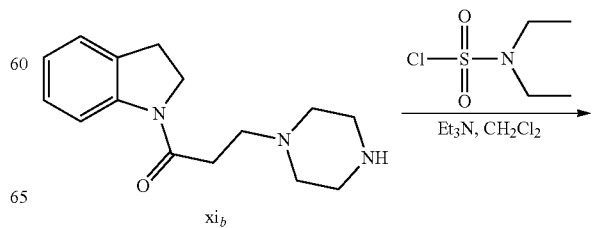

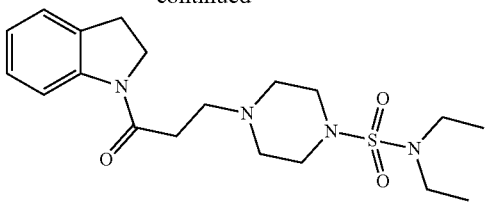

UNAOX029

UANOX029 was synthesized as per the procedure described for UANOX001. $^1$H NMR (400 MHz, CDCl$_3$) δ 8.23 (d, J=8 Hz, 1H), 7.21-7.19 (m, 2H), 7.04 (t, J=8 Hz, 1H), 4.09 (t, J=8 Hz, 2H), 3.29 (quartet, J=8 Hz, 4H), 3.35-3.21 (m, 6H), 2.89 (t, J=8 Hz, 2H), 2.65 (t, J=8 Hz, 2H), 2.60 (d, J=8 Hz, 4H), 1.21 (t, J=8 Hz, 6H). HPLC-MS: Expected: 395 (MH$^+$); Found: 395.

UANOX030 (1-(indolin-1-yl)-3-4-(morpholinosulfonyl)piperazin-1-yl)propan-1-one)

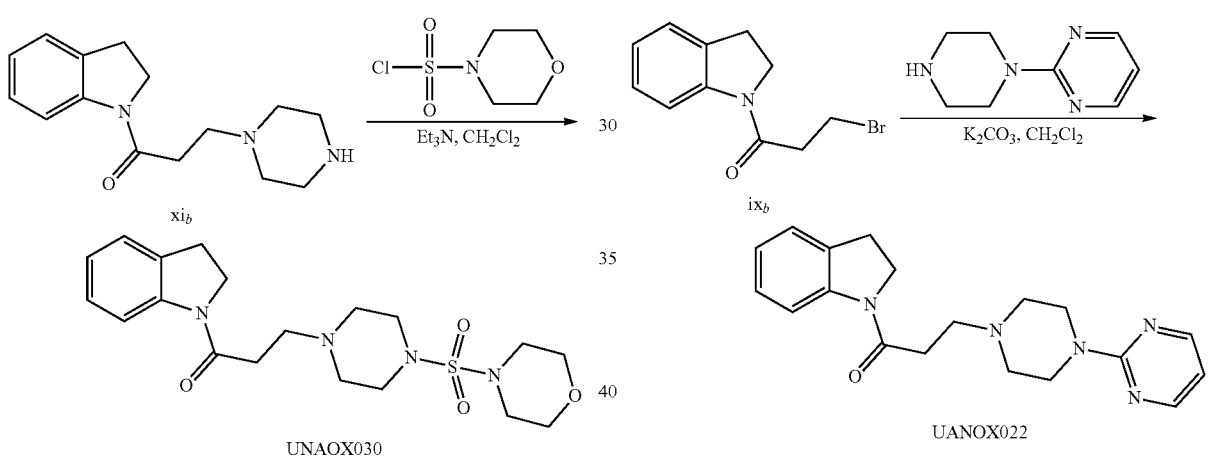

UNAOX030

UANOX030 was synthesized as per the procedure described for UANOX001. $^1$H NMR (400 MHz, CDCl$_3$) δ 8.23 (d, J=8 Hz, 1H), 7.24-7.20 (m, 2H), 7.04 (t, J=8 Hz, 1H), 4.10 (t, J=8 Hz, 2H), 3.76-3.74 (m, 4H), 3.33 (t, J=8 Hz, 4H), 3.27-3.22 (m, 6H), 2.91 (t, J=8 Hz, 2H), 2.66 (t, J=8 Hz, 2H), 2.61 (t, J=5 Hz, 4H). HPLC-MS: Expected: 409 (MH$^+$); Found: 409.

UANOX031 (1-(indolin-1-yl)-3-(4-(piperidin-1-ylsulfonyl)piperazin-1-yl)propan-1-one)

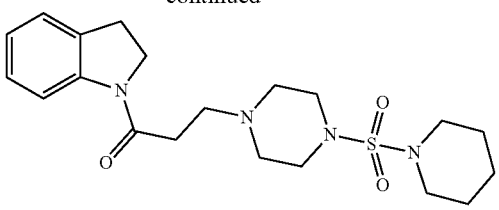

UNAOX031

UANOX031 was synthesized as per the procedure described for UANOX001. $^1$H NMR (400 MHz, CDCl$_3$) δ 8.23 (d, J=8 Hz, 1H), 7.24-7.20 (m, 2H), 7.04 (t, J=8 Hz, 1H), 4.10 (t, J=8 Hz, 2H), 3.30 (t, J=5 Hz, 4H), 3.26-3.22 (m, 6H), 2.91 (t, J=8 Hz, 2H), 2.67 (t, J=8 Hz, 2H), 2.61 (t, J=5 Hz, 4H), 1.67-1.56 (m, 6H). HPLC-MS: Expected: 407 (MH$^+$); Found: 407.

UANOX022 (1-(indolin-1-yl)-3-(4-(pyrimidin-2-yl)piperazin-1-yl)propan-1-one)

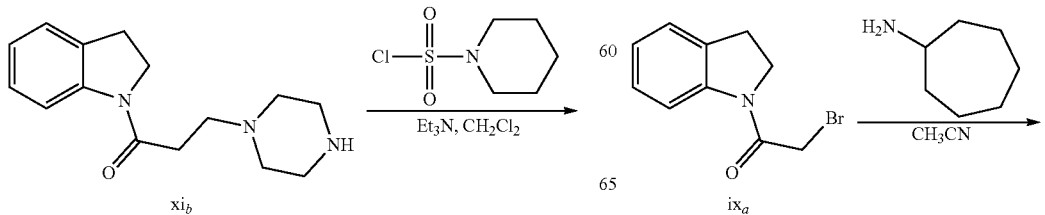

UANOX022

UANOX022 was synthesized as per the procedure described for compound 50. $^1$H NMR (400 MHz, CDCl$_3$) δ 8.32 (d, J=4 Hz, 2H), 8.24 (d, J=8 Hz, 1H), 7.25-7.21 (m, 2H), 7.03 (t, J=8 Hz, 1H), 6.49 (t, J=4 Hz, 1H), 4.10 (t, J=8 Hz, 2H), 3.87 (t, J=8 Hz, 4H), 3.22 (t, J=8 Hz, 2H), 2.90 (t, J=8 Hz, 2H), 2.70 (t, J=8 Hz, 2H), 2.60 (t, J=8 Hz, 4H). HPLC-MS: Expected: 338 (MH$^+$) and 339 (M+2); Found: 338 and 339.

UANOX023 (2-(cycloheptylamino)-1-(indolin-1-yl)ethan-1-one)

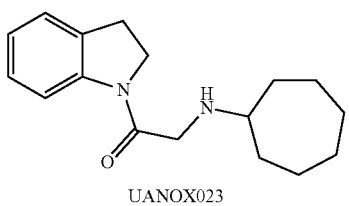

UANOX023

A solution of cycloheptanamine (1.87 mmol, 0.22 g, 0.24 mL) in 4 mL of $CH_3CN$ was added to a round bottomed flask equipped with a nitrogen inlet and a magnetic stir bar. To the above solution, 2-bromo-1-(indolin-1-yl)ethan-1-one (0.15 g, 0.624 mmol) in 2 mL $CH_3CN$ was added dropwise. The mixture was stirred at room temperature for overnight and then concentrated to give crude product. The product was purified using column chromatography with 2-5% MeOH in $CH_2C_2$ solvent to yield 110 mg (65%) of the desired product. The compound was re-purified using the same method above to give 68 mg (40%) of the pure compound as indicated by HPLC. $^1$H NMR (400 MHz, $CDCl_3$) δ 8.24 (d, J=8 Hz, 1H), 7.23-7.19 (m, 2H), 7.02 (t, J=8 Hz, 1H), 4.04 (t, J=8 Hz, 2H), 3.52 (s, 2H), 3.24 (t, J=8 Hz, 2H), 2.70 (septet, 4 Hz, 1H), 1.94-1.86 (m, 2H), 1.74-1.67 (m, 2H), 1.62-1.53 (m, 4H), 1.51-1.43 (m, 4H). HPLC-MS: Expected: 274 (M+2); Found: 274.

UANOX024 (3-(cycloheptylamino)-1-(indolin-1-yl)propan-1-one)

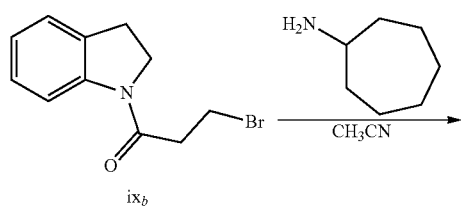

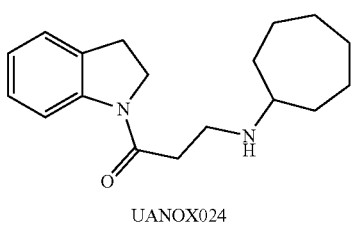

UANOX024

UANOX024 was synthesized as per the procedure described for compound UANOX023. $^1$H NMR (400 MHz, $CDCl_3$) δ 8.10 (d, J=8 Hz, 1H), 7.23-7.19 (m, 2H), 7.08 (t, J=8 Hz, 1H), 4.08 (t, J=8 Hz, 2H), 3.41 (t, J=8 Hz, 2H), 3.36-3.31 (m, 1H), 3.30 (quartet, J=4 Hz, 2H), 3.20 (t, 8 Hz, 2H), 2.32-2.25 (m, 2H), 1.97-1.90 (m, 2H), 1.89-1.81 (m, 2H), 1.64-1.61 (m, 4H), 1.59-1.48 (m, 2H). HPLC-MS: Expected: 228 (M+2); Found: 228 and 339.

Scheme 6

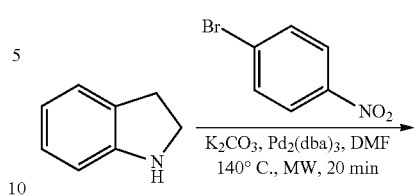

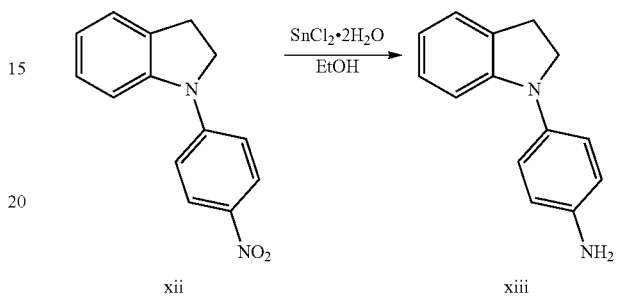

Synthesis of 1-(4-nitrophenyl)indoline (xii): A microwave vial was charged with the 4-bromonitrobenzene (2.16 g, 10.69 mmol), indoline (1.28 g, 10.70 mmol), and $Pd_2(dba)_3$ (0.059 mmol, 53 mg), $K_2CO_3$ (42.69 mmol, 5.9 g) and DMF (5 mL). The mixture was heated at 140° C. for 30 min at medium power in a biotage initiator. The reaction mixture was poured into to water and the aqueous was extracted with $CH_2Cl_2$ (×3). The combined organic layers were dried over $Na_2SO_4$, filtered, rotary evaporated and then dried in vacuo. The crude was loaded onto a flash silica gel column which was eluted with hexane-EtOAc (4:1) to give 2.27 g (88%) of the purified product as orange red solid. $^1$H NMR (400 MHz, $CDCl_3$) δ 8.24 (d, J=8 Hz, 2H), 7.37 (d, J=8 Hz, 1H), 7.30-7.28 (m, 2H), 7.24 (d, J=8 Hz, 2H), 6.96 (t, J=7.4 Hz, 1H), 4.10 (t, J=8 Hz, 2H), 3.24 (t, J=8 Hz, 2H).

Synthesis of 4-(indolin-1-yl)aniline (xiii): The solution of 1-(4-nitrophenyl)indoline (1.43 g, 9.44 mmol) in 15 mL EtOH was added to a round bottomed flask equipped with a nitrogen inlet and a magnetic stir bar. To the above solution, $SnCl_2.2H_2O$ (3.35 g, 14.85 mmol) was added and then the mixture was stirred at 70° C. overnight. To the mixture was added 4 N NaOH and the aqueous was extracted with EtOAc (×3). The combined organic layers were dried over anhydrous $Na_2SO_4$, concentrated and then dried in vacuo yielding brownish orange oil as crude. The crude was column chromatographed with 20% EtOAc in Hexanes yielding 630 mg (50%) of the pure and desired compound as purple solid. $^1$H NMR (400 MHz, $CDCl_3$) δ 7.16 (d, J=8 Hz, 1H), 7.12 (d, J=8 Hz, 2H), 7.05 (t, J=8 Hz, 1H), 6.82 (d, J=8 Hz, 1H), 6.76-6.69 (m, 3H), 3.99-3.77 (m, 2H), 3.13 (t, J=8 Hz, 2H). HPLC-MS: Expected: 210 (M)$^+$; Found: 210.

UANOX038 (N—(N,N-diethylaminosulfonyl)-4-(indolin-1-yl)aniline)

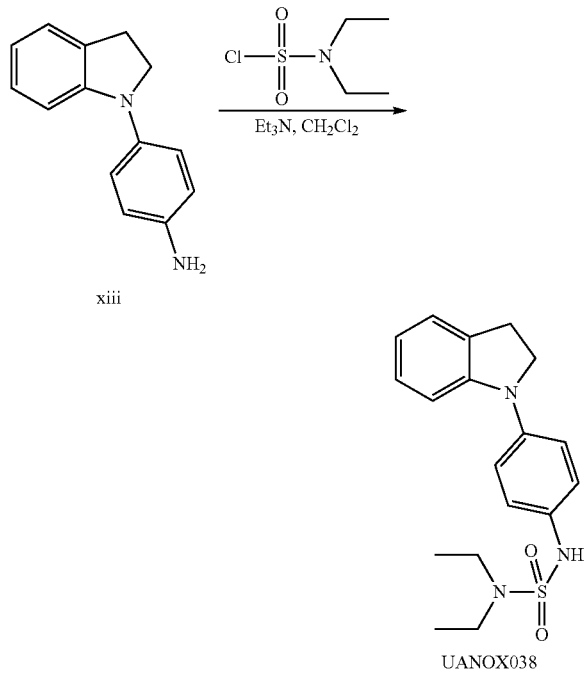

UANOX038 was synthesized as per the procedure described for UANOX001. $^1$H NMR (400 MHz, CDCl$_3$) δ 7.20-7.18 (m, 5H), 7.10-7.09 (m, 2H), 6.80-6.76 (m, 1H), 3.95 (t, J=8 Hz, 2H), 3.30 (t, J=7 Hz, 2H), 3.16 (t, J=8 Hz, 2H), 1.13 (t, J=7 Hz, 2H). HPLC-MS: Expected: 345 (MH$^+$); Found: 345.

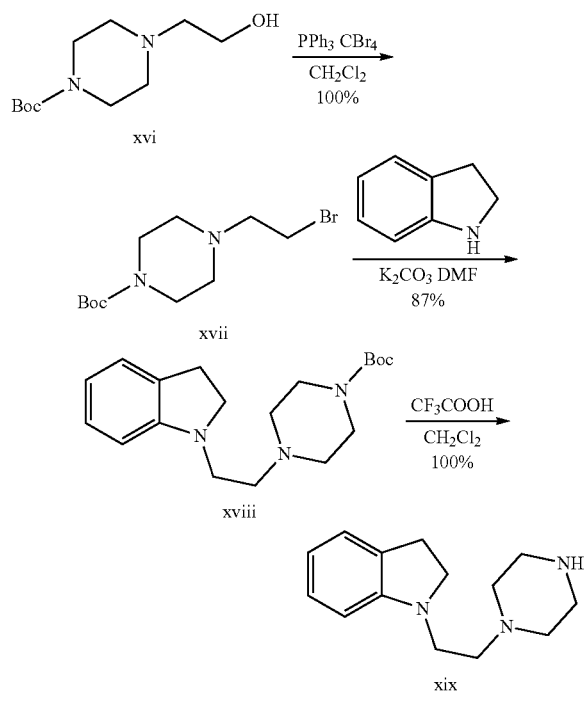

Synthesis of tert-butyl 4-(2-bromoethyl)piperazine-1-carboxylate (xvii)

In a round bottom flask equipped with N$_2$ inlet, a magnetic stir bar and an addition funnel, N-Boc-4-(2-hydroxyethyl)piperazine (xvi) (1 g, 4.34 mmol), PPh$_3$ (1.23 g, 4.7 mmol) CH$_2$Cl$_2$ (10 mL) was added. To the above mixture, a solution of carbon tetrabromide (1.58 g., 4.7 mmol) in 10 mL of CH$_2$Cl$_2$ was added dropwise over 2 h at 0° C. The mixture was stirred at room temperature for 20 h. The organic phase was evaporated to obtain an oil that was purified by flash chromatography (ethyl acetate/hexanes 2/8) to afford the desired product as an oily compound that slowly crystallized on storage (1.32, yield 100%). $^1$H NMR (400 MHz, Chloroform-d) δ 3.51-3.30 (m, 6H), 2.82-2.67 (m, 2H), 2.50-2.23 (m, 4H), 1.43 (s, 9H). Synthesized according to the procedure reported in *J. Med. Chem*, 2004, 47, 3, 711-719 and PCT Int. Appl., 2013064919, 10 May 2013.

Synthesis of tert-butyl 4-(2-(indolin-1-yl)ethyl)piperazine-1-carboxylate (viii)

Into a round bottomed flask equipped with a nitrogen inlet and a reflux condense, the solution of Indoline (0.55 g, 4.62 mmol, 0.52 mL) in 5 mL DMF was added. To the above solution, K$_2$CO$_3$ (1.25 g, 9.04 mmol) was added and then the mixture was stirred for 30 min. To the above mixture, tert-butyl 4-(2-bromoethyl)piperazine-1-carboxylate (1.35 g, 4.60 mmol, 1 eq) were then added to the mixture. The mixture was then heated at 110° C. or 2 hr. The mixture was then diluted with DI water, extracted with CH$_2$Cl$_2$(×3). The combined organic layers were dried over Na$_2$SO$_4$ anhydrous, concentrated and then dried in vacuo yielding 17 g of crude. The oily crude was column chromatographed with 50-70% EtOAc in Hexanes to give 1.3 g (87%) of the pure and desired compound. $^1$H NMR (400 MHz, Chloroform-d) δ 7.14-6.96 (m, 2H), 6.64 (d, J=8.2 Hz, 1H), 6.46 (d, J=7.6 Hz, 1H), 3.43 (t, J=4.9 Hz, 4H), 3.38 (t, J=8.3 Hz, 2H), 3.22 (t, J=8.3 Hz, 2H), 2.94 (t, J=6.6 Hz, 2H), 2.60 (t, J=7.0 Hz, 2l), 2.46 (t, J=5.0 Hz, 4H), 1.44 (s, 9H). HPLC-MS: Expected: 333 (M+2)$^+$; Found: 333.

Synthesis of 1-(2-(piperazin-1-yl)ethyl)indoline (xix)

Into a round bottomed flask equipped with a nitrogen inlet and a magnetic stir bar, the solution of tert-butyl 4-(2-(indolin-1-yl)ethyl)piperazine-1-carboxylate (1.3 g, 3.92 mmol) in 60 mL CH$_2$Cl$_2$ was added. To the above solution 17 mL of CF$_3$COOH was added and the mixture was stirred at room temperature for overnight. The reaction was monitored with TLC. The mixture was rotary evaporated, dissolved in water and then basified to pH 11 with sat aqueous Na$_2$CO$_3$ soln, poured into a separatory funnel and the layers were separated. The aqueous layer was then extracted with CH$_2$Cl$_2$ (×3). The combined organic layers were concentrated using rotary evaporator and then dried in vacuo yielding 930 mg (100%) of the desired product. $^1$H NMR (400 MHz, Chloroform-d) δ 7.06-7.02 (m, 2H), 6.62 (t, J=7.4 Hz, 1H), 6.47 (d, J=8.0 Hz, 1H), 3.38 (t, J=8.3 Hz, 2H), 3.22 (t, J=7.8 Hz, 2H), 3.00-2.83 (m, 6H), 2.58 (t, J=7.1 Hz, 2H), 2.55-2.43 (m, 4H). HPLC-MS: Expected: 232 (MH)$^+$; Found: 232.

UANOX062 (1-(2-(4-((4-(trifluoromethoxy)phenyl)sulfonyl)piperazin-1-yl)ethyl)indoline)

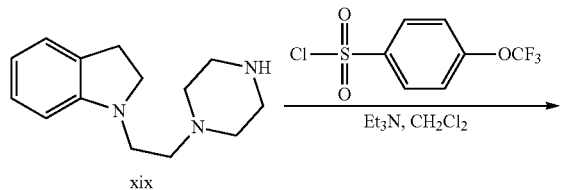

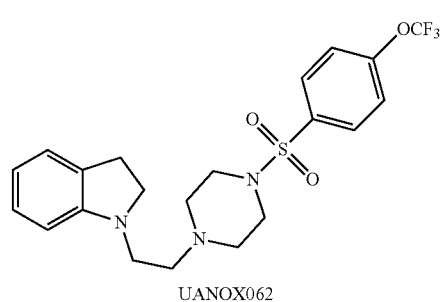

Into a 25-mL round bottomed flask equipped with a nitrogen inlet and a magnetic stir bar, 154 mg (0.67 mmol) of 1-(2-(piperazin-1-yl)ethyl)indoline. 210 mg (0.81 mmol) of 4-(trifluoromethoxy)benzenesulfonyl chloride, 0.19 mL (1.36 mmol) of triethylamine and 5 mL of $CH_2Cl_2$ were added. The mixture was stirred vigorously at room temperature for 18 h. To the mixture, DI water was added and then the mixture was transferred into a separatory funnel and the layers were separated. The aqueous layer was then extracted with $CH_2Cl_2$ (×3). The combined organic extracts were dried over anhydrous $Na_2SO_4$, the drying agent was removed by filtration and the filtrate was concentrated by rotary evaporation. The residue was further dried in vacuo to give light yellow oil as crude. The crude was then purified by prep TLC with 60% ethyl acetate in hexanes to give 185 mg (61%) of the pure and desired product as white solid. $^1$H NMR (400 MHz, Chloroform-d) δ 7.84 (d, J=9.0 Hz, 2H), 7.41-7.37 (m, 2H), 7.12-7.00 (m, 2H), 6.66 (td, J=7.5, 1.0 Hz, 1H), 6.45 (d, J=7.8 Hz, 1H), 3.36 (t, J=8 Hz, 2H), 3.19 (t, J=8 Hz, 2H), 3.10 (t, J=8 Hz, 4H), 2.97 (t, J=8H, 2H), 2.71-2.60 (m, 6H). HPLC-MS: Expected: 456 (MH)$^+$; Found: 456 and 454

UANOX063 (Synthesis of N,N-diethyl-4-(2-(indolin-1-yl)ethyl)piperazine-1-sulfonamide)

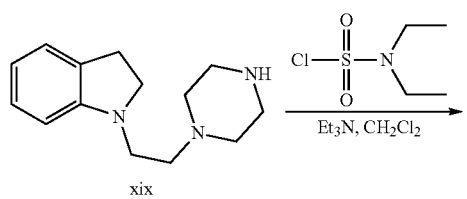

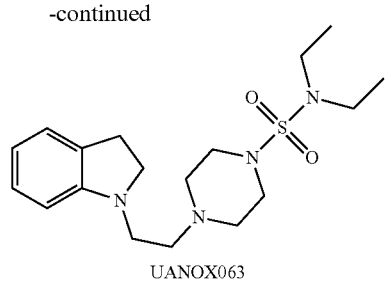

UANOX063 was synthesized as per the procedure described for UANOX062. $^1$H NMR (400 MHz, Chloroform-d) δ 7.10-7.06 (m, 2H), 6.67 (td, J=7.5, 1.0 Hz, 1H), 6.50 (d, J=7.6 Hz, 1H), 3.42 (t, J=8.4 Hz, 2H), 3.30 (q, J=7.0 Hz, 4H), 3.27-3.22 (m, 6H), 2.99 (t, J=8.3 Hz, 2H), 2.66 (t, J=8.3 Hz, 2H), 2.63-2.59 (m, 4H), 1.21 (t, J=7.1 Hz, 6H). HPLC-MS: Expected: 367 (MH)$^+$; Found: 367.

UANOX064 (1-(2-(4-((4-fluorophenyl)sulfonyl)piperazin-1-yl)ethyl)indoline)

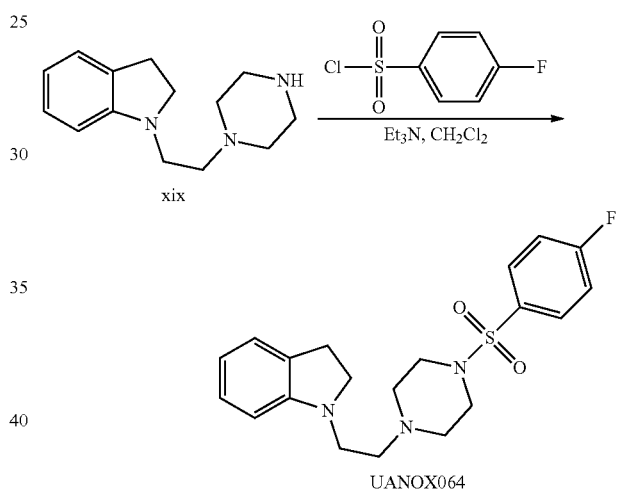

UANOX064 was synthesized as per the procedure described for UANOX062. $^1$H NMR (400 MHz, Chloroform-d) δ 7.80 (dd, J=9.0, 5.1 Hz, 2H), 7.24 (dd, J=9.0, 8.3 Hz, 2H), 7.10-7.02 (m, 2H), 6.66 (td, J=7.4, 1.0 Hz, 1H), 6.45 (d, J=7.8 Hz, 1H), 3.36 (t, J=8.4 Hz, 2H), 3.19 (t, J=8.4 Hz, 2H), 3.12-3.06 (m, 4H), 2.96 (t, J=8.3 Hz, 2H), 2.70-2.60 (m, 6H). HPLC-MS: Expected: 390 (MH)$^+$; Found: 390.

UANOX066 (Synthesis of 1-(2-(4-(benzo[d][1,3]dioxol-5-ylsulfonyl)piperazin-1-yl)ethyl)indoline)

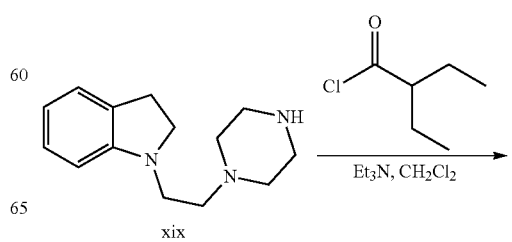

-continued

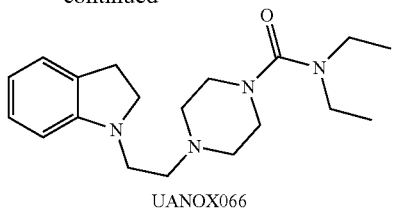

UANOX066

UANOX066 was synthesized as per the procedure described for UANOX062. $^1$H NMR (400 MHz, Chloroform-d) δ 7.11-7.04 (m, 2H), 6.67 (td, J=7.3, 1.0 Hz, 1H), 6.51 (d, J=7.4 Hz, 1H), 3.42 (t, J=8.4 Hz, 2H), 3.31-3.26 (m, 6H), 3.23 (q, J=7.1 Hz, 4H), 2.99 (t, J=8.4 Hz, 2H), 2.66 (t, J=8.4 Hz, 2H), 2.60-2.53 (m, 4H), 1.15 (t, J=7.1 Hz, 6H). HPLC-MS: Expected: 331(MH)$^+$; Found: 331

UANOX067 (Synthesis of 1-(2-(4-(2-fluorobenzyl)piperazin-1-yl)ethyl)indoline)

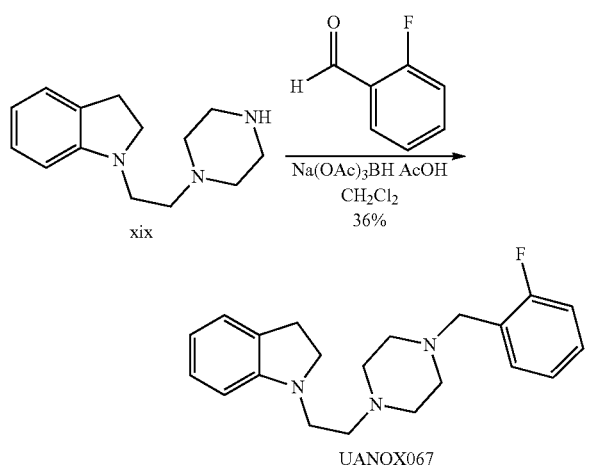

UANOX067

In a round bottomed flask equipped with a nitrogen inlet and a magnetic stir bar, 2-fluorobenzaldehyde (83 mg, 0.67 mmol), 1-(2-(piperazin-1-yl)ethyl)indoline (154 mg, 0.67 mmol) and CH$_2$Cl$_2$(5 mL) were added. To the above mixture AcOH (38 μL, 0.67 mmol) was added. The reaction was stirred for 1 hour at room temperature. To the mixture Na(OAc)$_3$BH (426 mg, 2.01 mmol) was added in portion over a period of 2 hours. The reaction mixture was allowed to stir overnight at room temperature. The reaction mixture was poured into H$_2$O and the aqueous was extracted with CH$_2$Cl$_2$ (×3). The organic layer was dried over Na$_2$SO$_4$, filtered and then rotary evaporated. The crude was purified by preparatory TLC with 10% MeOH in CH$_2$Cl$_2$ to give 208 mg of the desired product. The product was repurified using same condition as above to give 81 mg (36%) of the pure and desired compound as amber color oil. $^1$H NMR (400 MHz, Chloroform-d) δ 7.39 (td, J=7.5, 1.8 Hz, 1H), 7.31-7.23 (m, 1H), 7.13 (td, J=7.5, 1.2 Hz, 1H), 7.10-7.02 (m, 3H), 6.67 (td, J=7.4, 1.0 Hz, 1H), 6.50 (d, J=9.1 Hz, 1H), 3.69 (d, J=1.3 Hz, 2H), 3.40 (t, J=8.3 Hz, 2H), 3.29 (t, J=8.3 Hz, 2H), 2.98 (t, J=8.3 Hz, 2H), 2.73 (t, J=8.3 Hz, 4H), 2.67-2.58 (m, 4H), 2.10-2.06 (m, 2H). HPLC-MS: Expected: 340 (MH)$^+$; Found: 340.

Nox4 Mediates Fibrotic Responses to Lung Injury

The NADPH-oxidase (Nox) enzymes are an evolutionarily conserved gene family that that is most consistently linked to host defense mechanisms, including lung fibrosis (Bernard K et al., *Antioxidants & redox signaling* 20: 2838-2853, 2014; Thannickal V J, Zhou Y, Gaggar A, and Duncan S R. Fibrosis: ultimate and proximate causes. *The Journal of clinical investigation* 124: 4673-4677, 2014). The role of Nox4 in injury-induced fibrosis was evaluated using a murine model of lung injury. In this animal model, intra-tracheal instillation of the chemotherapeutic agent, bleomycin, induces epithelium injury that leads to peak fibrosis 2-3 weeks post-injury (Hecker L et al., NADPH oxidase-4 mediates myofibroblast activation and fibrogenic responses to lung injury. *Nature medicine* 15: 1077-1081, 2009; Izbicki G et al., Time course of bleomycin-induced lung fibrosis. *International journal of experimental pathology* 83: 111-119, 2002). Nox4 is induced in a time-dependent manner, increasing from day 7 up to day 28, supporting a temporal relationship between Nox4 expression, myofibroblast activation, and fibrosis following lung injury (*Nature medicine* 15: 1077-1081, 2009). In contrast, the Nox2 isoform (predominantly expressed in phagocytic cells) increases on day 7 (peak inflammatory phase) and returns to baseline levels at later time-points when inflammatory responses subside (*Nature medicine* 15: 1077-1081, 2009).

Nox4 is Unregulated in the Lungs of Human IPF Patients

Among the seven members of the Nox family, Nox4 has now been implicated in a variety of fibrotic diseases, including the liver (Aoyama T et al., *Hepatology* 56: 2316-2327, 2012; Bettaieb A et al., *Gastroenterology* 149: 468-480 e410, 2015; Sancho P et al., *PloS one* 7: e45285, 2012), skin (Spadoni T et al., *Arthritis & rheumatology* 67: 1611-1622, 2015), kidney (Bames J L et al., *Kidney international* 79: 944-956, 2011; Sedeek M et al., *American journal of physiology Renal physiology* 299: F1348-1358, 2010), heart (Ago T et al., *Aging* 2: 1012-1016, 2010; Kuroda J et al., *Proceedings of the National Academy of Sciences of the United States of America* 107: 15565-15570, 2010), and lung (Griffith B et al., *Antioxidants & redox signaling* 11: 2505-2516, 2009; Harrison C et al., *Nat Rev Drug Discov* 8: 773-773, 2009; Hecker L et al., *Science translational medicine* 6: 231ra247, 2014; *Nature medicine* 15: 1077-1081, 2009). It has been demonstrated that Nox4 is upregulated in lung myofibroblasts of human IPF patients (Amara N et al., *Thorax* 65: 733-738, 2010; *Science translational medicine* 6: 231ra247, 2014).

Therapeutic targeting of Nox4 inhibits the development of fibrosis and results in a reversal of established/persistent fibrosis in mice.

While it has been shown that genetic targeting of Nox4 ameliorates the development of injury-induced lung fibrosis in young mice (*Nature medicine* 15: 1077-1081, 2009). It has also been demonstrated that genetic knockdown of Nox4 (via intra-tracheal delivery of Nox4-siRNA to the lungs of injured mice) in an animal model of persistent lung fibrosis led to a reversal of established fibrosis (*Science translational medicine* 6: 231ra247, 2014). It was later validated by similar findings using mice with genetic deletion of Nox4 (Camesecchi S et al., *Antioxid Redox Signal* 15: 607-619, 2011). Overall, these studies demonstrate a critical role for Nox4 in mediating lung fibrosis. Since the initial discovery that Nox4 mediates lung tissue fibrosis (*Nature Medicine*, 2009), Nox4 has been implicated in fibrotic disease of various organ systems (liver, skin, kidney, and cardiac). Nox4 is now considered to be among the most promising therapeutic targets for fibrotic disease (*Nat Rev Drug Discov*

8: 773-773, 2009; Liepelt A et al., *Annals of translational medicine* 3: S13, 2015). However, no selective Nox4 inhibitors are clinically available.

Efficacy of Analogs for Inhibition of Nox4-Dependent $H_2O_2$

A high-throughput screening (HTS) assay was established for Nox4 inhibition, utilizing HEK293 cells that stably over-express Nox4 (HEK/Nox4 cells), which generate high levels of $H_2O_2$ (Cheng G et al, *Gene:* 2001, p. 131-140). Over 30,000 compounds have been screened and medicinal chemistry efforts have led to the synthesis of numerous analogs and the identification of a chemically distinct series of selective Nox4 inhibitors. Table 1 shows dose-dependent activity of various analogs synthesized. FIG. 1A shows a subset of these analogs versus vehicle and DPI (a positive control, as DPI inhibits all Nox activity). Treatment with UANox048 or UANox034 led to a dose-dependent decrease in $H_2O_2$ generation by HEK/Nox4 cells, as measured by Amplex Red assay (FIG. 1A). IC-50 was evaluated for UANox048 (FIG. 1B).

TABLE 1

Efficacy for inhibition of Nox4-dependent $H_2O_2$.
HEK cells stably transfected to overexpress Nox4 were treated with test compounds and synthesized analogs in DMSO and incubated for 1 h. $H_2O_2$ production was evaluated by Amplex Red assay. Values represent means and SD of $H_2O_2$ production after treatment with 1, 5, and 10 μM (final concentration) test compounds and synthesized analogs. $H_2O_2$ production reported relative to vehicle control; n = 3-10/group.

| | Final concentration (μM) | | | | | |
|---|---|---|---|---|---|---|
| | 1 | | 5 | | 10 | |
| Compound Name | Mean | SD | Mean | SD | Mean | SD |
| DMSO (Vehicle control) | 1.000 | 0.050 | | | | |
| UANOX001 | 0.995 | 0.060 | 1.063 | 0.030 | 1.032 | 0.011 |
| UANOX002 | 0.986 | 0.067 | 1.061 | 0.035 | 1.015 | 0.037 |
| UANOX003 | 1.008 | 0.134 | 1.029 | 0.015 | 1.028 | 0.018 |
| UANOX004 | 0.994 | 0.029 | 1.007 | 0.070 | 0.882 | 0.167 |
| UANOX006 | 0.822 | 0.105 | 0.825 | 0.108 | 0.741 | 0.107 |
| UANOX007 | 1.026 | 0.028 | 0.916 | 0.037 | 0.908 | 0.016 |
| UANOX008 | 0.984 | 0.065 | 0.779 | 0.113 | 0.678 | 0.091 |
| UANOX011 | 0.980 | 0.080 | 0.979 | 0.019 | 0.956 | 0.008 |
| UANOX012 | 0.960 | 0.003 | 0.950 | 0.040 | 0.857 | 0.073 |
| UANOX013 | 1.006 | 0.041 | 0.921 | 0.060 | 0.881 | 0.020 |
| UANOX018 | 1.101 | 0.056 | 1.027 | 0.037 | 1.002 | 0.068 |
| UANOX019 | 0.915 | 0.153 | 0.814 | 0.185 | 0.741 | 0.135 |
| UANOX020 | 0.737 | 0.089 | 0.870 | 0.110 | 0.866 | 0.111 |
| UANOX021 | 0.742 | 0.054 | 0.876 | 0.021 | 0.791 | 0.040 |
| UANOX022 | 1.106 | 0.075 | 1.069 | 0.055 | 1.103 | 0.030 |
| UANOX023 | 0.984 | 0.062 | 1.077 | 0.062 | 1.003 | 0.043 |
| UANOX025 | 1.071 | 0.015 | 1.131 | 0.020 | 1.124 | 0.065 |
| UANOX026 | 0.906 | 0.232 | 1.059 | 0.074 | 1.011 | 0.143 |
| UANOX027 | 1.128 | 0.017 | 1.131 | 0.012 | 1.124 | 0.027 |
| UANOX028 | 1.081 | 0.051 | 1.123 | 0.007 | 1.111 | 0.038 |
| UANOX029 | 1.125 | 0.035 | 1.117 | 0.021 | 1.096 | 0.058 |
| UANOX030 | 1.080 | 0.034 | 1.084 | 0.027 | 1.037 | 0.012 |
| UANOX031 | 1.111 | 0.019 | 1.106 | 0.040 | 0.997 | 0.045 |
| UANOX032 | 1.118 | 0.036 | 1.091 | 0.066 | 1.052 | 0.048 |
| UANOX033 | 1.004 | 0.052 | 0.912 | 0.148 | 0.867 | 0.034 |
| UANOX034 | 0.959 | 0.032 | 0.803 | 0.039 | 0.706 | 0.017 |
| UANOX036 | 1.018 | 0.037 | 0.832 | 0.027 | 0.747 | 0.016 |
| UANOX037 | 0.972 | 0.029 | 0.793 | 0.052 | 0.773 | 0.035 |
| UANOX038 | 0.925 | 0.150 | 0.800 | 0.125 | 0.635 | 0.226 |
| UANOX048 | 0.893 | 0.020 | 0.765 | 0.031 | 0.693 | 0.023 |
| UANOX049 | 0.871 | 0.028 | 0.784 | 0.016 | 0.714 | 0.019 |
| UANOX054 | 0.902 | 0.038 | 0.876 | 0.013 | 0.824 | 0.017 |
| UANOX055 | 0.902 | 0.019 | 0.908 | 0.006 | 0.868 | 0.028 |
| UANOX056 | 0.959 | 0.025 | 0.884 | 0.033 | 0.834 | 0.023 |
| UANOX062 | 0.887 | 0.066 | 0.758 | 0.040 | 0.664 | 0.052 |
| UANOX063 | 0.902 | 0.063 | 0.719 | 0.031 | 0.665 | 0.022 |
| UANOX064 | 0.863 | 0.040 | 0.757 | 0.022 | 0.724 | 0.033 |
| UANOX066 | 0.953 | 0.020 | 0.722 | 0.037 | 0.731 | 0.021 |
| UANOX067 | 0.939 | 0.040 | 0.912 | 0.016 | 0.851 | 0.014 |

TABLE 1-continued

Efficacy for inhibition of Nox4-dependent $H_2O_2$.
HEK cells stably transfected to overexpress Nox4 were treated with test compounds and synthesized analogs in DMSO and incubated for 1 h. $H_2O_2$ production was evaluated by Amplex Red assay. Values represent means and SD of $H_2O_2$ production after treatment with 1, 5, and 10 μM (final concentration) test compounds and synthesized analogs. $H_2O_2$ production reported relative to vehicle control; n = 3-10/group.

| | Final concentration (μM) | | | | | |
|---|---|---|---|---|---|---|
| | 1 | | 5 | | 10 | |
| Compound Name | Mean | SD | Mean | SD | Mean | SD |
| UANOX070 | 0.914 | 0.025 | 0.779 | 0.024 | 0.693 | 0.003 |
| UANOX071 | 0.908 | 0.010 | 0.856 | 0.001 | 0.770 | 0.012 |
| UANOX073 | 0.942 | 0.094 | 0.759 | 0.029 | 0.744 | 0.057 |
| UANOX075 | 0.823 | 0.057 | 0.721 | 0.055 | 0.677 | 0.042 |
| UANOX076 | 0.832 | 0.025 | 0.720 | 0.031 | 0.662 | 0.026 |
| UANOX079 | 0.896 | 0.007 | 0.651 | 0.016 | 0.584 | 0.031 |
| UANOX080 | 0.855 | 0.039 | 0.601 | 0.044 | 0.491 | 0.028 |
| UANOX081 | 0.888 | 0.056 | 0.670 | 0.018 | 0.558 | 0.060 |
| UANOX082 | 0.908 | 0.058 | 0.707 | 0.032 | 0.606 | 0.038 |
| UANOX083 | 0.823 | 0.083 | 0.730 | 0.016 | 0.665 | 0.007 |
| UANOX084 | 0.903 | 0.038 | 0.775 | 0.057 | 0.675 | 0.023 |
| UANOX085 | 0.927 | 0.056 | 0.835 | 0.018 | 0.736 | 0.024 |
| UANOX086 | 0.907 | 0.046 | 0.816 | 0.013 | 0.714 | 0.006 |
| UANOX087 | 0.997 | 0.036 | 0.883 | 0.014 | 0.741 | 0.008 |
| UANOX088 | 1.023 | 0.047 | 0.903 | 0.012 | 0.796 | 0.019 |
| UANOX089 | 1.013 | 0.019 | 0.836 | 0.056 | 0.701 | 0.022 |
| UANOX090 | 1.045 | 0.017 | 0.887 | 0.042 | 0.745 | 0.009 |
| UANOX0254 | 0.878 | 0.126 | 0.880 | 0.025 | 0.763 | 0.081 |
| UANOX0192 | 0.964 | 0.033 | 1.108 | 0.044 | 1.080 | 0.023 |

HEK cells stably transfected to overexpress Nox4 were treated with varying concentrations of test compounds, DPI (all-Nox inhibitor positive control), or DMSO (vehicle control) and incubated for 1 h (FIG. 1). (FIG. 1A) $H_2O_2$ presence was evaluated by Amplex Red assay. (FIG. 1B) $IC_{50}$ was evaluated for UANox048 in HEK/Nox4 cells and was then determined to be 4.8 μM. Values represent means±SEM; n=4. P values were calculated by student's two-tailed t test. *p<0.05, p<0.01, * p<0.001.

Compound Pass of False-Positive Testing

Figure 2:
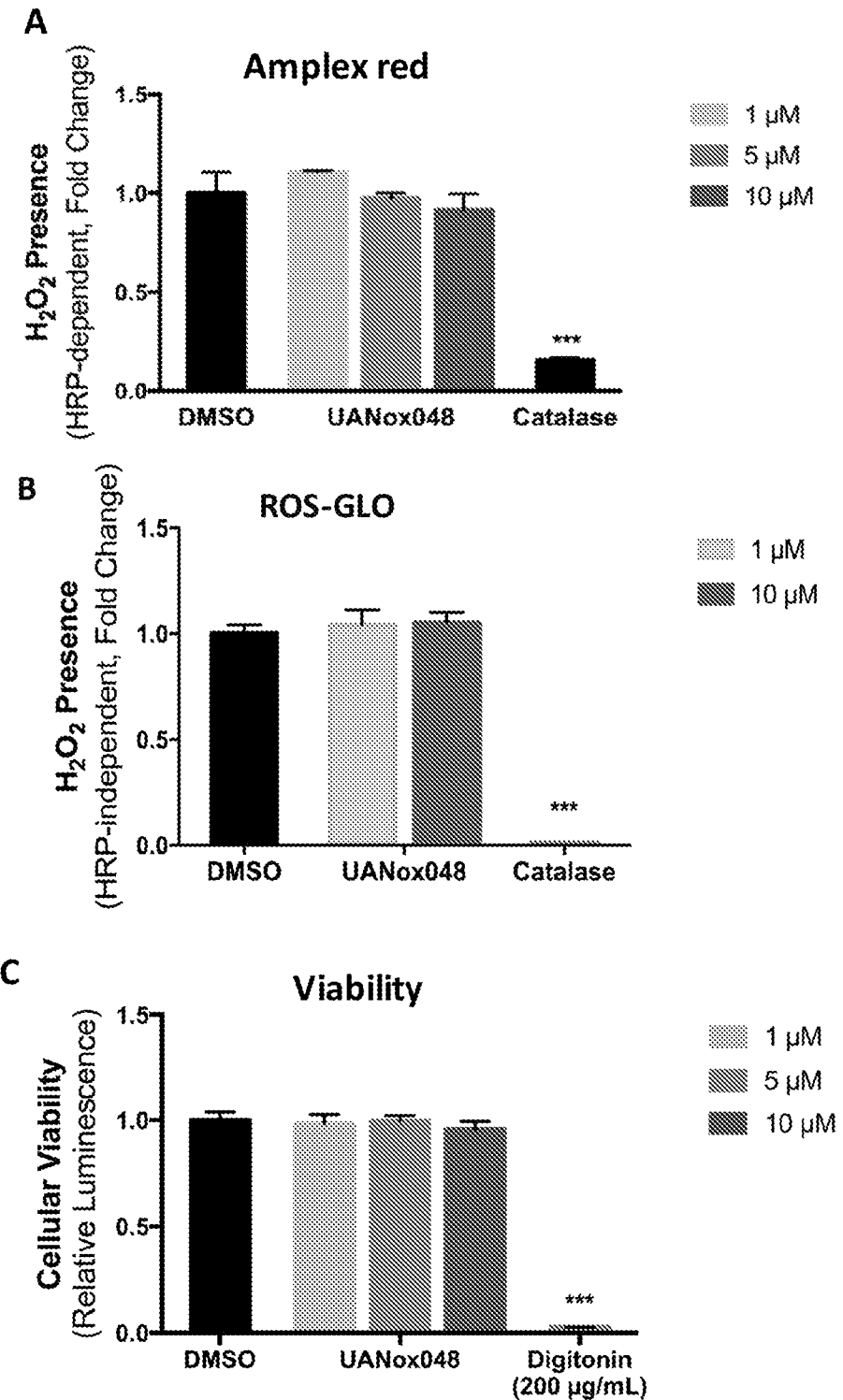
FIG. 2 is a graph showing UANox048 scavenger activity for $H_2O_2$ assessed by (A) Amplex Red assay, (B) ROS-Glo assay, and (C) cellular viability in HEK cells stably transfected to overexpress Nox4 treated with UANox048.

Screening was performed to rule out false positives. UANox048 does not demonstrate scavenger activity (FIG. 2A), does not exhibit assay interference (via inhibition of HRP activity) (FIG. 2B), and does not affect cellular viability (FIG. 2C).

UANoxO48, DMSO (vehicle control), or catalase (known $H_2O_2$ scavenger positive control) was added to a cell-free assay containing exogenous $H_2O_2$(5 mM) and scavenger activity for $H_2O_2$ was assessed by (FIG. 2A) Amplex Red assay and (FIG. 2B) ROS-Glo assay (an HRP-free assay system to rule out assay interference). (FIG. 2C) HEK cells stably transfected to overexpress Nox4 were treated with UANox048, digitonin (an inducer of cell death), or DMSO (vehicle control) and incubated for 1 h. Cellular viability was evaluated by CellTiter-Glo Assay. Values represent means±SEM; n=4; P values were calculated by student's two-tailed t test. *p<0.05, p<0.01, * p<0.001.

Compounds are Highly Selective for Nox4-Dependent $H_2O_2$

Figure 3:
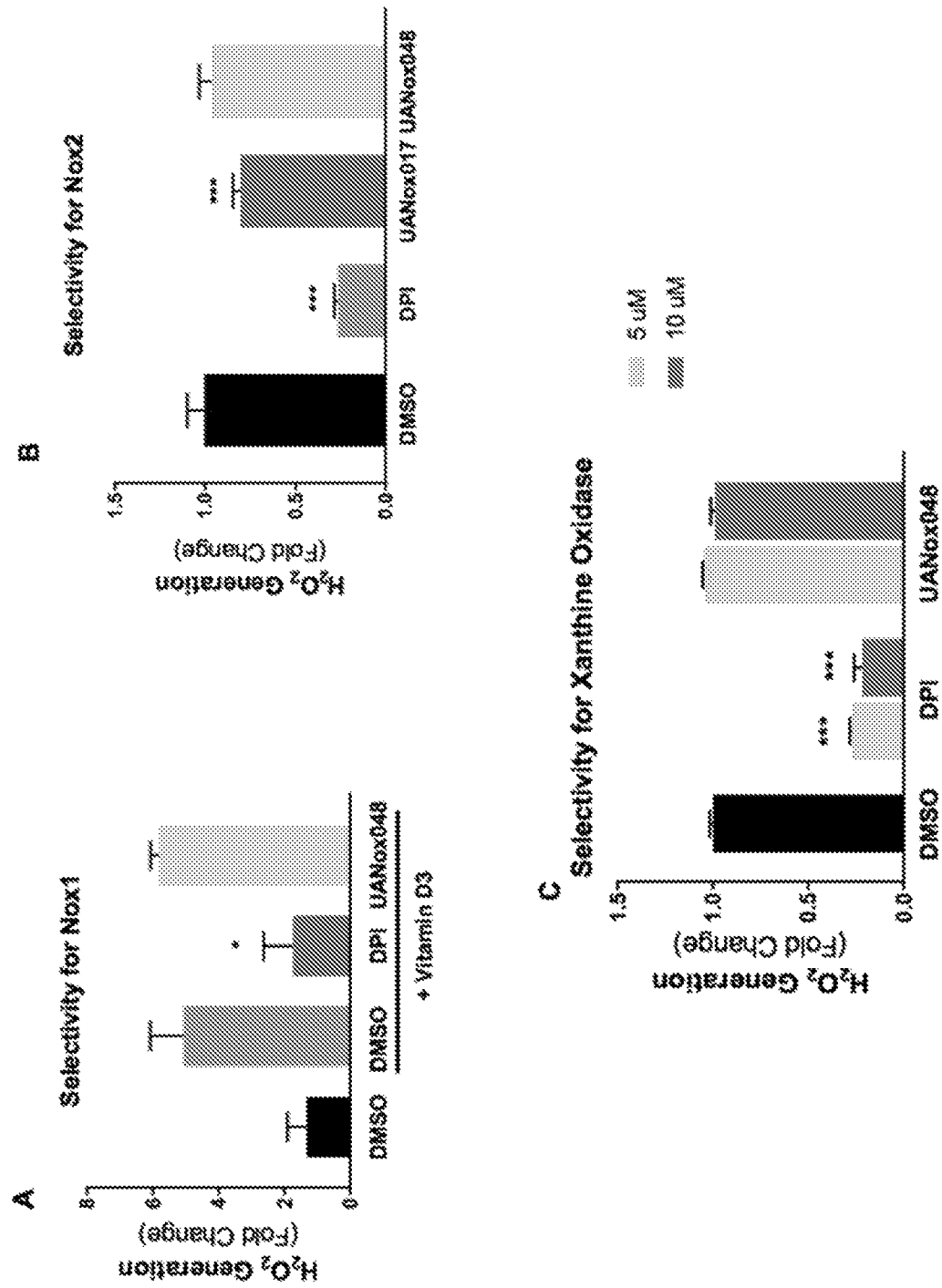
FIG. 3 is a graph showing UANox048 evaluated for (A) Nox1 selectivity by Amplex Red assay, (B) Nox2 selectivity by Amplex Red assay, and (C) Xanthine Oxidase selectivity by Amplex Red assay.

There are no clinically-available selective Nox4 inhibitors. Screening assays to evaluate selectivity against Nox1 and Nox2 were developed in an effort to identify highly selective inhibitors of Nox4, with low selectivity for closely-related Nox homologs. Importantly, analogs show little to no inhibition of Nox2- and Nox1-dependent $H_2O_2$(FIG. 3). Additionally, analogs do not inhibit Nox-independent mechanisms of $H_2O_2$ production, as measured by impact on xanthine oxidase (XO)-dependent $H_2O_2$ generation. These data support the identification of small-molecule inhibitors that are highly selective for Nox4.

Caco-2 cells were co-treated with Calcitriol (1 μM, 18 h, to induce Nox1-dependent $H_2O_2$ generation) and test compounds, DPI (all-Nox inhibitor positive control), or DMSO (vehicle control). $H_2O_2$ production was evaluated by Amplex Red assay (FIG. 3A). RAW 264.7 cells were co-treated with PMA (20 μM, 2 h, to induce Nox2-dependent $H_2O_2$ generation) and test compounds, DPI (all-Nox inhibitor), or DMSO (vehicle). Nox2-dependent $H_2O_2$ was evaluated by Amplex Red assay (FIG. 3B). XO-dependent $H_2O_2$ production was initiated in the presence of test compounds or vehicle control (DMSO). The reaction was incubated for 30 m and $H_2O_2$ presence was quantified by Amplex Red assay (FIG. 3C). Values represent means±SEM; n=3; P values were calculated by student's two-tailed t test. *p<0.05, p<0.01, * p<0.001.

Figure 4:
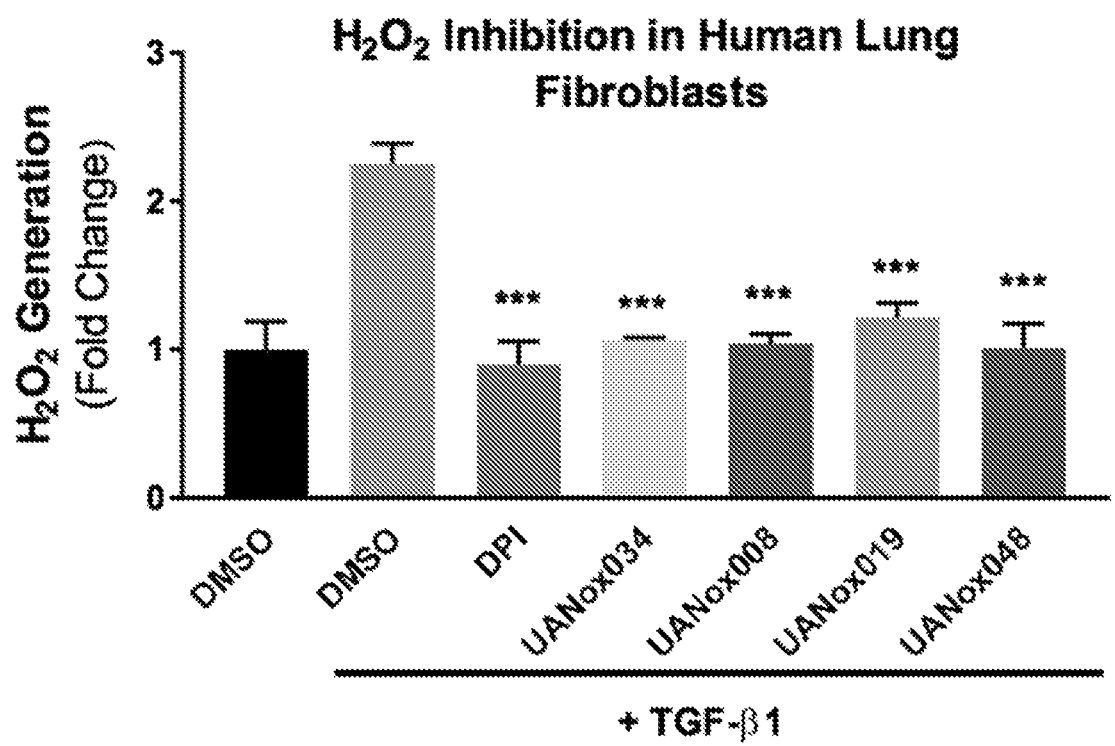
FIG. 4 is a graph showing $H_2O_2$ inhibition by Amplex Red assay of human lung fibroblasts (IMR90 cells) treated with UANox034, UANox008, UANox019 and UANox048.

Compounds Demonstrate Inhibition of Disease-Relevant Cellular Phenotypes in Human Lung Fibroblasts It has been demonstrated that TGF-β1 (a cytokine known to be highly expressed in fibrotic diseases) leads to the induction of Nox4-dependent $H_2O_2$, which mediates critical pro-fibrotic lung myofibroblast phenotypes, including differentiation, contraction, and ECM generation (*Nature medicine* 15: 1077-1081, 2009). Whole-genome Affymetrix analysis in human lung fibroblasts revealed that in response to TGF-β1, Nox4 was among the most highly induced genes in the human genome (*Nature medicine* 15: 1077-1081, 2009). The inducibility of Nox4-dependent $H_2O_2$ by TGF-β1 is a highly specific and unique function of Nox4 (Martyn K D et al., *Cellular signalling* 18: 69-82, 2006; Serrander L et al., *The Biochemical journal* 406: 105-114, 2007; von Lohneysen K et al., *The Journal of biological chemistry* 287: 8737-8745, 2012; von Lohneysen K et al., *The Journal of biological chemistry* 283: 35273-35282, 2008; von Lohneysen K et al., *Molecular and cellular biology* 30: 961-975, 2010); no other Nox family gene members are affected at the mRNA level (*Nature medicine* 15: 1077-1081, 2009). This unique feature of Nox4 has been exploited in screening efforts to validate lead drug candidates. Analogs demonstrated high efficacy for inhibition of TGF-β-induced Nox4-dependent $H_2O_2$ in human lung fibroblasts (FIG. 4).

Analogs Inhibit TGF-β1-Induced Nox4-Dependent $H_2O_2$ in Human Lung Fibroblasts Human lung fibroblasts (IMR90 cells) were serum starved for 16 h, then stimulated with/without TGF-β1 (2 ng/ml) for 12 h. Cells were then treated with test compounds, DPI (all-Nox inhibitor positive control), or DMSO (vehicle control) and incubated for an additional 4 h. $H_2O_2$ was evaluated by Amplex Red assay (FIG. 4). Values represent means±SEM: n=3; *P<0.05 using Student's two-tailed t. *p<0.05, p<0.01, *p<0.001.

Figure 5:
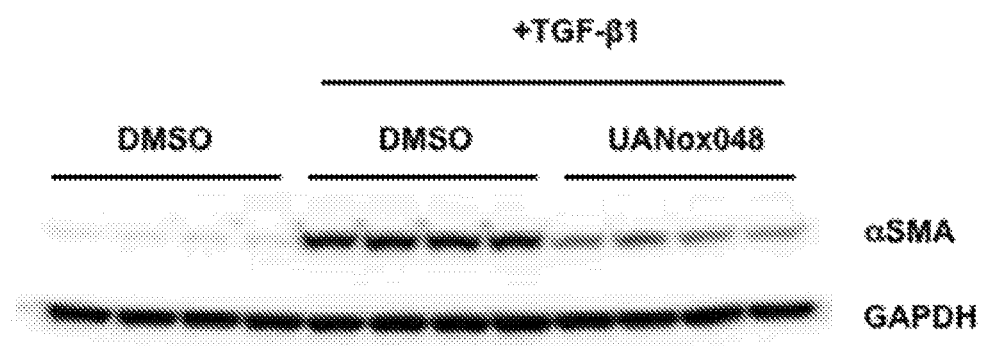
FIG. 5 is a graph showing Western-immunoblotting (A) and densitometric analyses (B) of αSMA in human lung fibroblasts (IMR90 cells) treated with UANox048.
Figure 5:
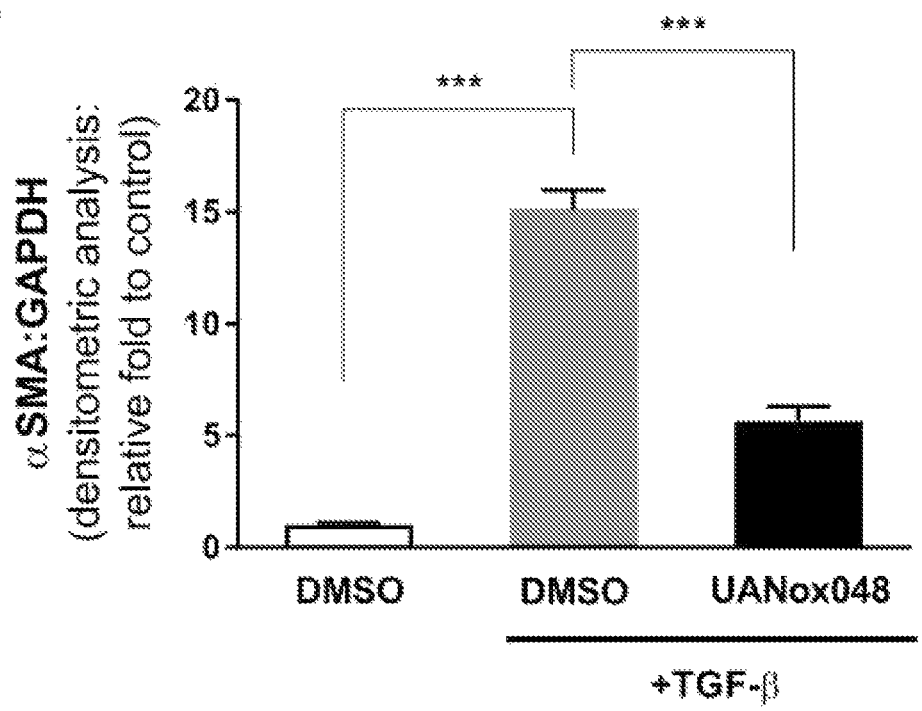

TGF-β1-induced Nox4-dependent $H_2O_2$ mediates fibroblast-to-myofibroblast differentiation, as characterized by the synthesis of α-smooth muscle actin (αSMA). These key effector cells play a central role in fibrotic "scar" generation, as they are contractile cells responsible for the synthesis of extracellular matrix (ECM) components. The accumulation of αSMA-expressing myofibroblast cells is a key pathological hallmark of fibrotic disease (Desmouliere A et al., *The American journal of pathology* 146: 56-66, 1995). The compounds were evaluated for their ability to inhibit fibroblast-to-myofibroblast differentiation. Analogs effectively inhibit TGF-β-induced Nox4-dependent myofibroblast differentiation in human lung fibroblasts (FIG. 5). Together, these data indicate that analogs demonstrate the ability to inhibit key pro-fibrotic cellular phenotypes in human lung fibroblasts.

Analogs Inhibit TGF-β1-Induced Fibroblast-to-Myofibroblast Differentiation

Human lung fibroblasts (IMR90 cells) were serum starved for 16 h, then stimulated with/without TGF-β1 (2 ng/ml) and co-treated with test compounds, DPI (all-Nox inhibitor positive control), or DMSO (vehicle control) and incubated for 48 h. αSMA presence was evaluated by Western-immunoblotting (FIG. 5A), and densitometric analyses (FIG. 5B). Values represent means * SEM; n=4; *P<0.05 using Student's two-tailed t-test. *p<0.05, p<0.01, * p<0.001.

Biophysical Characterization and Microscopy of Analogs

Studies were performed on the biophysical characterization of selected analogs, to demonstrate feasibility of an essential requirement aimed at guiding rational formulation design and ensuring reproducibility (i.e. quality control) of compound integrity during scale-up, manufacture, and storage. Differential scanning calorimetry (DSC) was used, a highly sensitive thermos-analytical technique to quantify the thermotropic properties and phase transitions of drug candidates. UANox048 was found to be highly stable, with a relatively high solid-to-liquid melting phase transition; $T_{onset}$ 89.72±0.22(° C.), $T_{peak}$ 92.3±0.05 (° C.), enthalpy 64.87±21.39 (J/g) measuring the energetics during the solid-to-liquid phase transition (FIG. 6A). This is important from a pharmaceutical standpoint, as these data indicate that UANOX048 is highly stable at both room and body temperatures (32-37° C.; drug manufacture/processing and delivery temperatures). X-ray powder diffraction (XRPD) is a non-destructive material science "gold standard" method for measuring the degree of long-range molecular order in the powder. This is critical for solid-state characterization, where drug candidates yield a unique pattern for any given crystalline phase; this provides a 'molecular fingerprint' for crystallinity identification. XRPD of UANox048 demonstrates a unique molecular signature, which is consistent between batches of UANOX048 synthesized at different times in different quantities (FIG. 6B). Attenuated Total Reflection Fourier Transform Infrared (ATR-FTIR) Spectroscopy is a non-destructive molecular identification tool based on the absorption of infrared light by vibrational transitions in covalent bonds. This provides a 'molecular fingerprint' for chemical identification. ATR-FTIR permits fine discrimination between like materials and/or batch-to-batch quality verification; it is used to identify active pharmaceutical ingredients (API). ATR-FTIR spectroscopy reveals a consistent molecular fingerprint of UANox048 from two different batches, synthesized at different times. Together, XRPD and ATR-FTIR results demonstrate proof-of-concept and feasibility of successful and consistent UANox048 scale-up. Scanning Electron Microscopy (SEM) with Energy Dispersive X-ray (EDX) is used to visualize the synthesized particles in their native solid-state and quantify important particle properties which directly influence formulation, including surface structure, particle morphology and size, and particle size range distribution. SEM of UANox048 indicates a surface structure that is typical of small molecular weight drugs with crystalline properties. Confocal Raman Microspectroscopy is a non-destructive analytical tool that is used to evaluate the spatial distribution of chemical components within a formulation; this permits characterization of formulation homogeneity and detection of foreign particulate contaminants. This critical molecular identification tool is routinely used to determine patent infringements. Confocal Raman microspectroscopy of UANox048 demonstrates a unique molecular fingerprint of its chemical identity.

Analogs Demonstrate Favorable In Vitro ADME Characteristics for Oral Formulation/Delivery In vitro absorption, distribution, metabolism, and excretion (ADME) were performed on selected analogs to assess their potential for continued pre-clinical development. UANox048 analog has favorable pharmacokinetic/pharmacodynamics properties, including a low molecular weight (384.4 g/mol), calculated log D value (4.07), and polar surface area (57.8 Å$^2$). The compounds were tested for cellular permeability and P-glycoprotein efflux susceptibility (P-gp efflux). UANox048 demonstrates effective Caco-2 permeability properties (high), and no P-gp efflux. P-gp efflux was calculated by comparing permeability through Caco-2 monolayers in both the apical-to-basolateral and basolateral-to-apical directions. Permeability for Caco-2 cells was determined by the lucifer yellow monolayer integrity test. Caco-2 cells were incubated with UANox048 (5 μM, 2 h) and flux of lucifer yellow across cell monolayers was determined by LC-MS/MS using electrospray ionization. Molecular weight, log D, and polar surface area calculations were performed with ChemDraw software. These data demonstrate favorable characteristics for oral formulation/delivery UANox048 indicating an opportunity for further development.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

In some embodiments, R$^3$ is methyl.

Some of the representative compounds of the invention are provided in Tables 1-4 below:

In some embodiments, the compound is

In some embodiments, the invention provide compounds of the formula wherein
n is 0 or 1;
R$^1$ is optionally substituted aryl;
X$^1$ is —NR$^4$R$^5$, —NR$^b$C(O)R$^6$, —NR$^b$SO$_2$NR$^4$R$^5$ or —NR$^b$SO$_2$R$^6$;
R$^3$ and R$^{3'}$ are each independently hydrogen or alkyl;
each of R$^4$ and R$^5$ is independently hydrogen or alkyl, or R$^4$ and R$^5$ together with the nitrogen atom to which they are attached to form an optionally substituted heterocycloalkyl;
R$^b$ is hydrogen or alkyl; and
R$^6$ is optionally substituted aryl or optionally substituted heterocyclyl.

In some embodiments, the compounds are of formula (Ia), wherein X$^1$ is —NR$^4$R$^5$, —NHC(O)R$^6$, —NHSO$_2$NR$^4$R$^5$ or —NHSO$_2$R$^6$;

What is claimed is:
1. A compound of the formula:

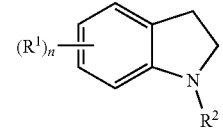

wherein
n is an integer from 0 to 4;
each R$^1$ is independently selected from the group consisting of alkyl, haloalkyl, halogen, nitro, heterocycloalkyl, cycloalkyl, optionally substituted heteroaryl, optionally substituted aryl, and —OR$^a$, where each R$^a$ is independently selected from the group consisting of hydrogen, alkyl, heteroaryl, aryl and cycloalkyl; or
two adjacent R$^1$ together with carbon atoms to which they are attached to form heterocycloalkyl;
R$^2$ is selected from the group consisting of:
(a) a moiety of the formula:

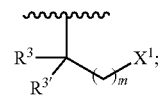

(b) a moiety of the formula:

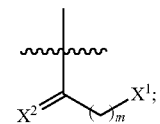

(c) an optionally substituted aryl; and
(d) an optionally substituted heterocycloalkyl,
wherein
m is 1 or 2,
X$^1$ is optionally substituted heterocycloalkyl, —NR$^4$R$^5$, —NR$^b$SO$_2$R$^6$, —NR$^b$C(O)R$^6$, —NR$^b$SO$_2$NR$^4$R$^5$, or —NR$^b$CONR$^4$R$^5$;
X$^2$ is O, NR$^c$ or S;
R$^3$ and R$^{3'}$ are each independently hydrogen or alkyl;
each of R$^4$ and R$^5$ is independently hydrogen or alkyl, or R$^4$ and R$^5$ together with the nitrogen atom to which they are attached to form an optionally substituted heterocycloalkyl;
each of R$^b$ and R$^c$ is independently hydrogen or alkyl; and
R$^6$ is —N(R$^b$)$_2$, optionally substituted aryl, or optionally substituted heterocyclyl;
provided that the compound is not:
N—(N,N-diethylaminosulfonyl)-2-(indolin-1-yl)propane-1-amine);
1,1-diethyl-3-(2-(indolin-1-yl)ethyl)urea;
(N—(N,N-dimethylaminosulfonyl)-2-(indolin-1-yl) ethane-1-amine);
4-(2-(indolin-1-yl)ethyl)morpholine;
1-(2-(piperidin-1-yl)ethyl)indoline;
N-(2-(indolin-1-yl)propyl)morpholine-4-sulfonamide;
N-(2-(indolin-1-yl)propyl)piperidine-1-sulfonamide;

4-fluoro-N-(2-(indolin-1-yl)propyl)benzenesulfonamide;
4-fluoro-N-(2-(indolin-1-yl)ethyl)benzenesulfonamide;
N-(2-(indolin-1-yl)ethyl)-4-methoxybenzenesulfonamide;
3,4-difluoro-N-(2-(indolin-1-yl)propyl)benzenesulfonamide;
N-(2-(indolin-1-yl)propyl)-2,3-dihydrobenzo[b][1,4]dioxine-6-sulfonamide;
N-(2-(indolin-1-yl)ethyl)benzo[d][1,3]dioxole-5-sulfonamide;
N-(2-(indolin-1-yl)ethyl)-2,3-dihydrobenzo[b][1,4]dioxine-6-sulfonamide;
N,N-diethyl-4-(2-(indolin-1-yl)-2-oxoethyl)piperazine-1-sulfonamide;
1-(indolin-1-yl)-2-(4-(morpholinosulfonyl)piperazin-1-yl)ethan-1-one;
1-(indolin-1-yl)-2-(4-(pyrimidin-2-yl)piperazin-1-yl)ethan-1-one;
4-(3-(indolin-1-yl)-3-oxopropyl)-N,N-dimethylpiperazine-1-sulfonamide;
N,N-diethyl-4-(3-(indolin-1-yl)-3-oxopropyl)piperazine-1-sulfonamide;
1-(indolin-1-yl)-3-(4-(morpholinosulfonyl)piperazin-1-yl)propan-1-one;
1-(indolin-1-yl)-3-(4-(pyrimidin-2-yl)piperazin-1-yl)propan-1-one;
2-(cycloheptylamino)-1-(indolin-1-yl)ethan-1-one; or
3-(cycloheptylamino)-1-(indolin-1-yl)propan-1-one.

2. The compound of claim 1 of the formula:

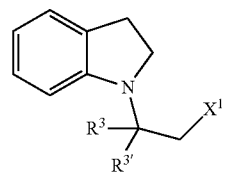

(Ia)

wherein
n is 0 or 1;
$R^1$ is optionally substituted aryl;
$X^1$ is —$NR^4R^5$, —$NR^bC(O)R^6$, —$NR^bSO_2NR^4R^5$ or —$NR^bSO_2R^6$;
$R^3$ and $R^{3'}$ are each independently hydrogen or alkyl;
each of $R^4$ and $R^5$ is independently hydrogen or alkyl, or $R^4$ and $R^5$ together with the nitrogen atom to which they are attached to form an optionally substituted heterocycloalkyl;
$R^b$ is hydrogen or alkyl; and
$R^6$ is optionally substituted aryl or optionally substituted heterocyclyl.

3. The compound of claim 2, wherein
$X^1$ is —$NR^4R^5$, —$NHC(O)R^6$, —$NHSO_2NR^4R^5$ or —$NHSO_2R^6$;
$R^3$ and $R^{3'}$ are each independently hydrogen or methyl;
$R^4$ and $R^5$ are alkyl,
or $R^4$ and $R^5$ together with the nitrogen atom to which they are attached to form an optionally substituted piperazine ring; and
$R^6$ is optionally substituted phenyl or optionally substituted pyrrolidinyl.

4. The compound of claim 3, wherein
n is 1;
$R^1$ is 3-methoxyphenyl; and
$R^4$ and $R^5$ are ethyl.

5. The compound of claim 3, wherein
n is 0;
$R^4$ and $R^5$ together with the nitrogen atom to which they are attached to form piperazine ring substituted with $R^7$, wherein $R^7$ is alkyl —$SO_2R^{12}$ or —$SO_2NR^8R^9$, wherein $R^8$ and $R^9$ are alkyl,
$R^{12}$ is optionally substituted aryl; and
$R^6$ is phenyl or pyrrolidinyl, wherein the phenyl is substituted with one or more of halogen, haloalkyl, —O-haloalkyl, —O-(5-(trifluoromethyl)pyridin-2-yl), —O-phenyl, cyano, -4-methoxyphenyl.

6. The compound of claim 2, wherein $R^3$ and $R^{3'}$ are hydrogen.

7. The compound of claim 2, wherein $R^3$ is hydrogen and $R^{3'}$ is methyl.

8. The compound of claim 2, wherein $R^3$ and $R^{3'}$ are methyl.

9. The compound of claim 1 of formula (Ib)

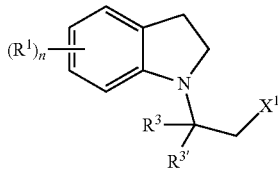

(Ib)

wherein
$X^1$ is —$NR^4R^5$, —$NHC(O)R^6$, —$NHSO_2NR^4R^5$ or —$NHSO_2R^6$;
$R^3$ and $R^{3'}$ are each independently hydrogen or methyl;
when $X^1$ is —$NR^4R^5$, $R^4$ and $R^5$ together with the nitrogen atom to which they are attached to form a piperazine ring, wherein the piperazine ring substituted with $R^7$, wherein $R^7$ is —$SO_2R^{12}$ or —$SO_2NR^8R^9$, wherein
$R^8$ and $R^9$ are alkyl; and
$R^{12}$ is phenyl substituted with halogen or —O-haloalkyl,
when $X^1$ is —$NHC(O)R^6$, $R^6$ is pyrrolidinyl,
when $X^1$ is —$NHSO_2NR^4R^5$, $R^4$ and $R^5$ are alkyl, and
when $X^1$ is —$NHSO_2R^6$, $R^6$ is phenyl substituted with one or more of —O-alkyl, halogen, haloalkyl, —O-haloalkyl, —O-(5-(trifluoromethyl)pyridin-2-yl), —O— phenyl or cyano.

10. The compound of claim 9, wherein
$R^8$ and $R^9$ are ethyl;
$R^{12}$ is phenyl substituted with fluoro or —O—$CF_3$;
$R^4$ and $R^5$ are ethyl; and
when $X^1$ is —$NHSO_2R^6$, $R^6$ is phenyl substituted with one or more of —O-Me, fluoro, —$CF_3$, —O—$CF_3$, —O-(5-(trifluoromethyl)pyridin-2-yl), —O-phenyl or cyano.

11. The compound of claim 9, wherein
$X^1$ is —$NR^4R^5$, —$NHC(O)R^6$ or —$NHSO_2R^6$;
$R^3$ is hydrogen and $R^{3'}$ is hydrogen or methyl;
when $X^1$ is —$NR^4R^5$, $R^4$ and $R^5$ together with the nitrogen atom to which they are attached to form a piperazine ring, wherein the piperazine ring substituted with $R^7$, wherein $R^7$ is —$SO_2R^{12}$ or —$SO_2NR^8R^9$, wherein
$R^8$ and $R^9$ are alkyl; and
$R^{12}$ is phenyl substituted with halogen or —O-haloalkyl, when X¹ is —NHC(O)R⁶, R⁶ is pyrrolidinyl,
when X¹ is —NHSO₂R⁶, R⁶ is phenyl substituted with haloalkyl, —O-haloalkyl, —O-(5-(trifluoromethyl)pyridin-2-yl), —O-phenyl or cyano.

12. The compound of claim 11, wherein
R⁸ and R⁹ are ethyl;
R¹² is phenyl substituted with fluoro or —O—CF₃;
when X¹ is —NHSO₂R⁶, R⁶ is phenyl substituted with —CF₃, —O—CF₃, —O-(5-(trifluoromethyl)pyridin-2-yl), —O-phenyl or cyano.

13. The compound of claim 9, wherein
X¹ is —NHSO₂R⁶;
R³ and R³' are methyl;
R⁶ is phenyl substituted with one or more of —O-alkyl, halogen, haloalkyl, —O-haloalkyl, —O-(5-(trifluoromethyl)pyridin-2-yl), —O-phenyl or cyano.

14. The compound of claim 13, wherein
R⁶ is phenyl substituted with one or more of —OMe, fluoro, —CF₃, —O—CF₃, —O-(5-(trifluoromethyl)pyridin-2-yl), —O-phenyl or cyano.

15. The compound of claim 1, wherein the compound is
N—(N,N-diethylaminosulfonyl)-2-(indolin-1-yl)ethane-1-amine
N-(2-(indolin-1-yl)ethyl)pyrrolidine-1-sulfonamide
1,1-diethyl-3-(2-(indolin-1-yl)propyl)urea
N—(N,N-dimethylaminosulfonyl)-2-(indolin-1-yl)propane-1-amine
N-(2-(indolin-1-yl)propyl)pyrrolidine-1-sulfonamide
N-(2-(indolin-1-yl)ethyl)-4-methylpiperazine-1-carboxamide
N-(2-(indolin-1-yl)ethyl)morpholine-4-sulfonamide
N-(2-(indolin-1-yl)ethyl)piperidine-1-sulfonamide
N-(2-(indolin-1-yl)propyl)-4-methylpiperazine-1-carboxamide
N-(2-(indolin-1-yl)propyl)pyrrolidine-1-carboxamide
N-(2-(indolin-1-yl)ethyl)pyrrolidine-1-carboxamide
1-(indolin-1-yl)-2-(4-(pyrimidin-2-yl)piperazin-1-yl)ethan-1-one
1-(indolin-1-yl)-2-(4-(piperidin-1-ylsulfonyl)piperazin-1-yl)ethan-1-one
4-(2-(indolin-1-yl)-2-oxoethyl)-N,N-dimethylpiperazine-1-sulfonamide
1-(indolin-1-yl)-3-(4-(piperidin-1-ylsulfonyl)piperazin-1-yl)propan-1-one
N-(2-(indolin-1-yl)propyl)-2-(pyridin-4-yl)thiazole-4-carboxamide
N-(2-(indolin-1-yl)propyl)-4-methoxybenzenesulfonamide
N-(2-(5-(3-methoxyphenyl)indolin-1-yl)propyl)-N,N-diethyl-1-sulfonamide
N-(2-(indolin-1-yl)propyl)-4-methylpiperazine-1-sulfonamide
N-(2-(5-(3-methoxyphenyl)indolin-1-yl)propyl)-4-methylpiperazine-1-sulfonamide
N—(N,N-diethylaminosulfonyl)-4-(indolin-1-yl)-phenyl-1-amine
N-(2-(indolin-1-yl)propyl)-4-(trifluoromethyl)benzenesulfonamide
N-(2-(indolin-1-yl)propyl)-4-(trifluoromethoxy)benzenesulfonamide
N-(2-(indolin-1-yl)propyl)-2-(4-methoxyphenyl)thiazole-4-carboxamide
N-(2-(indolin-1-yl)propyl)-2-phenylthiazole-4-carboxamide
N-(2-(indolin-1-yl)propyl)-2-(4-(trifluoromethyl)phenyl)thiazole-4-carboxamide
1-(2-(4-((4-(trifluoromethoxy)phenyl)sulfonyl)piperazin-1-yl)ethyl)indoline
N,N-diethyl-4-(2-(indolin-1-yl)ethyl)piperazine-1-sulfonamide
1-(2-(4-((4-fluorophenyl)sulfonyl)piperazin-1-yl)ethyl)indoline
N,N-diethyl-4-(2-(indolin-1-yl)ethyl)piperazine-1-carboxamide
1-(2-(4-(2-fluorobenzyl)piperazin-1-yl)ethyl)indoline
N-(2-(indolin-1-yl)propyl)-4-((5-(trifluoromethyl)pyridin-2-yl)oxy)benzenesulfonamide
N-(2-(indolin-1-yl)propyl)-4-phenoxybenzenesulfonamide
4-cyano-N-(2-(indolin-1-yl)propyl)benzenesulfonamide
N-(2-(indolin-1-yl)ethyl)-4-(trifluoromethyl)benzenesulfonamide
N-(2-(indolin-1-yl)ethyl)-4-(trifluoromethoxy)benzenesulfonamide
N-(2-(indolin-1-yl)ethyl)-4-phenoxybenzenesulfonamide
N-(2-(indolin-1-yl)ethyl)-4-((5-(trifluoromethyl)pyridin-2-yl)oxy)benzenesulfonamide
3,4-difluoro-N-(2-(indolin-1-yl)ethyl)benzenesulfonamide
4-cyano-N-(2-(indolin-1-yl)ethyl)benzenesulfonamide
N—(N,N-diethylaminosulfonyl)-2-(indolin-1-yl)-2-methylpropane-1-amine
N-(2-(indolin-1-yl)-2-methylpropyl)-4-(trifluoromethyl)benzenesulfonamide
N-(2-(indolin-1-yl)-2-methylpropyl)-4-phenoxybenzenesulfonamide
4-fluoro-N-(2-(indolin-1-yl)-2-methylpropyl)benzenesulfonamide
3,4-difluoro-N-(2-(indolin-1-yl)-2-methylpropyl)benzenesulfonamide
N-(2-(indolin-1-yl)-2-methylpropyl)-4-((5-(trifluoromethyl)pyridin-2-yl)oxy)benzenesulfonamide
N-(2-(indolin-1-yl)-2-methylpropyl)-4-(methoxy)benzenesulfonamide
N-(2-(indolin-1-yl)-2-methylpropyl)-4-(trifluoromethoxy)benzenesulfonamide
or a pharmaceutically acceptable salt thereof.

16. The compound of claim 1, wherein the compound is
N-(2-(indolin-1-yl)propyl)-4-(trifluoromethoxy)benzenesulfonamide
N-(2-(indolin-1-yl)propyl)-4-(trifluoromethyl)benzenesulfonamide
N-(2-(indolin-1-yl)propyl)-4-((5-(trifluoromethyl)pyridin-2-yl)oxy)benzenesulfonamide
N-(2-(indolin-1-yl)ethyl)-4-(trifluoromethyl)benzenesulfonamide
N-(2-(indolin-1-yl)ethyl)-4-(trifluoromethoxy)benzenesulfonamide
N-(2-(indolin-1-yl)ethyl)-4-phenoxybenzenesulfonamide
N-(2-(indolin-1-yl)ethyl)-4-((5-(trifluoromethyl)pyridin-2-yl)oxy)benzenesulfonamide
3,4-difluoro-N-(2-(indolin-1-yl)ethyl)benzenesulfonamide
4-cyano-N-(2-(indolin-1-yl)ethyl)benzenesulfonamide
N-(2-(indolin-1-yl)-2-methylpropyl)-4-(trifluoromethyl)benzenesulfonamide
N-(2-(indolin-1-yl)-2-methylpropyl)-4-phenoxybenzenesulfonamide
N-(2-(indolin-1-yl)-2-methylpropyl)-4-((5-(trifluoromethyl)pyridin-2-yl)oxy)benzenesulfonamide
N-(2-(indolin-1-yl)-2-methylpropyl)-4-methoxybenzenesulfonamide N-(2-(indolin-1-yl)-2-methylpropyl)-4-(trifluoromethoxy)benzenesulfonamide
N-(2-(indolin-1-yl)ethyl)pyrrolidine-1-carboxamide
N—(N,N-diethylaminosulfonyl)-2-(indolin-1-yl)-2-methylpropane-1-amine
1-(2-(4-((4-fluorophenyl)sulfonyl)piperazin-1-yl)ethyl) indoline
1-(2-(4-((4-(trifluoromethoxy)phenyl)sulfonyl)piperazin-1-yl)ethyl)indoline
N,N-diethyl-4-(2-(indolin-1-yl)ethyl)piperazine-1-sulfonamide
or a pharmaceutically acceptable salt thereof.

17. The compound of claim 1, wherein the compound is
N-(2-(indolin-1-yl)ethyl)-4-phenoxybenzenesulfonamide
N-(2-(indolin-1-yl)ethyl)-4-((5-(trifluoromethyl)pyridin-2-yl)oxy)benzenesulfonamide
3,4-difluoro-N-(2-(indolin-1-yl)ethyl)benzenesulfonamide
4-cyano-N-(2-(indolin-1-yl)ethyl)benzenesulfonamide
or a pharmaceutically acceptable salt thereof.

18. The compound of claim 1, wherein the compound is
1-(2-(4-((4-(trifluoromethoxy)phenyl)sulfonyl)piperazin-1-yl)ethyl)indoline
N,N-diethyl-4-(2-(indolin-1-yl)ethyl)piperazine-1-sulfonamide
1-(2-(4-((4-fluorophenyl)sulfonyl)piperazin-1-yl)ethyl) indoline
or a pharmaceutically acceptable salt thereof.

19. A pharmaceutical composition comprising a compound of claim 1 and a pharmaceutically acceptable carrier.

20. A method for treating a clinical condition associated with fibrotic disorder, the method comprising administering to a subject a therapeutically effective amount of the compound of claim 1, or a pharmaceutically acceptable salt thereof, to treat the clinical condition associated with fibrotic disorder.

* * * * *